(12) United States Patent
James et al.

(10) Patent No.: US 10,393,739 B2
(45) Date of Patent: Aug. 27, 2019

(54) BIOMARKERS FOR SYSTEMIC LUPUS ERYTHEMATOSUS DISEASE ACTIVITY, AND INTENSITY AND FLARE

(71) Applicant: Oklahoma Medical Research Foundation, Oklahoma City, OK (US)

(72) Inventors: Judith A. James, Oklahoma City, OK (US); Melissa E. Munroe, Oklahoma City, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 0 days.

(21) Appl. No.: 15/234,754

(22) Filed: Aug. 11, 2016

(65) Prior Publication Data

US 2016/0349256 A1  Dec. 1, 2016

Related U.S. Application Data

(63) Continuation of application No. 14/504,978, filed on Oct. 2, 2014.

(60) Provisional application No. 61/886,189, filed on Oct. 3, 2013.

(51) Int. Cl.
  *G01N 33/68* (2006.01)
  *C12Q 1/6883* (2018.01)
  *G01N 33/564* (2006.01)

(52) U.S. Cl.
  CPC ......... *G01N 33/564* (2013.01); *C12Q 1/6883* (2013.01); *G01N 33/6863* (2013.01); *C12Q 2600/118* (2013.01); *C12Q 2600/158* (2013.01); *G01N 2800/104* (2013.01); *G01N 2800/52* (2013.01)

(58) Field of Classification Search
  None
  See application file for complete search history.

(56) References Cited

U.S. PATENT DOCUMENTS

| | | |
|---|---|---|
| 3,817,837 A | 6/1974 | Rubenstrin et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Littman |
| 4,277,437 A | 7/1981 | Maggio |
| 4,366,241 A | 12/1982 | Tom et al. |
| 4,683,195 A | 7/1987 | Mullis et al. |
| 4,683,202 A | 7/1987 | Mullis |
| 4,800,159 A | 1/1989 | Mullis et al. |
| 4,883,750 A | 11/1989 | Whiteley et al. |
| 5,242,974 A | 9/1993 | Holmes |
| 5,279,721 A | 1/1994 | Schmid |
| 5,384,261 A | 1/1995 | Winkler et al. |
| 5,405,783 A | 4/1995 | Pirrung et al. |
| 5,412,087 A | 5/1995 | McGall et al. |
| 5,424,186 A | 6/1995 | Fodor et al. |
| 5,429,807 A | 7/1995 | Matson et al. |
| 5,436,327 A | 7/1995 | Southern et al. |
| 5,445,934 A | 8/1995 | Fodor et al. |
| 5,472,672 A | 12/1995 | Brennan |
| 5,527,681 A | 6/1996 | Holmes |
| 5,529,756 A | 6/1996 | Brennan |
| 5,532,128 A | 7/1996 | Eggers et al. |
| 5,545,531 A | 8/1996 | Rava et al. |
| 5,554,501 A | 9/1996 | Coassin et al. |
| 5,554,744 A | 9/1996 | Bhongle et al. |
| 5,556,752 A | 9/1996 | Lockhart et al. |
| 5,561,071 A | 10/1996 | Hollenberg et al. |
| 5,571,639 A | 11/1996 | Hubbell et al. |
| 5,593,839 A | 1/1997 | Hubbell et al. |
| 5,599,695 A | 2/1997 | Pease et al. |
| 5,624,711 A | 4/1997 | Sundberg et al. |
| 5,658,734 A | 8/1997 | Brock et al. |
| 5,700,637 A | 12/1997 | Southern |
| 5,840,873 A | 11/1998 | Nelson et al. |
| 5,843,640 A | 12/1998 | Patterson et al. |
| 5,843,650 A | 12/1998 | Segev |
| 5,843,651 A | 12/1998 | Stimpson et al. |
| 5,846,708 A | 12/1998 | Hollis et al. |
| 5,846,709 A | 12/1998 | Segev |
| 5,846,717 A | 12/1998 | Brow et al. |
| 5,846,726 A | 12/1998 | Nadeau et al. |
| 5,846,729 A | 12/1998 | Wu et al. |
| 5,846,783 A | 12/1998 | Wu et al. |
| 5,849,487 A | 12/1998 | Hase et al. |
| 5,849,497 A | 12/1998 | Steinman |
| 5,849,546 A | 12/1998 | Sousa et al. |
| 5,849,547 A | 12/1998 | Cleuziat et al. |

(Continued)

FOREIGN PATENT DOCUMENTS

| | | | |
|---|---|---|---|
| EP | 329 822 A2 | 8/1989 |
| EP | 364 255 A2 | 4/1990 |

(Continued)

OTHER PUBLICATIONS

Capper et al (Clin Exp Immunol 2004; 138:348-356) (Year: 2004).*
Munroe et al (Arthritis and Rheumatism, (Oct. 11, 2012) vol. 64, Supp. Suppl. 10, pp. S279. Abstract No. 645) (Year: 2012).*
Munroe et al (Journal of Immunology, (May 1, 2013) vol. 190, No. 1, Supp. Meeting Abstracts. Abstract No. 46.12) (Year: 2013).*
Bauer, J.W. et al., "Interferon-Regulated Chemokines as Biomarkers of Systemic Lupus Erythematosus Disease Activity," Arthritis & Rheumatism, Oct. 2009, pp. 3098-3107, vol. 60, No. 10.
Dolff, S. et al., "Disturbed Th1, Th2, Th17 and $T_{reg}$ Balance in Patients with Systemic Lupus Erythematosus," Clinical Immunology, 2011, pp. 197-204, vol. 141.

(Continued)

*Primary Examiner* — Brian Gangle
*Assistant Examiner* — Andrea K McCollum
(74) *Attorney, Agent, or Firm* — Goodwin Procter LLP

(57) ABSTRACT

The present invention involves the identification of biomarkers that are predictive of impeding systemic lupus erythematosus (SLE) disease flare. Methods for treating patients so identified are also provided.

7 Claims, 14 Drawing Sheets

(11 of 14 Drawing Sheet(s) Filed in Color)

(56) References Cited

U.S. PATENT DOCUMENTS

| | | | |
|---|---|---|---|
| 5,853,990 | A | 12/1998 | Winger et al. |
| 5,853,992 | A | 12/1998 | Glazer et al. |
| 5,853,993 | A | 12/1998 | Dellinger et al. |
| 5,856,092 | A | 1/1999 | Dale et al. |
| 5,858,652 | A | 1/1999 | Laffler et al. |
| 5,861,244 | A | 1/1999 | Wang et al. |
| 5,863,732 | A | 1/1999 | Richards |
| 5,863,753 | A | 1/1999 | Haugland et al. |
| 5,866,331 | A | 2/1999 | Singer et al. |
| 5,866,366 | A | 2/1999 | Kallender |
| 5,882,864 | A | 3/1999 | An et al. |
| 5,905,024 | A | 5/1999 | Mirzabekov et al. |
| 5,910,407 | A | 6/1999 | Vogelstein et al. |
| 5,912,124 | A | 6/1999 | Kumar |
| 5,912,145 | A | 6/1999 | Stanley |
| 5,912,148 | A | 6/1999 | Eggerding |
| 5,916,776 | A | 6/1999 | Kumar |
| 5,916,779 | A | 6/1999 | Pearson et al. |
| 5,919,630 | A | 7/1999 | Nadeau et al. |
| 5,922,574 | A | 7/1999 | Minter |
| 5,925,517 | A | 7/1999 | Tyagi et al. |
| 5,928,862 | A | 7/1999 | Morrison |
| 5,928,869 | A | 7/1999 | Nadeau et al. |
| 5,928,905 | A | 7/1999 | Stemmer et al. |
| 5,928,906 | A | 7/1999 | Koster et al. |
| 5,929,227 | A | 7/1999 | Glazer et al. |
| 5,932,413 | A | 8/1999 | Celebuski |
| 5,932,451 | A | 8/1999 | Wang et al. |
| 5,935,791 | A | 8/1999 | Nadeau et al. |
| 5,935,825 | A | 8/1999 | Nishimura et al. |
| 5,939,291 | A | 8/1999 | Loewy et al. |
| 5,942,391 | A | 8/1999 | Zhang et al. |
| 6,004,755 | A | 12/1999 | Wang |
| 2006/0094056 | A1 | 5/2006 | Chappell et al. |
| 2013/0071860 | A1 | 3/2013 | Hale et al. |

FOREIGN PATENT DOCUMENTS

| | | |
|---|---|---|
| GB | 2 202 328 A | 9/1988 |
| WO | WO 87/06270 A1 | 10/1987 |
| WO | WO 88/10315 A1 | 12/1988 |
| WO | WO 89/06700 A1 | 7/1989 |
| WO | WO 89/09284 A1 | 10/1989 |
| WO | WO 90/07641 A1 | 7/1990 |
| WO | WO 2011/047358 | 4/2011 |
| WO | WO 2011/047358 A1 | 4/2011 |

OTHER PUBLICATIONS

Jara, L.J. et al., Risk Factors of Systemic Lupus Erythematosus Flares During Pregnancy, Immunol. Res., 2014, pp. 184-192, vol. 60.

McCarthy, E.M. et al., "The Association of Cytokines with Disease Activity and Damage Scores in Systemic Lupus Erythematosus Patients," Rheumatology, 2014, pp. 1586-1594, vol. 53.

Munroe, M.E. et al., "Pro-Inflammatory Adaptive Cytokines and Shed Tumor Necrosis Factor Receptors are Elevated Preceding Systemic Lupus Erythematosus Disease Flare," Arthritis Rheumatol., Jul. 2014, pp. 1888-1899, vol. 66, No. 7.

Talaat, R.M. et al, "Th1/Th2/Th17/Treg Cytokine Imbalance in Systemic Lupus Erythematosus (SLE) Patients," Cytokine, 2015, pp. 146-153, vol. 72.

Adhya et al., "The Role of Cytokines as Biomarkers in Systemic Lupus Erythematosus and Lupus Nephritis," Nephrol. Dial. Transplant, 26(10):3273-3280, 2011.

Alvarado-Sanchez et al., "Regulatory T Cells in Patients with Systemic Lupus Erythematosus," J Autoimmun., 27(2): 110-8, 2006.

Becker-Merok et al., "Levels of Transforming Growth Factor-Beta are Low in Systemic Lupus Erythematosus Patients with Active Disease," J Rheumatol. 37(10):2039-45, 2010.

Bonelli et al., "Quantitative and Qualitative Deficiencies of Regulatory T Cells in Patients with Systemic Lupus Erythematosus (SLE)," Int Immunol., 20(7):861-8, 2008.

Chen et al., "The Potential Role of Th17 Cells and Th17-Related Cytokines in the Pathogenesis of Lupus Nephritis," Lupus, 21(13): 1385-96, 2012.

Chun et al., "Cytokine IL-6 and IL-10 as Biomarkers in Systemic Lupus Erythematosus," J Cl in. Immunol., 27(5):461-6, 2007.

Davas et al., "Serum IL-6, TNFalpha, p55 srTNFalpha, p75srTNFalpha, srIL-2alpha Levels and Disease Activity in Systemic Lupus Erythematosus," Clin Rheumatol., 18(1):17-22, 1999.

Desai-Mehta et al., "Hyperexpression ofCD40 Ligand by Band T Cells in Human Lupus and its Role in Pathogenic Autoantibody Production," J Clin. Invest., 97(9):2063-73, 1996.

Dillon et al., "B-lymphocyte Stimulator/a Proliferation-Inducing Ligand Heterotrimers are Elevated in the Sera of Patients with Autoimmune Disease and are Neutralized by Atacicept and Bcell Maturation Antigen-Immunoglobulin," Arthritis Res Ther., 12(2):R48, 2010.

Gomez et al., "Th1/Th2 Cytokines in Patients with Systemic Lupus Erythematosus: is Tumor Necrosis Factor Alpha Protective?," Semin. Arthritis Rheum., 33(6):404-13, 2004.

Ma et al., "The Imbalance Between Regulatory and IL-1 7-Secreting CD4+ T Cells in Lupus Patients," Clin. Rheumatol., 29(11):1251-8, 2010.

Miyara et al., "Global Natural Regulatory T Cell Depletion in Active Systemic lupus Erythematosus," J Immunol., 175(12):8392-400, 2005.

Mok et al., "The Relation of Interleukin 17 (IL-17) and IL-23 to Th1/Th2 Cytokines and Disease Activity in Systemic Lupus Erythematosus," J Rheumatol., 37(10):2046-52, 2010.

Okamoto et al., "Regulatory T-Cell-Associated Cytokines in Systemic Lupus Erythematosus," Biomed Biotechnol., 2011:463412, 2011.

PCT International Search Report and Written Opinoin issued in International Patent Application No. PCT/US14/58812, dated Dec. 22, 2014.

Petri et al., "Association of Plasma B Lymphocyte Stimulator Levels and Disease Activity in Systemic Lupus Erythematosus," Arthritis Rheum., 58(8):2453-9, 2008.

Qin et al., "TACI-Ig Induces Immune Balance of Th Cells in MLN via BLyS/APRIL-Receptors Signaling in Rats with Adjuvant-Induced Arthritis," Int. Immunopharmacol., 11(12):2167-75, 2011.

Tinazzi et al., "Serum DNase I, Soluble Fas/FasL Levels and Cell Surface Fas Expression in Patients with SLE: a Possible Explanation for the Lack of Efficacy ofhrDNase I Treatment," Int Immunol., 21(3):237-43, 2009.

Tokano et al., "Levels of IL-12 in the Sera of Patients with Systemic Lupus Erythematosus (SLE)—Relation to Th1- and Th2-Derived Cytokines," Clin Exp Immunol., 116(1): 169-73, 1999.

Vargas-Rojas et al., "Quantitative and Qualitative Normal Regulatory T Cells are Not Capable of Inducing Suppression in SLE Patients Due to T-Cell Resistance," Lupus, 17(4):289-94, 2008.

Liu et al (Ther Adv Musculoskelet Dis. Aug. 2013;5(4):210-33).

Siddani et al (PLoS One. Dec. 2, 2013;8(12):e81766).

Waiker et al (J Am Soc Nephrol. Jan. 2012; 23(1 ): 13-21).

Munroe, M.E. et al., "Pro-Inflammatory Adaptive Cytokines and Shed Tumor Necrosis Factor Receptors are Elevated Preceding Systemic Lupus Erythematosus Disease Flare," Arthritis & Rheumatology, Jul. 2014, pp. 1888-1899, vol. 66, No. 7.

Munroe ,M.E. et al., "Altered Type II Interferon Precedes Autoantibody Accrual and Elevated Type I Interferon Activity Prior to Systemic Lupus Erythematosus Classification," Ann. Rheum. Dis. Dec. 19, 2016, 9 pages.

United States Office Action, U.S. Appl. No. 14/504,978, dated Feb. 11, 2016, 25 pages.

Abu-Shakra, M. et al., "Influenza Virus Vaccination of Patients with Systemic Lupus Erythematosus: Effects on Disease Activity," The Journal of Rheumatology, 2000, pp. 1681-1685, vol. 27, No. 7.

Arend, W.P., "The Balance Between IL-1 and IL-1Ra in Disease," Cytokine & Growth Factor Reviews, 2002, pp. 323-340, vol. 13, No. 4-5.

Bruner, B.F. et al., "Comparison of Autoantibody Specificities Between Traditional and Bead-Based Assays in a Large, Diverse

(56) References Cited

OTHER PUBLICATIONS

Collection of SLE Patients and Family Members," Arthritis Rheum., Nov. 2012, pp. 3677-3686, vol. 64, No. 11.

Chen, X. et al., "The Phenotypic and Functional Consequences of Tumour Necrosis Factor Receptor Type 2 Expression on CD4+ FoxP3+ Regulatory T Cells," and Oppenheim, Immunology, 133(4):426-33, 2011.

Chu, V.T. et al., "Systemic Activation of the Immune System Induces Aberrant BAFF and APRIL Expression in B Cells in Patients With Systemic Lupus Erythematosus," Arthritis & Rheumatism, Jul. 2009, pp. 2083-2093, vol. 60, No. 7.

Croft, M. et al., "Clinical Targeting of the TNF and TNFR Superfamilies," Nat Rev Drug Discov., Feb. 2013, pp. 147-168, vol. 12, No. 2.

Crowe, S.R. et al., "Influenza Vaccination Responses in Human Systemic Lupus Erythmatosus: Impact of Clinical and Demographic Features," Arthritis Rheum., Aug. 2011, pp. 2396-2406, vol. 63, No. 8.

De Jager, R. et al., "Current Status of Cancer Immunodetection with Radiolabeled Human Monoclonal Antibodies," Seminars in Nuclear Medicine, Apr. 1993, pp. 165-179, vol. 23, No. 2.

Doolittle, M.H. et al., "Immunodetection of Lipoprotein Lipase: Antibody Production, Immunoprecipitation, and Western Blotting Techniques," Lipase and Phospholipase Protocols, Doolittle et al. (eds.), Methods in Molecular Biology, 1999, pp. 215-237, vol. 109.

Dossus, L. et al., "Validity of Multiplex-Based Assays for Cytokine Measurements in Serum and Plasma from "Non-Diseased" Subjects: Comparison with ELISA," Journal of Immunological Methods, 2009, pp. 125-132, vol. 350, No. 1-2.

Dupont, N.C. et al., "Validation and Comparison of Luminex Multiplex Cytokine Analysis Kits with ELISA: Determinations of a Panel of Nine Cytokines in Clinical Sample Culture Supernatants," Journal of Reproductive Immunology, 2005, pp. 175-191, vol. 66, No. 2.

Gulbis, B. et al., "Immunodetection of the p21-ras Products in Human Normal and Preneoplastic Tissues and Solid Tumors: A Review," Human Pathology, Dec. 1993, pp. 1271-1285, vol. 24, No. 12.

Hochberg, M.C., "Letters: Updating the American College of Rheumatology Revised Criteria for the Classification of Systemic Lupus Erythematosus," Arthritis & Rheumatism, Sep. 1997, p. 1725, vol. 40, No. 9.

Hughes-Austin, J.M. et al., "Multiple Cytokines and Chemokines are Associated with Rheumatoid Arthritis-Related Autoimmunity in First-Degree Relatives Without Rheumatoid Arthritis: Studies of the Aetiology of Rheumatoid Arthritis (SERA)," Ann. Rheum. Dis., Jun. 2013, pp. 901-907, vol. 72, No. 6.

Innis, M.A. et al., "DNA Sequencing with Thermus aquaticus DNA Polymerase and Direct Sequencing of Polymerase Chain Reaction-Amplified DNA," Proc. Natl. Acad. Sci. USA, Dec. 1988, pp. 9436-9440, vol. 85, No. 24.

Kwoh, D.Y. et al., "Transcription-Based Amplification System and Detection of Amplified Human Immunodeficiency Virus Type 1 With a Bead-Based Sandwich Hybridization Format," Proc. Natl. Acad. Sci. USA, Feb. 1989, pp. 1173-1177, vol. 86.

Lam, G.K.W. et al., "Assessment of Systemic Lupus Erythematosus," Clin. Exp. Rheumatol., 2005, pp. S120-S132, vol. 23, No. 5 Suppl 39.

Lau, C.S. et al., "The Socioeconomic Burden of SLE," Nat. Rev. Rheumatol., Jul. 2009, pp. 400-404, vol. 5, No. 7.

Lu, R. et al., "Multiple Autoantibodies Display Association with Lymphopenia, Proteinuria, and Cellular Casts in a Large, Ethnically Diverse SLE Patient Cohort," Autoimmune Diseases Doc Id. 819634, 2012, 11 pages.

Mok, C.C. et al., "Immunogenicity and Safety of a Quadrivalent Human Papillomavirus Vaccine in Patients with Systemic Lupus Erythematosus: A Case-Control Study," Ann. Rheum Dis., 2013, pp. 659-664, vol. 72, No. 5.

Mueller, P.R. et al., "In Vivo Footprinting of a Muscle Specific Enhancer by Ligation Mediated PCR," Science, Nov. 10, 1989, pp. 780-786, vol. 246, No. 4931.

Ohara, O. et al., "One-Sided Polymerase Chain Reaction: The Amplification of cDNA," Proc. Natl. Acad. Sci. USA, Aug. 1989, pp. 5673-5677, vol. 86.

Petri, M. et al., "Prevalence of Flare and Influence of Demographic and Serologic Factors on Flare Risk in Systemic Lupus Erythematosus: A Prospective Study," The Journal of Rheumatology, 2009, pp. 2476-2480, vol. 36, No. 11.

Petri, M. et al., "Combined Oral Contraceptives in Women with Systemic Lupus Erythematosus," The New England Journal of Medicine, Dec. 15, 2005, pp. 2550-2558, vol. 353, No. 24.

Ruperto, N. et al., "International Consensus for a Definition of Disease Flare in Lupus," Lupus, 2010, pp. 453-462, vol. 20.

Mayer, M.P., "A New Set of Useful Cloning and Expression Vectors Derived from pBlueScript," Gene, 1995, pp. 41-46, vol. 163.

Shah, K. et al., "Dysregulated Balance of Th17 and Th1 Cells in Systemic Lupus Erythematosus," Arthritis Research & Therapy, 2010, pp. 1-10, vol. 12, No. 2, R53.

Sokolove, J. et al., "Autoantibody Epitope Spreading in the Pre-Clinical Phase Predicts Progression to Rheumatoid Arthritis," PLoS One, May 2012, 9 pages, vol. 7, No. 5, e35296.

Stringer, E.A. et al., "Daily Cytokine Fluctuations, Driven by Leptin, Are Associated with Fatigue Severity in Chronic Fatigue Syndrome: Evidence of Inflammatory Pathology," Journal of Translational Medicine, 2013, 11 page, vol. 11, No. 93.

Van Mierlo, G.J.D. et al., "Cutting Edge: TNFR-Shedding by CD4+ CD25+ Regulatory T Cells Inhibits the Induction of Inflammatory Mediators," The Journal of Immunology, 2008, pp. 2747-2751, vol. 180, No. 5.

Walker, G.T. et al., "Strand Displacement Amplification—an Isothermal, in vitro DNA Amplification Technique," Nucleic Acids Research, 1992, pp. 1691-1696, vol. 20, No. 7.

Wang, Z. et al., "Cux/CDP Homeoprotein Is a Component of NF-µNR and Represses the Immunoglobulin Heavy Chain Intronic Enhancer by Antagonizing the Bright Transcription Activator," Molecular and Cellular Biology, Jan. 1999, pp. 284-295, vol. 19.

Wang, J. et al., "A Protein Interaction Network for Pluripotency of Embryonic Stem Cells," Nature, Nov. 2006, pp. 364-368, vol. 444.

PCT International Search Report and Written Opinion, PCT Application No. PCT/US14/58812, Dec. 22, 2014, 7 pages.

Adhya, Z. et al., "The Role of Cytokines as Biomarkers in Systemic Lupus Erythematosus and Lupus Nephritis," Nephrol. Dial. Transplant, Mar. 3, 2011, pp. 3273-3280, vol. 26, No. 10.

Espinosa et al., "Belimumab, a BLyS-Specific Inhibitor for the Treatment of Systemic Lupus Erythematosus," Drugs of Today, 2010, pp. 891-899, vol. 46, No. 12.

Arbuckle, M., et al., "Development of Autoantibodies before the Clinical Onset of Systemic Lupus Erythematosus," The New England Journal of Medicine, Oct. 16, 2003, 349, pp. 1526-1533.

Cancro, M.P. et al., "The role of B lymphocyte stimulator(BLyS) in systemic lupus erythematosus," J. Clin. Invest. 119 (2009) 1066-1073.

Chen, X.Q. et al., "Plasma IL-17A isincreased in new-onset SLE patients and associated with disease activity," J. Clin. Immunol. 30(2010) 221-225.

Deane, K.D. et al., "Identification of undiagnosed inflammatory arthritis in a community health fair screen," ArthritisRheum. 61 (2009) 1642-1649.

Deane, K.D. et al., "The number of elevated cytokines and chemokines in preclinical seropositive rheumatoid arthritispredicts time to diagnosis in an age-dependent manner," Arthritis Rheum. 62 (2010) 3161-3172.

Eilertsen, G.O. et al., "Interleukin-6 promotes arthritis and joint deformation in patients with systemic lupus erythematosus," Lupus 20 (2011) 607-613.

Harigai, M. et al., "Excessive production of IFN-yamma in patients with systemic lupus erythematosus and its contribution to induction of B lymphocyte stimulator/B cell-activating factor/TNF ligand superfamily-13B," J. Immunol. 181 (2008) 2211-2219.

(56) References Cited

OTHER PUBLICATIONS

Linker-Israeli, M. et al., "Elevated levels of endogenous IL-6 in systemic lupus erythematosus. A putative role inpathogenesis," J. Immunol. 147 (1991) 117-123.

Llorente, L. et al., "Dysregulation of interleukin-l0 production in relatives of patients with systemiclupus erythematosus," Arthritis Rheum 1997;40: 1429-35.

Niewold, T.B. et al., "High serum IFN-a activity isa heritable risk factor for systemic lupus erythematosus" Genes Immun 2007;8:492-502.

Ohtsuka, K. et al., "The relationship between defectsin lymphocyte production of transforming growth factor-beta I in systemic lupus erythematosus anddisease activity or severity," Lupus 8 (1999) 90-94.

Oliveira, S.H. et al., "Stem cell factor: a hemopoietic cytokine with importanttargets in asthma" Curr Drug Targets Inflamm Allergy 2003;2:313-8.

Rullo, O.J. et al., "Recent insights into the genetic basis of systemic lupuserythematosus" Ann Rheum Dis 2013;72 Suppl 2: ii56-61.

Viallard, J.F. et al., "Analysis ofinterleukin-6, interleukin-lO and leukemia inhibitory factor (LIF) production by peripheral bloodcells from patients with systemic lupus erythematosus identifies LIF as a potential marker of diseaseactivity," Eur. Cytokine Netw. 10 (1999) 17-24.

Vila, L.M. et al., "Clinical outcome and predictors of disease evolution in patients with incomplete lupus erythematosus," Lupus 9 (2000) 110-115.

Wahren-Herlenius, M. et al., "Immunopathogenesis mechanisms of systemicautoimmune disease," Lancet 382 (2013) 819-831.

Wandstrat, A.E. et al., "Autoantibody profiling to identify individuals at risk for systemic lupus erythematosus," J. Autoimmun. 27 (2006) 153-160.

Wong, C.K. et al., "Elevation of proinflammatory cytokine (1L-18, IL-17, IL-12) and Th2 cytokine (IL-4) concentrations in patients with systemic lupus erythematosus," Lupus 9 (2000) 589-593.

Yap, D.Y. et al., "Cytokines and their roles in the pathogenesis of systemic lupuserythematosus: from basics to recent advances," J. Biomed. Biotechnol. 2010, 365083, 10 pages.

\* cited by examiner

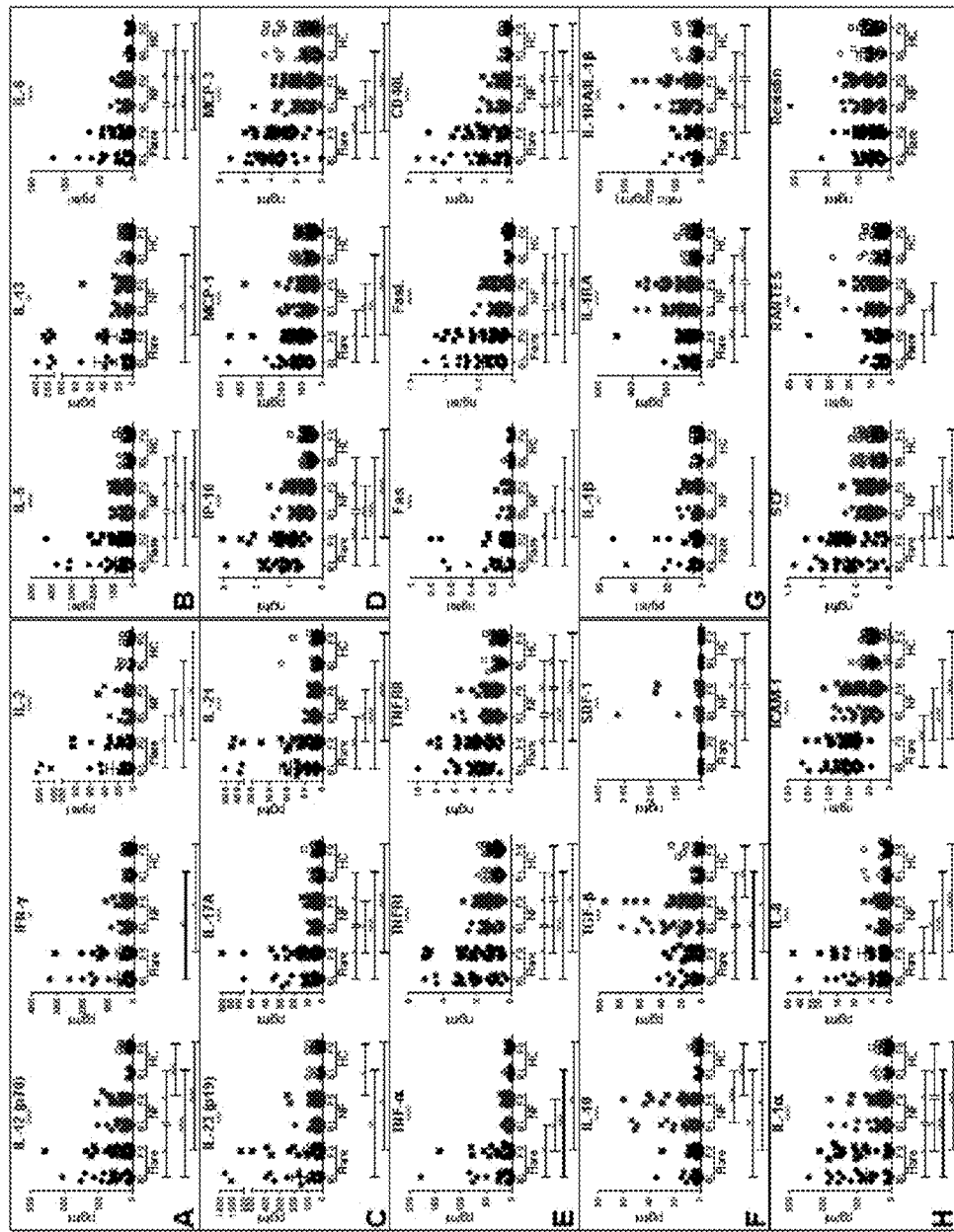
FIGS. 6A-H

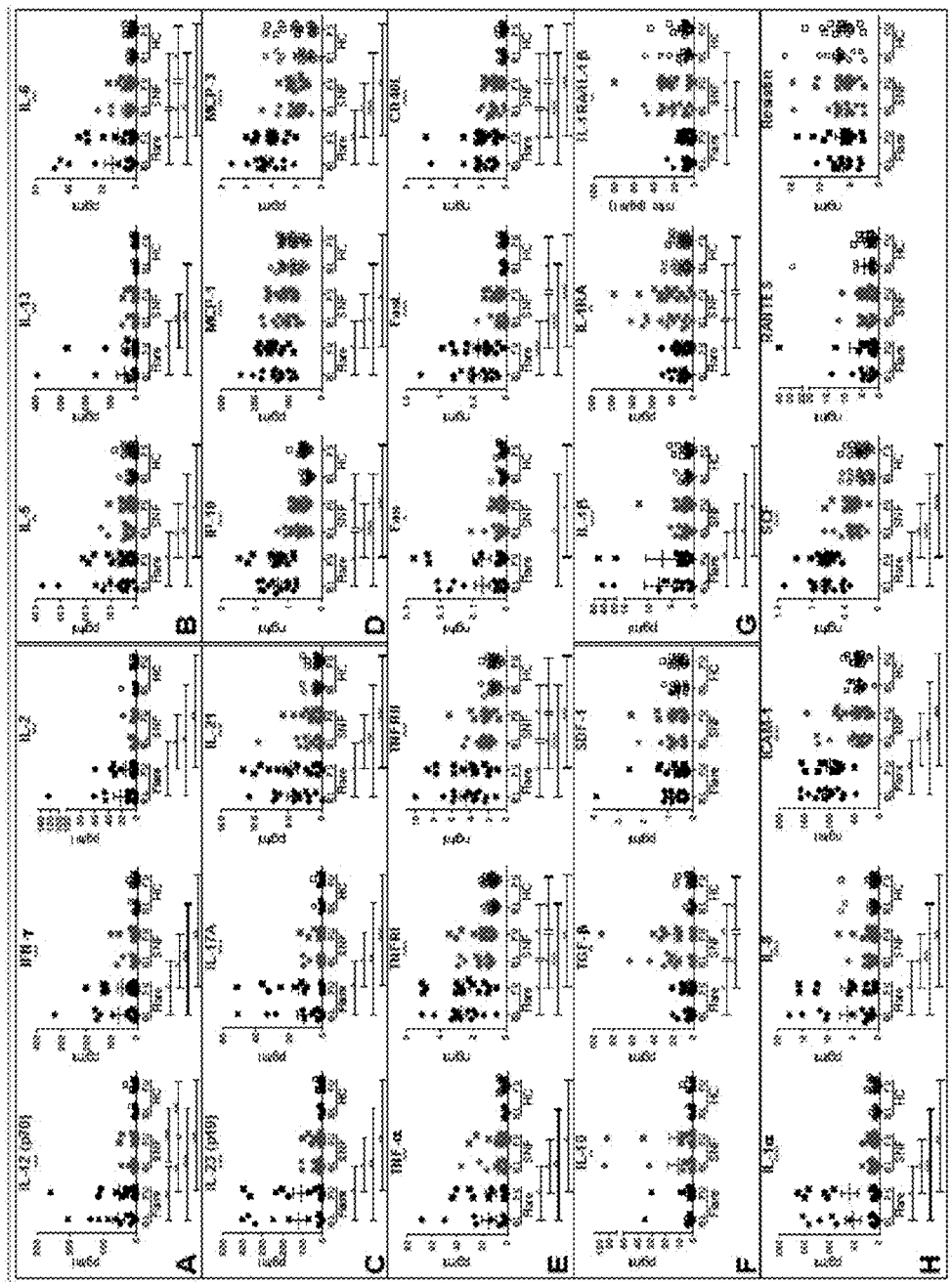
FIGS. 7A-H

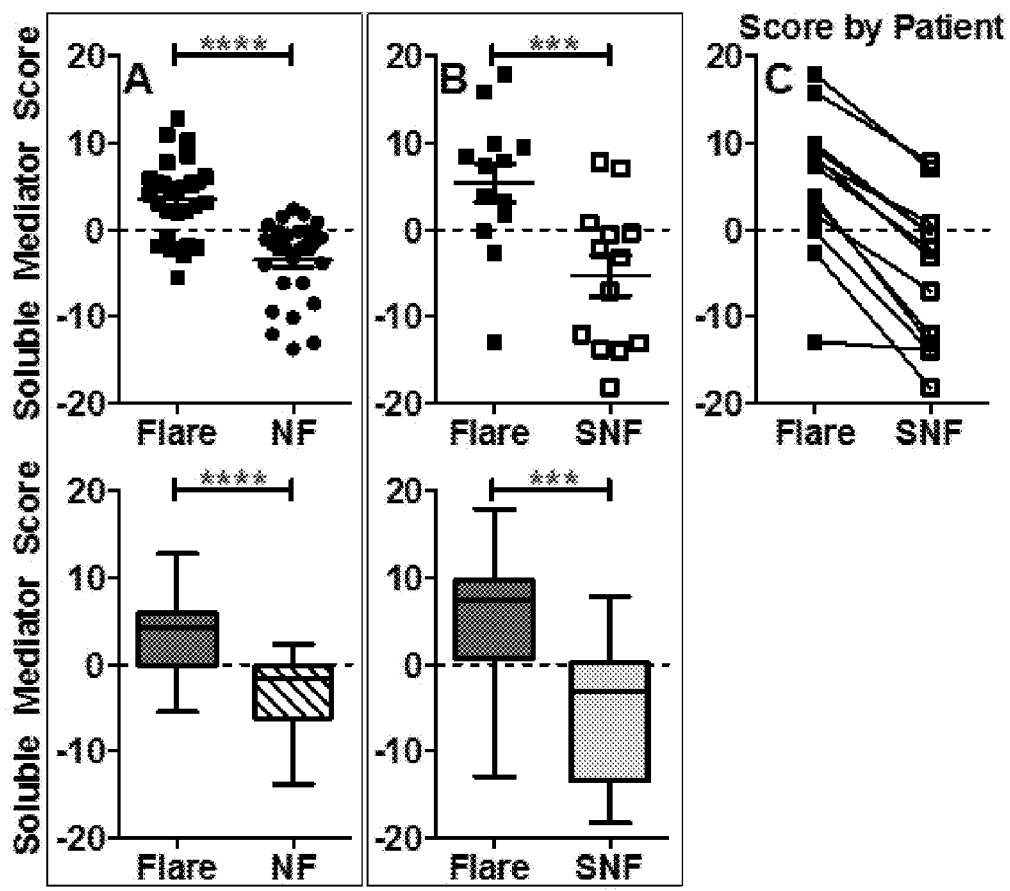
FIGS. 8A-C

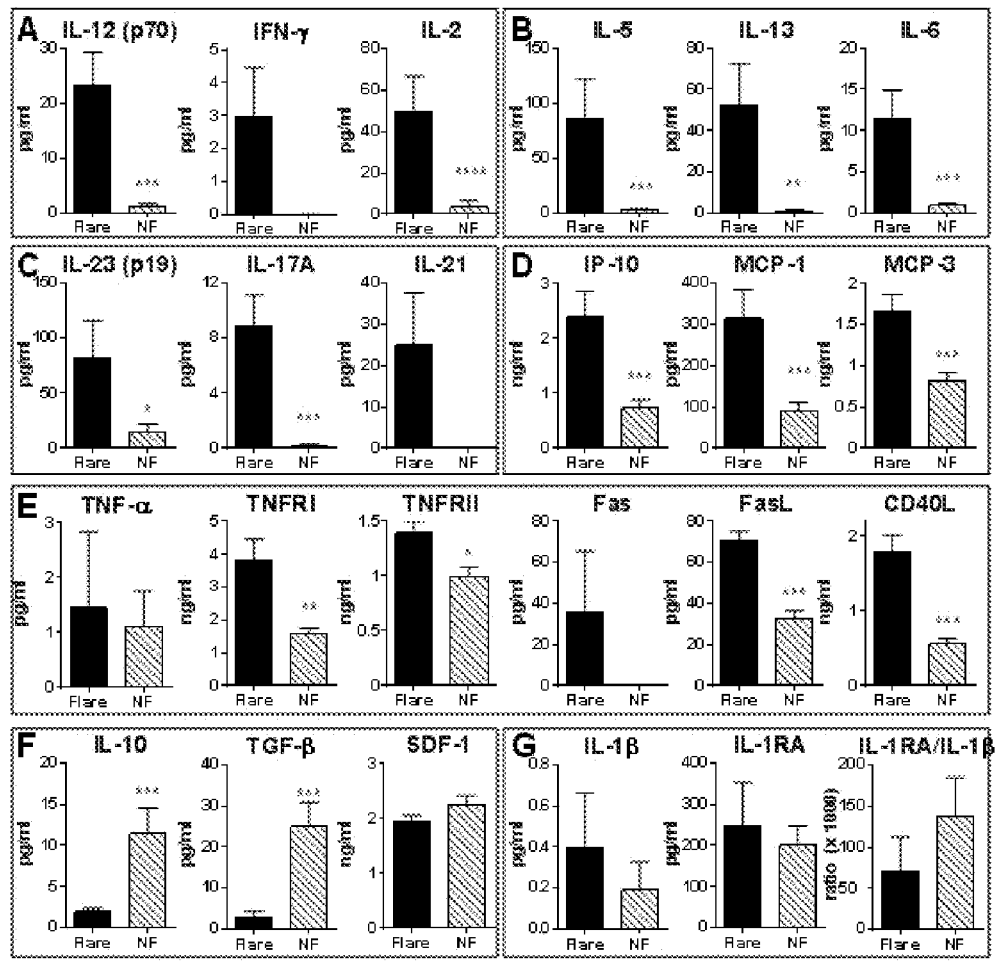
FIGS. 9A-G

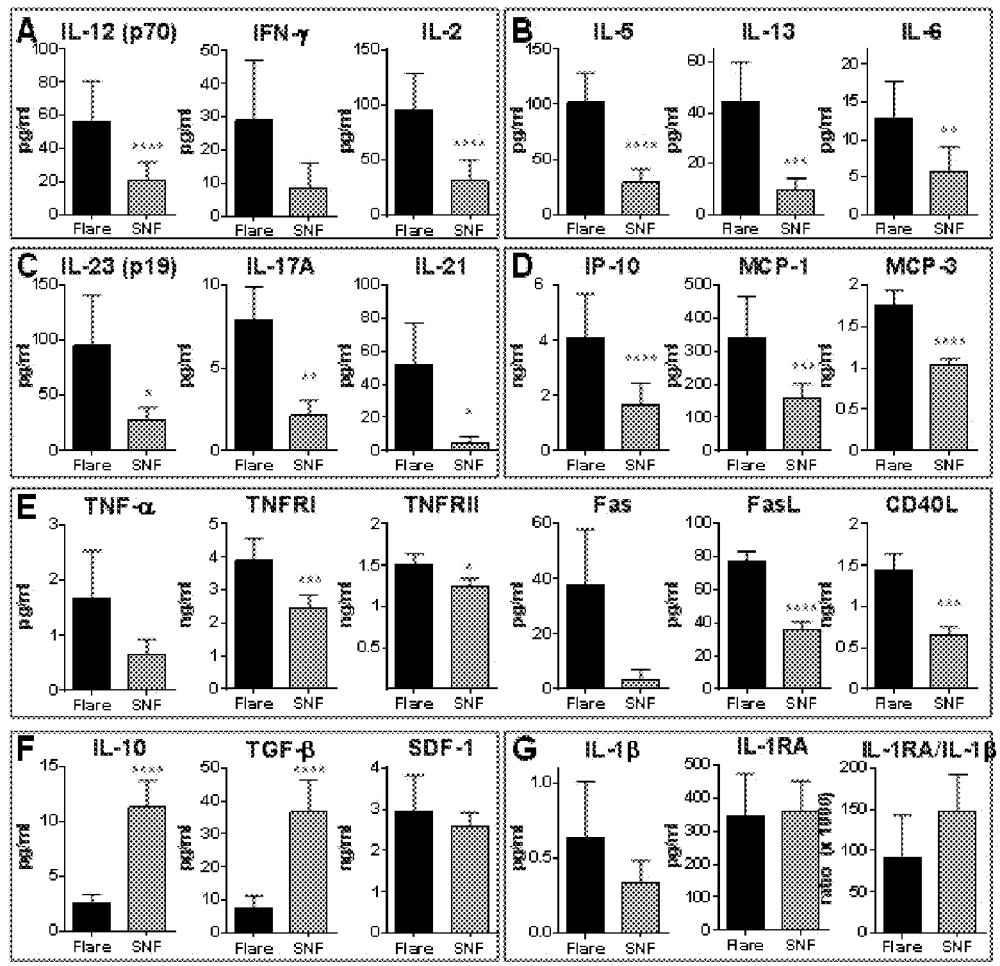
FIGS. 10A-G

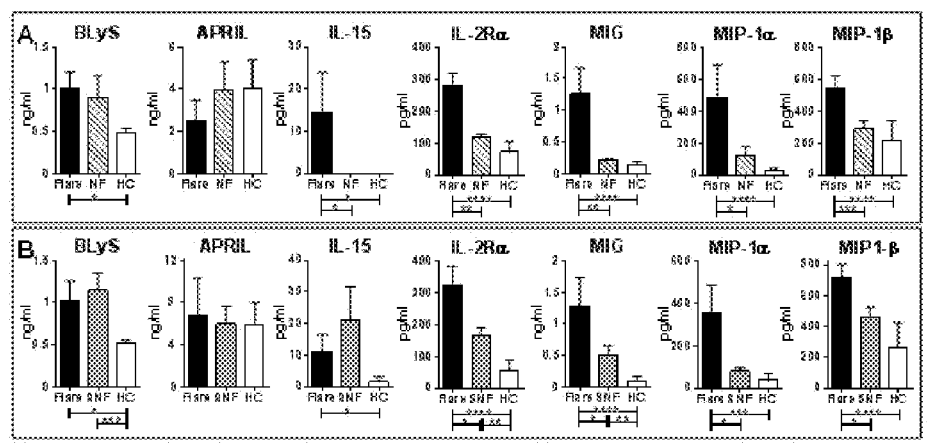
FIGS. 11A-B

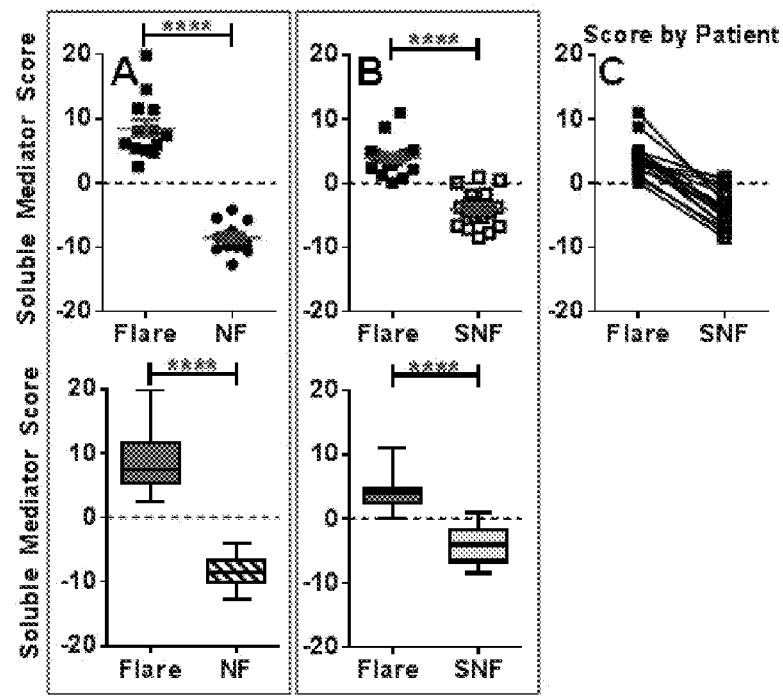
FIGS. 12A-C

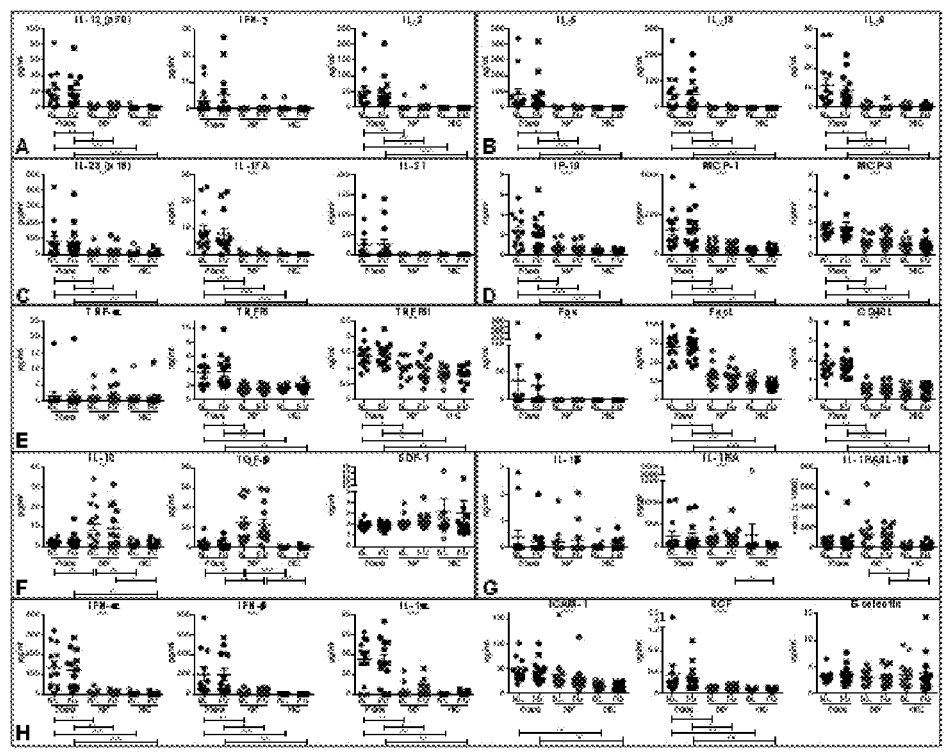
FIGS. 13A-H

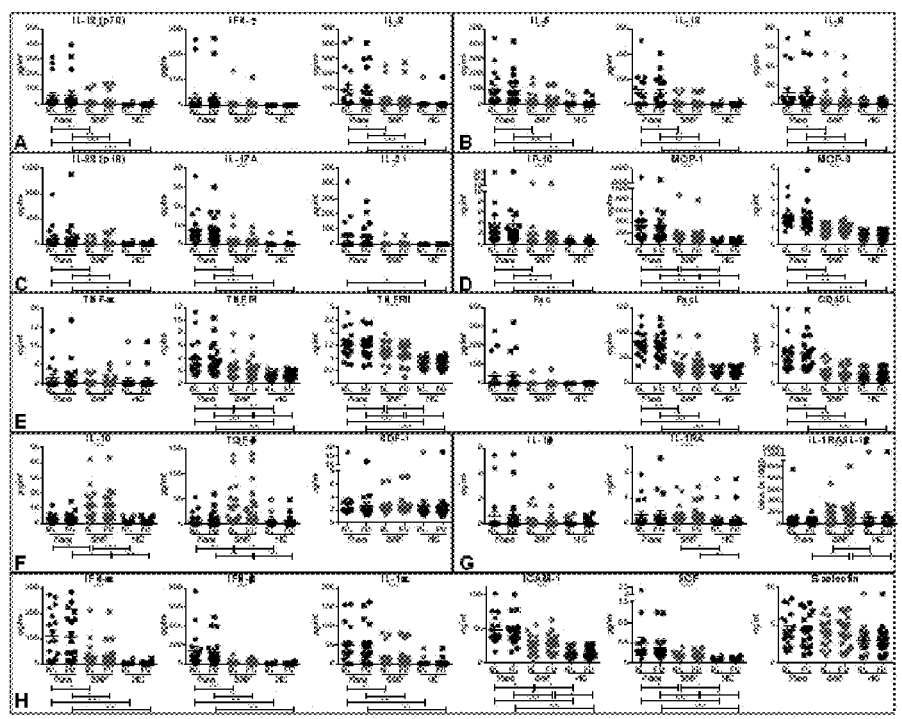
FIGS. 14A-H

BIOMARKERS FOR SYSTEMIC LUPUS ERYTHEMATOSUS DISEASE ACTIVITY, AND INTENSITY AND FLARE

RELATED APPLICATION DATA

This application is a continuation of U.S. application Ser. No. 14/504,978 filed on Oct. 2, 2014, which claims priority to U.S. Provisional Application Ser. No. 61/886,189, filed Oct. 3, 2013, the entire contents of which are hereby incorporated by reference.

GOVERNMENT SUPPORT CLAUSE

This invention was made with government support under grant no. P30AR053483, U19AI082714, U01AI101934, P30GM103510, S10RR026735, HHSN266200500026C, and U54GM104938 awarded by the National Institutes Health. The government has certain rights in the invention.

BACKGROUND OF THE INVENTION

1. Field of the Invention

The present invention relates generally to the fields of autoimmune disease, immunology, rheumatology and molecular biology. More particularly, it concerns soluble inflammatory mediators that are predictive of and involved in systemic lupus erythematosus flares.

2. Description of Related Art

Systemic lupus erythematosus (SLE) is a multifaceted autoimmune disease characterized by variable immune dysregulation, disabling symptoms and progressive organ damage (Lam and Petri, 2005). Given the heterogeneous nature of SLE, recognition and early treatment to prevent tissue and organ damage is clinically challenging. Validated disease activity clinical instruments assess and weight changes in signs and symptoms within each organ system. The Safety of Estrogens in Lupus Erythematosus National Assessment-Systemic Lupus Erythematosus Disease Activity Index (SELENA-SLEDAI) (Petri et al., 2005.) is a reliable measure of clinical disease activity (Lam and Petri, 2005). However, the traditional biomarkers incorporated in the SELENA-SLEDAI are not necessarily the earliest or sufficient biologic signals of worsening disease. Despite clinical instruments of disease activity and improved treatment regimens to temper chronic inflammation, SLE patients may experience an average of 1.8 disease flares annually (Petri et al., 2009). Treatment typically relies on rapidly acting, side effect-pervaded agents such as steroids. Earlier identification of flares might open the door for proactive strategies to reduce pathogenic and socioeconomic burdens of SLE (Lau and Mak, 2009). Further, uncovering early markers of clinical flares will provide mechanistic insight, improving the development of targeted preventative treatments.

Certain cytokines and chemokines are known to be involved in SLE pathogenesis and disease flare. IL-6, TNF-α, and IL-10, as well as Th1 and Th2 type cytokines, have been implicated in SLE disease activity (Davas et al., 1999; Chun et al., 2007 and Gomez et al., 2004); elevated IL-12 has been detected prior to disease flare (Tokano et al., 1999). Th17 pathway mediators have been implicated in increased disease activity (Shah et al., 2010) and sequelae, including cutaneous (Mok et al., 2010.), serositis (Mok et al., 2010.), and renal (Chen et al., 2012) manifestations. These changes, along with decreased TGF-β (Becker-Merok et al., 2010) and reduced numbers of natural T-regulatory cells (Miyara et al., 2005) with active disease, suggest an imbalance between inflammatory and regulatory mediators in promoting flares (Ma et al., 2010). This study builds on previous work by concurrently evaluating soluble inflammatory and regulatory mediators in the context of altered disease activity with ensuing SLE disease flare.

Cytokines and chemokines are indicative of the ongoing immune response to (auto)antigens. In addition to soluble mediators of inflammation, SLE flares might also involve altered regulation of membrane-bound or soluble receptors expressed by activated cells (Davas et al., 1999). Members of the TNF-(R)eceptor superfamily form a prototypic proinflammatory system that act as co-stimulatory molecules on B and T-lymphocytes (reviewed in Croft et al., 2013). The ligand/receptor pairings are either membrane bound or can be cleaved by proteases as soluble proteins that cluster as trimers to either block ligand/receptor interactions or to initiate receptor-mediated signal transduction. Multiple members of the TNF-R superfamily are implicated in SLE. The classical ligand TNF-α interacts with two TNFRs, TNFRI (p55) and TNFRII (p75), both of which have been implicated in altered SLE disease activity (Davas et al., 1999). In addition, expression and cleavage of Fas, FasL (Tinazzi et al., 2009), and CD40L/CD154 (Desai-Mehta et al., 1996) are increased in SLE patients. BLyS and APRIL, key regulators of B cell survival and differentiation, are important SLE therapeutic targets (Dillon et al., 2010). In a study of 245 SLE patients followed for two years, with power to account for some confounding factors such as medications, increased BLyS levels associated with increased disease activity (Petri et al., 2008). Furthermore, a neutralizing anti-BLyS monoclonal antibody can reduce risk of disease flare over time (Espinosa et al., 2010), suggesting that BLyS may help regulate disease activity in some patients (Qin et al., 2011). However, their roles in ensuing disease flares are presently unknown.

SUMMARY OF THE INVENTION

Thus, in accordance with the present invention, there is provided a method of diagnosing a systemic lupus erythematosus (SLE) patient as undergoing a pre-flare event comprising (a) obtaining a blood, serum or plasma sample from a patient; and (b) assessing the level of at least one of each of the following: (i) innate type cytokine, (ii) Th1 type cytokine, (iii) Th2 type cytokine, and (iv) Th17 type cytokine, plus at least two each of the following: (i) a chemokines/adhesion molecules, (ii) a TNFR superfamily member, (iii) a regulatory mediator, and (iv) other mediators previously shown to play a role in SLE pathogenesis; and (c) diagnosing said patient as undergoing a pre-flare event when the majority of innate, Th1, Th2, Th17 type cytokines, chemokines/adhesion molecules, TNFR superfamily members and other SLE mediators are elevated and at least two regulatory mediators are reduced as compared to an SLE patient not undergoing a pre-flare event.

The innate type cytokines may be selected from IL-1α, IL-1β, IFN-α, IFN-β, G-CSF, IL-7, and IL-15. The Th1 type cytokine may be selected from IL-2, IL-12 and IFN-γ. The Th2 type cytokine may be selected from IL-4, IL-5 and IL-13. The Th17 type cytokine may be selected from IL-6, IL-17A, IL-21 and IL-23. Chemokines/adhesion molecules may be selected from IL-8, IP-10, RANTES, MCP-1, MCP-3, MIP-1α, MIP-1β, GRO-α, MIG, Eotaxin, ICAM-1, and E-selectin. TNFR superfamily members may be selected from TNF-α, TNFRI, TNFRII, TRAIL, Fas, FasL, BLyS, APRIL, and NGFβ. Other mediators previously shown to play a role in SLE pathogenesis may be selected from LIF, PAI-1, PDGF-BB, Leptin, SCF, and IL-2RA. Regulatory mediators may be selected from IL-10, TGF-β, SDF-1 and IL-1RA. Assessing may comprise immunologic detection, such as flow cytometry, ELISA, RIA or Western blot, or a multiplexed bead-based assay. Assessing may alternatively comprise detection of transcripts, such as that which comprises amplification of mRNA, including RT-PCR.

The method may further comprise performing one or more of a SELENA-SLEDA Index analysis on said patient, anti-dsDNA antibody (anti-dsDNA) testing in a sample from said patient and/or anti-extractable nuclear antigen (anti-ENA) in a sample from said patient. The method may further comprise taking a medical history of said patient. The method may further comprise treating said patient. The SLE patient not undergoing a flare event may be represented by a sample from the same patient during a non-flare period, or may be represented by a pre-determined average level.

In another embodiment, there is provided a method of assessing the efficacy of a treatment for systemic lupus erythematosus (SLE) in a patient comprising (a) obtaining a blood, serum or plasma sample from a patient; and (b) assessing the level of at least one of each of the following: (i) innate type cytokine, (ii) Th1 type cytokine, (iii) Th2 type cytokine, and (iv) Th17 type cytokine, plus at least two each of the following: (i) a chemokines/adhesion molecule, (ii) a TNFR superfamily member, (iii) a regulatory mediator, and (iv) other mediator previously shown to play a role in SLE pathogenesis; and (c) diagnosing said patient as undergoing a pre-flare event when the majority of innate, Th1, Th2, Th17 type cytokines, chemokines/adhesion molecules, TNFR superfamily members, and other SLE mediators are reduced and at least two regulatory mediators are elevated as compared to a level in a previous sample from said SLE patient.

The innate type cytokines may be selected from IL-1α, IL-1β, IFN-α, IFN-β, G-CSF, IL-7, and IL-15. The Th1 type cytokine may be selected from IL-2, IL-12 and IFN-γ. The Th2 type cytokine may be selected from IL-4, IL-5 and IL-13. The Th17 type cytokine may be selected from IL-6, IL-17A, IL-21 and IL-23. The chemokines/adhesion molecules may be selected from IL-8, IP-10, RANTES, MCP-1, MCP-3, MIP-1α, MIP-1β, GRO-α, MIG, Eotaxin, ICAM-1, and E-selectin. The TNFR superfamily members may be selected from TNF-α, TNFRI, TNFRII, TRAIL, Fas, FasL, BLyS, APRIL, and NGFβ. Other mediators previously shown to play a role in SLE pathogenesis may be selected from LIF, PAI-1, PDGF-BB, Leptin, SCF, and IL-2RA. Regulatory mediators may be selected from IL-10, TGF-β, SDF-1 and IL-1RA. Assessing may comprise immunologic detection, such as flow cytometry, ELISA, RIA or Western blot, or a multiplexed bead-based assay. Assessing may alternatively comprise detection of transcripts, such as that which comprises amplification of mRNA, including RT-PCR.

The method may further comprise performing one or more of a SLEDA Index analysis on said patient, anti-dsDNA antibody (anti-dsDNA) testing in a sample from said patient and/or anti-extractable nuclear antigen (anti-ENA) in a sample from said patient. The method may further comprise taking a medical history of said patient. The SLE patient not undergoing a flare event may be represented by a sample from the same patient during a non-flare period, or may be represented by a pre-determined average level.

Also provided is a kit comprising (a) one or more reagents for assessing the level of at least one of each of the following: innate type cytokine, Th1 type cytokine, Th2 type cytokine, and Th17 type cytokine, plus at least two each of the following: a chemokines/adhesion molecule, a TNFR superfamily member, a regulatory mediator, and other mediator previously shown to play a role in SLE pathogenesis; and (b) one or more reagents for assessing anti-dsDNA antibody (anti-dsDNA) testing and/or anti-extractable nuclear antigen (anti-ENA) in a biological sample.

The innate type cytokines may be selected from IL-1α, IL-1β, IFN-α, IFN-β, G-CSF, IL-7, and IL-15. The Th1 type cytokine may be selected from IL-2, IL-12 and IFN-γ. The Th2 type cytokine may be selected from IL-4, IL-5 and IL-13. The Th17 type cytokine may be selected from IL-6, IL-17A, IL-21 and IL-23. Chemokines/adhesion molecules may be selected from IL-8, IP-10, RANTES, MCP-1, MCP-3, MIP-1α, MIP-1β, GRO-α, MIG, Eotaxin, ICAM-1, and E-selectin. TNFR superfamily members may be selected from TNF-α, TNFRI, TNFRII, TRAIL, Fas, FasL, BLyS, APRIL, and NGFβ. Other mediators previously shown to play a role in SLE pathogenesis may be selected from LIF, PAI-1, PDGF-BB, Leptin, SCF, and IL-2RA. Regulatory mediators may be selected from IL-10, TGF-β, SDF-1 and IL-1RA. The reagents may be beads attached to binding ligands for each of said biomarkers.

As used herein the specification, "a" or "an" may mean one or more. As used herein in the claim(s), when used in conjunction with the word "comprising," the words "a" or "an" may mean one or more than one. As used herein "another" may mean at least a second or more. Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

FIGS. 7A-H. SLE patients with impending and concurrent disease flare have altered adaptive immunity and soluble TNF superfamily members compared to corresponding period of non-flare. Plasma Th1—(FIG. 7A, IL-12p70, IFNγ, and IL-2), Th2—(FIG. 7B, IL-5, IL-13, and IL-6), and Th17—(FIG. 7C, IL-23p19, IL-17A, and IL-21) type cytokines, as well as chemokines (FIG. 7D, IP-10, MCP-1, and MCP-3), soluble TNF superfamily members (FIG. 7E, TNF-α, TNFRI, TNFRII, Fas, FasL, and CD40L), regulatory mediators (FIG. 7F, IL-10, TGF-β, SDF-1), IL-RA/IL-1β balance (FIG. 7G, IL-1β, IL-1RA, and ratio of IL-1RA:IL-1β), and other inflammatory mediators (FIG. 7H, IL-1a, IL-8, ICAM-1, SCF, RANTES, and Resistin) (mean±SEM) were measured (mean±SEM) by xMAP® multiplex assay according to manufacturer protocol (Affymetrix, Santa Clara, Calif.) and read on a Bio-plex 200 LUMINEX®-type reader (Bio-Rad, Hercules, Calif.). Samples were procured at baseline (BL)/pre-vaccination (circle) from 13 EA SLE patients who exhibited disease flare (black symbol) 6-12 weeks later (follow-up (FU), square) vs. the same SLE patients in a separate influenza season when they did not exhibit disease flare post-vaccination (SNF, red symbol) vs. age (±5 years)/race/gender/time of sample procurement matched unrelated/unaffected healthy controls (HC, open symbol). Significance determined by Friedman test with Dunn's multiple comparison (Friedman test significance listed under each title). *p<0.05, p<0.01, *p<0.001, ****p, 0.0001

FIGS. 8A-C. Higher Soluble Mediator Scores in SLE patients with impending flare. Soluble Mediator Scores from baseline (pre-vaccination) plasma levels were determined for each SLE patient who exhibited disease flare within the following 12 weeks relative to (FIG. 8A) a demographically matched SLE patient who did not exhibit disease flare (NF, p<0.0001 by Wilcoxon matched-pairs test) or (FIG. 8B) the same SLE patient in a separate year of the study with no observed disease flare (SNF, p=0.002 by Wilcoxon matched-pairs test). Data presented as column (mean±SD) and Box and Whisker (median±max and min) graphs. (FIG. 8C) Soluble Mediator Scores for each SLE patient were compared between year of impending disease flare (Flare) and year of non-flare (SNF) in FIG. 8B.

FIGS. 9A-G. Increased adaptive immunity pathways and soluble TNF superfamily members, and decreased levels of regulatory mediators, in confirmatory group of SLE patients with impending flare. Plasma was procured at baseline from 13 SLE patients who exhibited disease flare 6 to 12 weeks later (black bar) and 13 demographically matched SLE patients who did not exhibit flare (NF, stripped bar). Levels of Th1 (FIG. 9A), Th2 (FIG. 9B), and Th17 (FIG. 9C) type cytokines, as well as chemokines (FIG. 9D), soluble TNF superfamily members (FIG. 9E), regulatory mediators (FIG. 9F), and IL-1RA:IL-1β ratio (FIG. 9G) in 56 EA SLE patients (mean±SEM) were measured. Significance was determined by Wilcoxon matched-pairs test. *p<0.05, p<0.01, *p<0.001, ****p, 0.0001

FIGS. 10A-G. A confirmatory group of SLE patients have altered baseline mediators in adaptive immunity pathways and soluble TNF superfamily members during pre-flare periods compared to the same patients during non-flare periods. Plasma was procured at baseline from 18 SLE patients who exhibited disease flare 6 to 12 weeks later (black bar) and from the same patients in a separate year of the study when they did not exhibit disease flare (SNF, gray bar). Plasma Th1 (FIG. 10A), Th2 (FIG. 10B), and Th17 (FIG. 10C) type cytokines, as well as chemokines (FIG. 10D), soluble TNF superfamily members (FIG. 10E), regulatory mediators (FIG. 10F), and IL-1RA:IL-1β ratio (FIG. 10 FIG. 10G) were measured (mean±SEM). Significance was determined by Wilcoxon matched-pairs test. *p<0.05, p<0.01, *p<0.001, ****p, 0.0001

FIGS. 11A-B. Soluble mediators of inflammation in a confirmatory group of SLE patients which are elevated compared to healthy controls which may or may not discriminate between impending disease flare and non-flare. Plasma levels of BLyS, APRIL, IL-15, IL-2Rα, MIG, MIP-1α, and MIP-1β were measured and compared between (FIG. 11A) 13 pre-flare SLE patients (black bar), 13 matched non-flare SLE patients (NF, striped bar), and 13 matched healthy controls (HC, white bar) or (FIG. 11B) 18 SLE patients during a pre-flare period (black bar), the same SLE patients during a non-flare period (SNF, gray bar), and 18 matched healthy controls (HC, white bar). Data are shown as mean±SEM; significance between SLE patients (Flare and NF/SNF) and HC was determined by Wilcoxon matched-pairs test. *p<0.05, p<0.01, *p<0.001, ****p, 0.0001

FIGS. 12A-C. Higher Soluble Mediator Scores in a confirmatory group of SLE patients with impending flare. Soluble Mediator Scores from baseline (pre-vaccination) plasma levels were determined for each SLE patient who exhibited disease flare within the following 12 weeks relative to (FIG. 12A) a demographically matched SLE patient who did not exhibit disease flare (NF, p<0.0001 by Wilcoxon matched-pairs test; 13 pre-flare SLE patients vs. 13 matched non-flare SLE patients) or (FIG. 12B) the same SLE patient in a separate year of the study with no observed disease flare (SNF, p=0.002 by Wilcoxon matched-pairs test, n=18). Data presented as Box and Whisker (median±max and min) graphs. (FIG. 12C) Soluble Mediator Scores for each SLE patient were compared between year of impending disease flare (Flare) and year of non-flare (SNF) in FIG. 12B.

FIGS. 13A-H. Altered adaptive immunity and soluble TNF superfamily members in confirmatory group of SLE patients with impending and concurrent disease flare. Plasma Th1 (FIG. 13A, IL-12p70, IFN-γ, and IL-2), Th2 (FIG. 13B, IL-5, IL-13, and IL-6), and Th17 (FIG. 13C, IL-23p19, IL-17A, and IL-21) type cytokines, as well as chemokines (FIG. 13D, IP-10, MCP-1, and MCP-3), soluble TNF superfamily members (FIG. 13E, TNF-α, TNFRI, TNFRII, Fas, FasL, and CD40L), regulatory mediators (FIG. 13F, IL-10, TGF-β, SDF-1), IL-RA/IL-10 balance (FIG. 13G, IL-1b, IL-1RA, and ratio of IL-1RA:IL-1β), and other inflammatory mediators (FIG. 13H, IFN-α, IFN-β, IL-1α, ICAM-1, SCF, and Eselectin) (mean±SEM) were measured (mean±SEM) by xMAP® multiplex assay according to manufacturer protocol (eBioscience/Affymetrix, Santa Clara, Calif.) and read on a Bio-plex 200 reader (Bio-Rad, Hercules, Calif.). Samples were procured at baseline (BL)/pre-vaccination (circle) from 13 SLE patients who exhibited disease flare (black symbol) 6 to 12 weeks later (follow-up [FU], square) vs. 13 age (±5 years)/race/gender/time of sample procurement matched SLE patients who did not flare (NF, blue symbol) vs. 13 age (±5 years)/race/gender/time of sample procurement matched unrelated/unaffected healthy controls (HC, open symbol). Significance determined by Friedman test with Dunn's multiple comparison (Friedman test significance listed under each title). *p<0.05, p<0.01, *p<0.001, ****p, 0.0001.

FIGS. 14A-H. A confirmatory group of SLE patients with impending and concurrent disease flare have altered adaptive immunity and soluble TNF superfamily members compared to corresponding period of non-flare. Plasma Th1 (FIG. 14A, IL-12p70, IFN-γ, and IL-2), Th2 (FIG. 14B, IL-5, IL-13, and IL-6), and Th17 (FIG. 14C, IL-23p19, IL-17A, and IL-21) type cytokines, as well as chemokines (D, IP-10, MCP-1, and MCP-3), soluble TNF superfamily members (FIG. 14E, TNF-α, TNFRI, TNFRII, Fas, FasL, and CD40L), regulatory mediators (FIG. 14F, IL-10, TGF-β, SDF-1), IL-RA/IL-1β balance (FIG. 14G, IL-1b, IL-1RA, and ratio of IL-1RA:IL-1β), and other inflammatory mediators (FIG. 14H, IFN-α, IFN-β, IL-1α, ICAM-1, SCF, and Eselectin) (mean±SEM) were measured (mean±SEM) by xMAP® multiplex assay according to manufacturer protocol (eBioscience/Affymetrix, Santa Clara, Calif.) and read on a Bio-plex 200 LUMINEX®-type reader (Bio-Rad, Hercules, Calif.). Samples were procured at baseline (BL)/pre-vaccination (circle) from 18 SLE patients who exhibited disease flare (black symbol) 6-12 weeks later (follow-up [FU], square) vs. the same SLE patients in a separate influenza season when they did not exhibit disease flare post-vaccination (SNF, red symbol) vs. 18 age (±5 years)/race/gender/time of sample procurement matched unrelated/unaffected healthy controls (HC, open symbol). Significance determined by Friedman test with Dunn's multiple comparison (Friedman test significance listed under each title). *p<0.05, p<0.01, *p<0.001, ****p, 0.0001

DESCRIPTION OF ILLUSTRATIVE EMBODIMENTS

Figure 1:
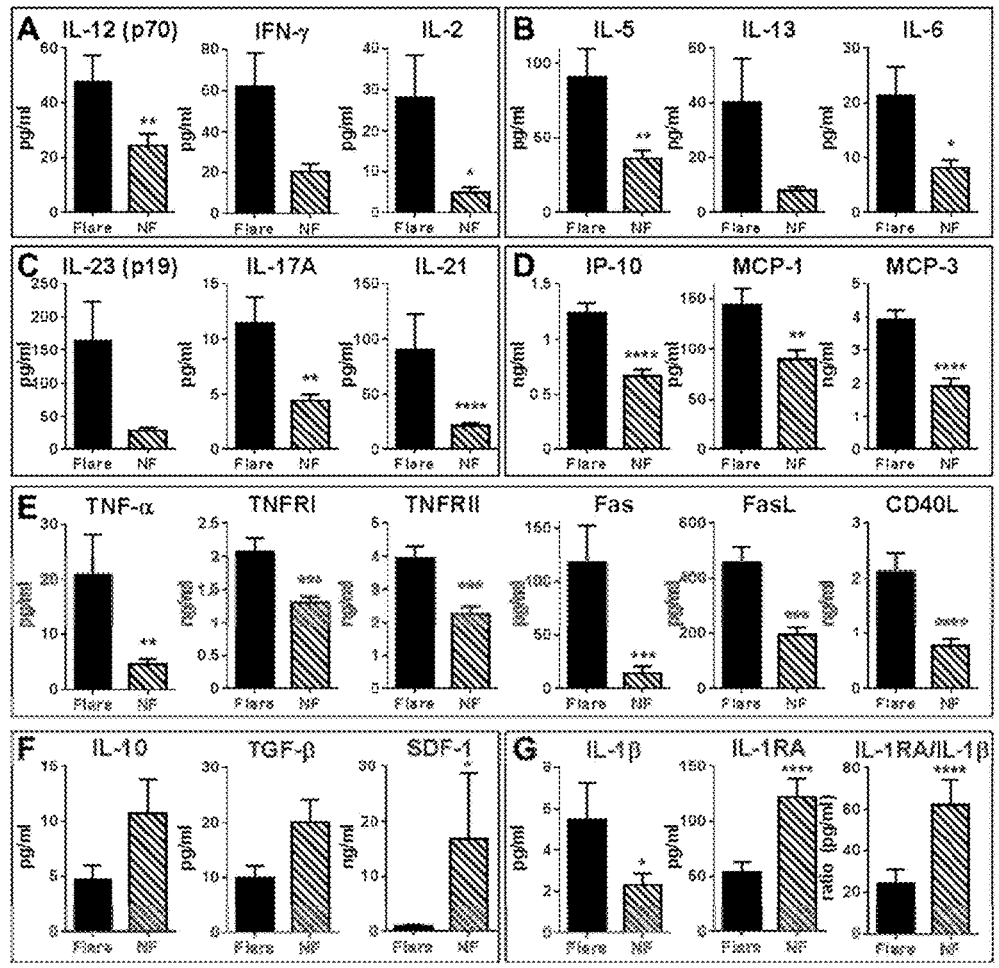
FIGS. 1A-G. Increased adaptive immunity pathways and soluble TNF superfamily members, and decreased levels of regulatory mediators, in SLE patients with impending flare. Plasma was procured at baseline from SLE patients who exhibited disease flare 6 to 12 weeks later (black bar) and demographically matched SLE patients who did not exhibit flare (NF, striped bar). Levels of Th1—(FIG. 1A), Th2—(FIG. 1B), and Th17—(FIG. 1C) type cytokines, as well as chemokines (FIG. 1D), soluble TNF superfamily members (FIG. 1E), regulatory mediators (FIG. 1F), and IL-1RA:IL-1β ratio (FIG. 1G) in 28 EA SLE patients (mean±SEM) were measured. Significance was determined by Wilcoxon matched-pairs test. *$p<0.05$, $p<0.01$, *$p<0.001$, ****$p, 0.0001$.

Here, the inventors report studies of the inflammatory and regulatory pathways potentially dysregulated early in lupus flare, even before clinical symptoms are reported. Plasma and clinical data were evaluated from SLE patients and matched, healthy controls participating in the SLE Influenza Vaccination Cohort (Crowe et al., 2011). Using an xMAP® multiplex and ELISA approaches, European-American (EA) SLE patients with impending disease flare 6 or 12 weeks after vaccination were found to have increased pre-flare inflammatory adaptive cytokines, chemokines, and shed TNFR superfamily members, with decreased regulatory mediators of inflammation, compared to matched patients with stable disease. These results enabled the development of a combined soluble mediator score that reflects pre-flare immune status in SLE patients who go on to flare. These and other aspects of the disclosure are described in greater detail below.

I. SYSTEMIC LUPUS ERYTHEMATOSUS

A. Disease Manifestations

Systemic lupus erythematosus (SLE) is a systemic autoimmune disease (or autoimmune connective tissue disease) that can affect any part of the body. The disease occurs nine times more often in women than in men, especially in women in child-bearing years ages 15 to 35, and is also more common in those of non-European descent.

As occurs in other autoimmune diseases, the immune system attacks the body's cells and tissue, resulting in inflammation and tissue damage. SLE can induce abnormalities in the adaptive and innate immune system, as well as mount Type III hypersensitivity reactions in which antibody-immune complexes precipitate and cause a further immune response. SLE most often damages the joints, skin, lungs, heart, blood components, blood vessels, kidneys, liver and nervous system. The course of the disease is unpredictable, often with periods of increased disease activity (called "flares") alternating with suppressed or decreased disease activity. A flare has been defined as a measurable increase in disease activity in one or more organ systems involving new or worse clinical signs and symptoms and/or laboratory measurements. It must be considered clinically significant by the assessor and usually there would be at least consideration of a change or an increase in treatment (Ruperto et al., 2010).

SLE has no cure, and leads to increased morbidity and early mortality in many patients. The most common causes of death in lupus patients include accelerated cardiovascular disease (likely associated with increased inflammation and perhaps additionally increased by select lupus therapies), complications from renal involvement and infections. Survival for people with SLE in the United States, Canada, and Europe has risen to approximately 95% at five years, 90% at 10 years, and 78% at 20 years in patients of European descent; however, similar improvements in mortality rates in non-Caucasian patients are not as evident. Childhood systemic lupus erythematosus generally presents between the ages of 3 and 15, with girls outnumbering boys 4:1, and typical skin manifestations being butterfly eruption on the face and photosensitivity.

SLE is one of several diseases known as "the great imitators" because it often mimics or is mistaken for other illnesses. SLE is a classical item in differential diagnosis, because SLE symptoms vary widely and come and go unpredictably. Diagnosis can thus be elusive, with some people suffering unexplained symptoms of untreated SLE for years. Common initial and chronic complaints include fever, malaise, joint pains, myalgias, fatigue, and temporary loss of cognitive abilities. Because they are so often seen with other diseases, these signs and symptoms are not part of the American College of Rheumatology SLE classification criteria. When occurring in conjunction with other signs and symptoms (see below), however, they are suggestive.

The most common clinical symptom which brings a patient for medical attention is joint pain, with the small joints of the hand and wrist usually affected, although nearly all joints are at risk. Between 80 and 90% of those affected will experience joint and/or muscle pain at some time during the course of their illness. Unlike rheumatoid arthritis, many lupus arthritis patients will have joint swelling and pain, but no X-ray changes and minimal loss of function. Fewer than 10% of people with lupus arthritis will develop deformities of the hands and feet. SLE patients are at particular risk of developing articular tuberculosis. An association between osteoporosis and SLE has been found, and SLE may be associated with an increased risk of bone fractures in relatively young women.

Over half (65%) of SLE sufferers have some dermatological manifestations at some point in their disease, with approximately 30% to 50% suffering from the classic malar rash (or butterfly rash) associated with the name of the disorder. Some may exhibit chronic thick, annual scaly patches on the skin (referred to as discoid lupus). Alopecia, mouth ulcers, nasal ulcers, and photosensitive lesions on the skin are also possible manifestations. Anemia may develop in up to 50% of lupus cases. Low platelet and white blood cell counts may be due to the disease or as a side effect of pharmacological treatment. People with SLE may have an association with antiphospholipid antibody syndrome (a thrombotic disorder), wherein autoantibodies to phospholipids are present in their serum. Abnormalities associated with antiphospholipid antibody syndrome include a paradoxical prolonged partial thromboplastin time (which usually occurs in hemorrhagic disorders) and a positive test for antiphospholipid antibodies; the combination of such findings has earned the term "lupus anticoagulant-positive." SLE patients with anti-phospholipid autoantibodies have more ACR classification criteria of the disease and may suffer from a more severe lupus phenotype.

A person with SLE may have inflammation of various parts of the heart, such as pericarditis, myocarditis, and endocarditis. The endocarditis of SLE is characteristically noninfective (Libman-Sacks endocarditis), and involves either the mitral valve or the tricuspid valve. Atherosclerosis also tends to occur more often and advances more rapidly than in the general population. Lung and pleura inflammation can cause pleuritis, pleural effusion, lupus pneumonitis, chronic diffuse interstitial lung disease, pulmonary hypertension, pulmonary emboli, pulmonary hemorrhage, and shrinking lung syndrome.

Painless hematuria or proteinuria may often be the only presenting renal symptom. Acute or chronic renal impairment may develop with lupus nephritis, leading to acute or end-stage renal failure. Because of early recognition and management of SLE, end-stage renal failure occurs in less than 5% of cases. A histological hallmark of SLE is membranous glomerulonephritis with "wire loop" abnormalities. This finding is due to immune complex deposition along the glomerular basement membrane, leading to a typical granular appearance in immunofluorescence testing.

Neuropsychiatric syndromes can result when SLE affects the central or peripheral nervous systems. The American College of Rheumatology defines 19 neuropsychiatric syndromes in systemic lupus erythematosus. The diagnosis of neuropsychiatric syndromes concurrent with SLE is one of the most difficult challenges in medicine, because it can involve so many different patterns of symptoms, some of which may be mistaken for signs of infectious disease or stroke. The most common neuropsychiatric disorder people with SLE have is headache, although the existence of a specific lupus headache and the optimal approach to headache in SLE cases remains controversial. Other common neuropsychiatric manifestations of SLE include cognitive dysfunction, mood disorder (including depression), cerebrovascular disease, seizures, polyneuropathy, anxiety disorder, cerebritis, and psychosis. CNS lupus can rarely present with intracranial hypertension syndrome, characterized by an elevated intracranial pressure, papilledema, and headache with occasional abducens nerve paresis, absence of a space-occupying lesion or ventricular enlargement, and normal cerebrospinal fluid chemical and hematological constituents. More rare manifestations are acute confusional state, Guillain-Barré syndrome, aseptic meningitis, autonomic disorder, demyelinating syndrome, mononeuropathy (which might manifest as mononeuritis multiplex), movement disorder (more specifically, chorea), myasthenia gravis, myelopathy, cranial neuropathy and plexopathy. Neural symptoms contribute to a significant percentage of morbidity and mortality in patients with lupus. As a result, the neural side of lupus is being studied in hopes of reducing morbidity and mortality rates. The neural manifestation of lupus is known as neuropsychiatric systemic lupus erythematosus (NPSLE). One aspect of this disease is severe damage to the epithelial cells of the blood-brain barrier.

SLE causes an increased rate of fetal death in utero and spontaneous abortion (miscarriage). The overall live-birth rate in SLE patients has been estimated to be 72%. Pregnancy outcome appears to be worse in SLE patients whose disease flares up during pregnancy. Neonatal lupus is the occurrence of SLE symptoms in an infant born from a mother with SLE, most commonly presenting with a rash resembling discoid lupus erythematosus, and sometimes with systemic abnormalities such as heart block or hepatosplenomegaly. Neonatal lupus is usually benign and self-limited.

Fatigue in SLE is probably multifactorial and has been related to not only disease activity or complications such as anemia or hypothyroidism, but also to pain, depression, poor sleep quality, poor physical fitness and lack of social support.

Different clinical measurements have been used to determine whether a SLE patients is having a clinic flare. One of the most common measurements is the Systemic Lupus Erythematosus Disease Activity Index SELENA Modification (world-wide-web at rheumatology.org/Practice/Clinical/Indexes/Systemic_Lupus_Erythematosus_Disease_Activity_Index_SELENA_Modification/). This scale uses a point system to calculate when the accumulated significance of recent changes in various indicators translates into a mild/moderate (SELENA-SLEDA Index of 3-11 point change) or a severe (12 of more point change) flare. Although helpful in defining clinical flares in therapeutic and observational SLE clinical trials, this information only defines a flare state and does not help predict or identify patients who likely have an impending flare (an important clinical problem). In addition, no consensus, objective molecular test or tests are consistently associated individually with increased disease activity, nor with imminent SLE disease flare. Having such a molecular test would be greatly beneficial to SLE clinical care to help guide therapy, prevent damage, and minimize therapeutic toxicity.

B. Diagnosis

Antinuclear antibody (ANA) testing, anti-dsDNA, and anti-extractable nuclear antigen (anti-ENA) responses form the mainstay of SLE serologic testing. Several techniques are used to detect ANAs (Lu et al., 2012; Bruner et al., 2012). Clinically the most widely used method is indirect immunofluorescence. The pattern of fluorescence suggests the type of antibody present in the patient's serum. Direct immunofluorescence can detect deposits of immunoglobulins and complement proteins in the patient's skin. When skin not exposed to the sun is tested, a positive direct IF (the so-called Lupus band test) is an evidence of systemic lupus erythematosus.

ANA screening yields positive results in many connective tissue disorders and other autoimmune diseases, and may occur in healthy individuals. Subtypes of antinuclear antibodies include anti-Smith and anti-double stranded DNA (dsDNA) antibodies (which are linked to SLE) and anti-histone antibodies (which are linked to drug-induced lupus). Anti-dsDNA antibodies are relatively specific for SLE; they are present in up to 50% of cases depending on ethnicity, whereas they appear in less than 2% of people without SLE. The anti-dsDNA antibody titers also tend to reflect disease activity, although not in all cases. Other ANA that may occur in SLE sufferers are anti-U1 RNP (which also appears in systemic sclerosis), anti-Ro (or anti-SSA) and anti-La (or anti-SSB; both of which are more common in Sjögren's syndrome). Anti-Ro and anti-La, when present in the maternal circulation, confer an increased risk for heart conduction block in neonatal lupus. Other tests routinely performed in suspected SLE are complement system levels (low levels suggest consumption by the immune system), electrolytes and renal function (disturbed if the kidneys are involved), liver enzymes, urine tests (proteinuria, hematuria, pyuria, and casts), and complete blood count.

II. BIOMARKERS FOR SLE FLARES

A. Flare Markers

Innate Cytokines.

Innate cytokines are mediators secreted in response to immune system danger signals, such as toll like receptors (TLR). Innate cytokines which activate and are secreted by multiple immune cell types include Type I interferons (INF-α and IFN-β), TNF-α, and members of the IL-1 family (IL-1α and IL-1β). Other innate cytokines, secreted by antigen presenting cells (APC), including dendritic cells, macrophages, and B-cells, as they process and present protein fragments (antigens, either from infectious agents or self proteins that drive autoimmune disease) to CD4 T-helper (Th) cells, drive the development of antigen specific inflammatory pathways during the adaptive response, described below.

Th1-Type Cytokines.

Th1-type cytokines drive proinflammatory responses responsible for killing intracellular parasites and for perpetuating autoimmune responses. Excessive proinflammatory responses can lead to uncontrolled tissue damage, particularly in systemic lupus erythematosus (SLE).

CD4 Th cells differentiate to Th-1 type cells upon engagement of APC, co-stimulatory molecules, and APC-secreted cytokines, the hallmark of which is IL-12. IL-12 is composed of a bundle of four alpha helices. It is a heterodimeric cytokine encoded by two separate genes, IL-12A (p35) and IL-12B (p40). The active heterodimer, and a homodimer of p40, are formed following protein synthesis. IL-12 binds to the heterodimeric receptor formed by IL-12R-β1 and IL-12R-β2. IL-12R-β2 is considered to play a key role in IL-12 function, as it is found on activated T cells and is stimulated by cytokines that promote Th1 cell development and inhibited by those that promote Th2 cell development. Upon binding, IL-12R-β2 becomes tyrosine phosphorylated and provides binding sites for kinases, Tyk2 and Jak2. These are important in activating critical transcription factor proteins such as STAT4 that are implicated in IL-12 signaling in T cells and NK cells. IL-12 mediated signaling results in the production of interferon-gamma (IFN-γ) and tumor necrosis factor-alpha (TNF-α) from T and natural killer (NK) cells, and reduces IL-4 mediated suppression of IFN-γ.

IFNγ, or type II interferon, consists of a core of six α-helices and an extended unfolded sequence in the C-terminal region. IFNγ is critical for innate (NK cell) and adaptive (T cell) immunity against viral (CD8 responses) and intracellular bacterial (CD4 Th1 responses) infections and for tumor control. During the effector phase of the immune response, IFNγ activates macrophages. Aberrant IFNγ expression is associated with a number of autoinflammatory and autoimmune diseases, including increased disease activity in SLE.

Although IFNγ is considered to be the characteristic Th1 cytokine, in humans, interleukin-2 (IL-2) has been shown to influence Th1 differentiation, as well as its role as the predominant cytokine secreted during a primary response by naïve Th cells. IL-2 is necessary for the growth, proliferation, and differentiation of T cells to become 'effector' T cells. IL-2 is normally produced by T cells during an immune response. Antigen binding to the T cell receptor (TCR) stimulates the secretion of IL-2, and the expression of IL-2 receptors IL-2R. The IL-2/IL-2R interaction then stimulates the growth, differentiation and survival of antigen-specific CD4+ T cells and CD8+ T cells As such, IL-2 is necessary for the development of T cell immunologic memory, which depends upon the expansion of the number and function of antigen-selected T cell clones. IL-2, along with IL-7 and IL-15 (all members of the common cytokine receptor gamma-chain family), maintain lymphoid homeostasis to ensure a consistent number of lymphocytes during cellular turnover.

Th2-Type Cytokines.

Th2-type cytokines include IL-4, IL-5, IL-13, as well as IL-6 (in humans), and are associated with the promotion of B-lymphocyte activation, antibody production, and isotype switching to IgE and eosinophilic responses in atopy. In excess, Th2 responses counteract the Th1 mediated microbicidal action. Th2-type cytokines may also contribute to SLE pathogenesis and increased disease activity.

IL-4 is a 15-kD polypeptide with multiple effects on many cell types. Its receptor is a heterodimer composed of an a subunit, with IL-4 binding affinity, and the common γ subunit which is also part of other cytokine receptors. In T cells, binding of IL-4 to its receptor induces proliferation and differentiation into Th2 cells. IL-4 also contributes to the Th2-mediated activation of B-lymphocytes, antibody production, and, along with IL-5 and IL-13, isotype switching away from Th1-type isotypes (including IgG1 and IgG2) toward Th2-type isotypes (including IgG4, and IgE that contributes to atopy). In addition to its contributions to Th2 biology, IL-4 plays a significant role in immune cell hematopoiesis, with multiple effects on hematopoietic progenitors, including proliferation and differentiation of committed as well as primitive hematopoietic progenitors. It acts synergistically with granulocyte-colony stimulating factor (G-CSF) to support neutrophil colony formation, and, along with IL-1 and IL-6, induces the colony formation of human bone marrow B lineage cells.

IL-5 is an interleukin produced by multiple cell types, including Th2 cells, mast cells, and eosinophils. IL-5 expression is regulated by several transcription factors including GATA3. IL-5 is a 115-amino acid (in human; 133 in the mouse)-long TH2 cytokine that is part of the hematopoietic family. Unlike other members of this cytokine family (namely IL-3 and GM-CSF), this glycoprotein in its active form is a homodimer. Through binding to the IL-5 receptor, IL-5 stimulates B cell growth and increases immunoglobulin secretion. IL-5 has long been associated with the cause of several allergic diseases including allergic rhinitis and asthma, where mast cells play a significant role, and a large increase in the number of circulating, airway tissue, and induced sputum eosinophils have been observed.

Given the high concordance of eosinophils and, in particular, allergic asthma pathology, it has been widely speculated that eosinophils have an important role in the pathology of this disease. IL-13 is secreted by many cell types, but especially Th2 cells as a mediator of allergic inflammation and autoimmune disease, including type 1 diabetes mellitus, rheumatoid arthritis (RA) and SLE. IL-13 induces its effects through a multi-subunit receptor that includes the alpha chain of the IL-4 receptor (IL-4Rα) and at least one of two known IL-13-specific binding chains. Most of the biological effects of IL-13, like those of IL-4, are linked to a single transcription factor, signal transducer and activator of transcription 6 (STAT6).

Like IL-4, IL-13 is known to induce changes in hematopoietic cells, but to a lesser degree. IL-13 can induce immunoglobulin E (IgE) secretion from activated human B cells. IL-13 induces many features of allergic lung disease, including airway hyperresponsiveness, goblet cell metaplasia and mucus hypersecretion, which all contribute to airway obstruction. IL-4 contributes to these physiologic changes, but to a lesser extent than IL-13. IL-13 also induces secretion of chemokines that are required for recruitment of allergic effector cells to the lung.

IL-13 may antagonize Th1 responses that are required to resolve intracellular infections and induces physiological changes in parasitized organs that are required to expel the offending organisms or their products. For example, expulsion from the gut of a variety of mouse helminths requires IL-13 secreted by Th2 cells. IL-13 induces several changes in the gut that create an environment hostile to the parasite, including enhanced contractions and glycoprotein hypersecretion from gut epithelial cells, that ultimately lead to detachment of the organism from the gut wall and their removal.

Interleukin 6 (IL-6) is secreted by multiple cell types and participates in multiple innate and adaptive immune response pathways. IL-6 mediates its biological functions through a signal-transducing component of the IL-6 receptor (IL-6R), gp130, that leads to tyrosine kinase phosphorylation and downstream signaling events, including the STAT1/3 and the SHP2/ERK cascades. IL-6 is a key mediator of fever and stimulates an acute phase response during infection and after trauma. It is capable of crossing the blood brain barrier and initiating synthesis of $PGE_2$ in the hypothalamus, thereby changing the body's temperature setpoint. In muscle and fatty tissue, IL-6 stimulates energy mobilization which leads to increased body temperature.

IL-6 can be secreted by multiple immune cells in response to specific microbial molecules, referred to as pathogen associated molecular patterns (PAMPs). These PAMPs bind to highly important group of detection molecules of the innate immune system, called pattern recognition receptors (PRRs), including Toll-like receptors (TLRs). These are present on the cell surface and intracellular compartments and induce intracellular signaling cascades that give rise to inflammatory cytokine production. As a Th2-type cytokine in humans, IL-6, along with IL-4, IL-5, and IL-13, can influence IgE production and eosinophil airway infiltration in asthma. IL-6 also contributes to Th2-type adaptive immunity against parasitic infections, with particular importance in mast-cell activation that coincides with parasite expulsion.

IL-6 is also a Th17-type cytokine, driving IL-17 production by T-lymphocytes in conjunction with TGF-β. IL-6 sensitizes Th17 cells to IL-23 (produced by APC) and IL-21 (produced by T-lymphocytes to perpetuate the Th17 response. Th17-type responses are described below.

Th17-Type Cytokines.

Th17 cells are a subset of T helper cells are considered developmentally distinct from Th1 and Th2 cells and excessive amounts of the cell are thought to play a key role in autoimmune disease, such as multiple sclerosis (which was previously thought to be caused solely by Th1 cells), psoriasis, autoimmune uveitis, Crohn's disease, type 2 diabetes mellitus, rheumatoid arthritis, and SLE. Th17 are thought to play a role in inflammation and tissue injury in these conditions. In addition to autoimmune pathogenesis, Th17 cells serve a significant function in anti-microbial immunity at epithelial/mucosal barriers. They produce cytokines (such as IL-21 and IL-22) that stimulate epithelial cells to produce anti-microbial proteins for clearance of microbes such as Candida and Staphylococcus species. A lack of Th17 cells may leave the host susceptible to opportunistic infections. In addition to its role in autoimmune disease and infection, the Th17 pathway has also been implicated in asthma, including the recruitment of neutrophils to the site of airway inflammation.

Interleukin 17A (IL-17A), is the founding member of a group of cytokines called the IL-17 family. Known as CTLA8 in rodents, IL-17 shows high homology to viral IL-17 encoded by an open reading frame of the T-lymphotropic rhadinovirus Herpesvirus saimiri. IL-17A is a 155-amino acid protein that is a disulfide-linked, homodimeric, secreted glycoprotein with a molecular mass of 35 kDa. Each subunit of the homodimer is approximately 15-20 kDa. The structure of IL-17A consists of a signal peptide of 23 amino acids followed by a 123-residue chain region characteristic of the IL-17 family. An N-linked glycosylation site on the protein was first identified after purification of the protein revealed two bands, one at 15 KDa and another at 20 KDa. Comparison of different members of the IL-17 family revealed four conserved cysteines that form two disulfide bonds. IL-17A is unique in that it bears no resemblance to other known interleukins. Furthermore, IL-17A bears no resemblance to any other known proteins or structural domains.

The crystal structure of IL-17F, which is 50% homologous to IL-17A, revealed that IL-17F is structurally similar to the cysteine knot family of proteins that includes the neurotrophins. The cysteine knot fold is characterized by two sets of paired β-strands stabilized by three disulfide interactions. However, in contrast to the other cysteine knot proteins, IL-17F lacks the third disulfide bond. Instead, a serine replaces the cysteine at this position. This unique feature is conserved in the other IL-17 family members. IL-17F also dimerizes in a fashion similar to nerve growth factor (NGF) and other neurotrophins.

IL-17A acts as a potent mediator in delayed-type reactions by increasing chemokine production in various tissues to recruit monocytes and neutrophils to the site of inflammation, similar to IFNγ. IL-17A is produced by T-helper cells and is induced by APC production of IL-6 (and TGF-β) and IL-23, resulting in destructive tissue damage in delayed-type reactions. IL-17 as a family functions as a proinflammatory cytokine that responds to the invasion of the immune system by extracellular pathogens and induces destruction of the pathogen's cellular matrix. IL-17 acts synergistically with TNF-α and IL-1. To elicit its functions, IL-17 binds to a type I cell surface receptor called IL-17R of which there are at least three variants IL17RA, IL17RB, and IL17RC.

IL-23 is produced by APC, including dendritic cells, macrophages, and B cells. The IL-23A gene encodes the p19 subunit of the heterodimeric cytokine. IL-23 is composed of this protein and the p40 subunit of IL-12. The receptor of IL-23 is formed by the beta 1 subunit of IL12 (IL12RB1) and an IL23 specific subunit, IL23R. While IL-12 stimulates IFNγ production via STAT4, IL-23 primarily stimulates IL-17 production via STAT3 in conjunction with IL-6 and TGF-β.

IL-21 is expressed in activated human CD4$^+$ T cells, most notably Th17 cells and T follicular helper (Tfh) cells. IL-21 is also expressed in NK T cells. IL-21 has potent regulatory effects on cells of the immune system, including natural killer (NK) cells and cytotoxic T cells that can destroy virally infected or cancerous cells. This cytokine induces cell division/proliferation in its target cells.

The IL-21 receptor (IL-21R) is expressed on the surface of T, B and NK cells. Belonging to the common cytokine receptor gamma-chain family, IL-21R requires dimerization with the common gamma chain (γc) in order to bind IL-21. When bound to IL-21, the IL-21 receptor acts through the Jak/STAT pathway, utilizing Jak1 and Jak3 and a STAT3 homodimer to activate its target genes.

IL-21 may be a critical factor in the control of persistent viral infections. IL-21 (or IL-21R) knock-out mice infected with chronic LCMV (lymphocytic choriomeningitis virus) were not able to overcome chronic infection compared to normal mice. Besides, these mice with impaired IL-21 signaling had more dramatic exhaustion of LCMV-specific CD8+ T cells, suggesting that IL-21 produced by CD4+ T cells is required for sustained CD8+ T cell effector activity and then, for maintaining immunity to resolve persistent viral infection. Thus, IL-21 may contribute to the mechanism by which CD4+ T helper cells orchestrate the immune system response to viral infections.

In addition to promoting Th17 responses that contribute to chronic inflammation and tissue damage in autoimmune disease, IL-21 induces Tfh cell formation within the germinal center and signals directly to germinal center B cells to sustain germinal center formation and its response. IL-21 also induces the differentiation of human naïve and memory B cells into antibody secreting cells, thought to play a role in autoantibody production in SLE.

Chemokines and Adhesion Molecules.

Chemokines and adhesion molecules (in this case, ICAM-1 and E-selectin) serve to coordinate cellular traffic within the immune response. Chemokines are divided into CXC (R)eceptor/CXC (L)igand and CCR/CCL subgroups.

GROα, also known as Chemokine (C—X—C motif) ligand 1 (CXCL1) is belongs to the CXC chemokine family that was previously called GRO1 oncogene, KC, Neutrophil-activating protein 3 (NAP-3) and melanoma growth stimulating activity, alpha (MSGA-α). In humans, this protein is encoded by the CXCL1 gene on chromosome 4. CXCL1 is expressed by macrophages, neutrophils and epithelial cells, and has neutrophil chemoattractant activity. GROα is involved in the processes of angiogenesis, inflammation, wound healing, and tumorigenesis. This chemokine elicits its effects by signaling through the chemokine receptor CXCR2.

Interleukin 8 (IL-8)/CXCL8 is a chemokine produced by macrophages and other cell types such as epithelial cells, airway smooth muscle cells and endothelial cells. In humans, the interleukin-8 protein is encoded by the IL8 gene. IL-8 is a member of the CXC chemokine family. The genes encoding this and the other ten members of the CXC chemokine family form a cluster in a region mapped to chromosome 4q.

There are many receptors of the surface membrane capable to bind IL-8; the most frequently studied types are the G protein-coupled serpentine receptors CXCR1, and CXCR2, expressed by neutrophils and monocytes. Expression and affinity to IL-8 is different in the two receptors (CXCR1>CXCR2). IL-8 is secreted and is an important mediator of the immune reaction in the innate immunity in response to TLR engagement. During the adaptive immune response, IL-8 is produced during the effector phase of Th1 and Th17 pathways, resulting in neutrophil and macrophage recruitment to sites of inflammation, including inflammation during infection and autoimmune disease. While neutrophil granulocytes are the primary target cells of IL-8, there are a relative wide range of cells (endothelial cells, macrophages, mast cells, and keratinocytes) also responding to this chemokine.

Monokine induced by γ-interferon (MIG)/CXCL9 is a T-cell chemoattractant induced by IFN-γ. It is closely related to two other CXC chemokines, IP-10/CXCL10 and I-TAC/CXCL11, whose genes are located near the CXCL9 gene on human chromosome 4. MIG, IP-10, and I-TAC elicit their chemotactic functions by interacting with the chemokine receptor CXCR3.

Interferon gamma-induced protein 10 (IP-10), also known as CXCL10, or small-inducible cytokine B10, is an 8.7 kDa protein that in humans is encoded by the CXCL10 gene located on human chromosome 4 in a cluster among several other CXC chemokines. IP-10 is secreted by several cell types in response to IFN-γ. These cell types include monocytes, endothelial cells and fibroblasts. IP-10 has been attributed to several roles, such as chemoattraction for monocytes/macrophages, T cells, NK cells, and dendritic cells, promotion of T cell adhesion to endothelial cells, antitumor activity, and inhibition of bone marrow colony formation and angiogenesis. This chemokine elicits its effects by binding to the cell surface chemokine receptor CXCR3, which can be found on both Th1 and Th2 cells.

Monocyte chemotactic protein-1 (MCP-1)/CCL2 recruits monocytes, memory T cells, and dendritic cells to sites of inflammation. MCP-1 is a monomeric polypeptide, with a molecular weight of approximately 13 kDa that is primarily secreted by monocytes, macrophages and dendritic cells. Platelet derived growth factor is a major inducer of MCP-1 gene. The MCP-1 protein is activated post-cleavage by metalloproteinase MMP-12. CCR2 and CCR4 are two cell surface receptors that bind MCP-1. During the adaptive immune response, CCR2 is upregulated on Th17 and T-regulatory cells, while CCR4 is upregulated on Th2 cells. MCP-1 is implicated in pathogeneses of several diseases characterized by monocytic infiltrates, such as psoriasis, rheumatoid arthritis and atherosclerosis. It is also implicated in the pathogenesis of SLE and a polymorphism of MCP-1 is linked to SLE in Caucasians. Administration of anti-MCP-1 antibodies in a model of glomerulonephritis reduces infiltration of macrophages and T cells, reduces crescent formation, as well as scarring and renal impairment.

Monocyte-specific chemokine 3 (MCP-3)/CCL7 specifically attracts monocytes and regulates macrophage function. It is produced by multiple cell types, including monocytes, macrophages, and dendritic cells. The CCL7 gene is located on chromosome 17 in humans, in a large cluster containing other CC chemokines. MCP-3 is most closely related to MCP-1, binding to CCR2.

Macrophage inflammatory protein-1α (MIP-1α)/CCL3 is encoded by the CCL3 gene in humans. MIP-1α is involved in the acute inflammatory state in the recruitment and activation of polymorphonuclear leukocytes (Wolpe et al., 1988). MIP-1α interacts with MIP-1β/CCL4, encoded by the CCL4 gene, with specificity for CCR5 receptors. It is a chemoattractant for natural killer cells, monocytes and a variety of other immune cells.

RANTES (Regulated on Activation, Normal T cell Expressed and Secreted)/CCL5 is encoded by the CCL5 gene on chromosome 17 in humans. RANTES is an 8 kDa protein chemotactic for T cells, eosinophils, and basophils, playing an active role in recruiting leukocytes to sites of inflammation. With the help of particular cytokines that are released by T cells (e.g. IL-2 and IFN-γ), RANTES induces the proliferation and activation of natural-killer (NK) cells. RANTES was first identified in a search for genes expressed "late" (3-5 days) after T cell activation and has been shown to interact with CCR3, CCR5 and CCR1. RANTES also activates the G-protein coupled receptor GPR75.

Eotaxin-1/CCL11 is a member of a CC chemokine subfamily of monocyte chemotactic proteins. In humans, there are three family members, CCL11 (eotaxin-1), CCL24 (eotaxin-2) and CCL26 (eotaxin-3). Eotaxin-1, also known as eosinophil chemotactic protein, is encoded by the CCL11 gene located on chromosome 17. Eotaxin-1 selectively recruits eosinophils and is implicated in allergic responses. The effects of Eotaxin-1 are mediated by its binding to G-protein-linked receptors CCR2, CCR3 and CCR5.

Soluble cell adhesion molecules (sCAMs) are a class of cell surface binding proteins that may represent important biomarkers for inflammatory processes involving activation or damage to cells such as platelets and the endothelium. They include soluble forms of the cell adhesion molecules ICAM-1, VCAM-1, E-selectin, L-selectin, and P-selectin (distinguished as sICAM-1, sVCAM-1, sE-selectin, sL-selectin, and sP-selectin). The cellular expression of CAMs is difficult to assess clinically, but these soluble forms are present in the circulation and may serve as markers for CAMs.

ICAM-1 (Intercellular Adhesion Molecule 1) also known as CD54, is encoded by the ICAM1 gene in humans. This gene encodes a cell surface glycoprotein which is typically expressed on endothelial cells and cells of the immune system. The protein encoded by this gene is a type of intercellular adhesion molecule continuously present in low concentrations in the membranes of leukocytes and endothelial cells. ICAM-1 can be induced by IL-1 and TNF-α, and is expressed by the vascular endothelium, macrophages, and lymphocytes.

The presence of heavy glycosylation and other structural characteristics of ICAM-1 lend the protein binding sites for numerous ligands. ICAM-1 possesses binding sites for a number of immune-associated ligands. Notably, ICAM-1 binds to macrophage adhesion ligand-1 (Mac-1; ITGB2/ITGAM), leukocyte function associated antigen-1 (LFA-1), and fibrinogen. These three proteins are generally expressed on endothelial cells and leukocytes, and they bind to ICAM-1 to facilitate transmigration of leukocytes across vascular endothelia in processes such as extravasation and the inflammatory response. As a result of these binding characteristics, ICAM-1 has classically been assigned the function of intercellular adhesion.

ICAM-1 is a member of the immunoglobulin superfamily, the superfamily of proteins, including B-cell receptors (membrane-bound antibodies) and T-cell receptors. In addition to its roles as an adhesion molecule, ICAM-1 has been shown to be a co-stimulatory molecule for the TCR on T-lymphocytes. The signal-transducing functions of ICAM-1 are associated primarily with proinflammatory pathways. In particular, ICAM-1 signaling leads to recruitment of inflammatory immune cells such as macrophages and granulocytes.

E-selectin, also known as CD62 antigen-like family member E (CD62E), endothelial-leukocyte adhesion molecule 1 (ELAM-1), or leukocyte-endothelial cell adhesion molecule 2 (LECAM2), is a cell adhesion molecule expressed on cytokine-activated endothelial cells. Playing an important role in inflammation, E-selectin is encoded by the SELE gene in humans. Its C-type lectin domain, EGF-like, SCR repeats, and transmembrane domains are each encoded by separate exons, whereas the E-selectin cytosolic domain derives from two exons. The E-selectin locus flanks the L-selectin locus on chromosome 1.

Different from P-selectin, which is stored in vesicles called Weibel-Palade bodies, E-selectin is not stored in the cell and has to be transcribed, translated, and transported to the cell surface. The production of E-selectin is stimulated by the expression of P-selectin which is stimulated by TNF-α, IL-1 and through engagement of TLR4 by LPS. It takes about two hours, after cytokine recognition, for E-selectin to be expressed on the endothelial cell's surface. Maximal expression of E-selectin occurs around 6-12 hours after cytokine stimulation, and levels returns to baseline within 24 hours.

E-selectin recognizes and binds to sialylated carbohydrates present on the surface proteins of leukocytes. E-selectin ligands are expressed by neutrophils, monocytes, eosinophils, memory-effector T-like lymphocytes, and natural killer cells. Each of these cell types is found in acute and chronic inflammatory sites in association with expression of E-selectin, thus implicating E-selectin in the recruitment of these cells to such inflammatory sites. These carbohydrates include members of the Lewis X and Lewis A families found on monocytes, granulocytes, and T-lymphocytes.

TNF Receptor Superfamily Members.

The tumor necrosis factor receptor (TNFR) superfamily of receptors and their respective ligands activate signaling pathways for cell survival, death, and differentiation. Members of the TNFR superfamily act through ligand-mediated trimerization and require adaptor molecules (e.g. TRAFs) to activate downstream mediators of cellular activation, including NF-κB and MAPK pathways, immune and inflammatory responses, and in some cases, apoptosis.

The prototypical member is TNF-α. Tumor necrosis factor (TNF, cachexin, or cachectin, and formerly known as tumor necrosis factor alpha or TNFα) is a cytokine involved in systemic inflammation and is a member of a group of cytokines that stimulate the acute phase reaction. It is produced by a number of immune cells, including macrophages, dendritic cells, and both T- and B-lymphocytes. Dysregulation of TNF-α production has been implicated in a variety of human diseases including Alzheimer's disease, cancer, major depression and autoimmune disease, including inflammatory bowel disease (IBD) and rheumatoid arthritis (RA).

TNF-α is produced as a 212-amino acid-long type II transmembrane protein arranged in stable homotrimers. From this membrane-integrated form the soluble homotrimeric cytokine (sTNF) is released via proteolytic cleavage by the metalloprotease TNF-α converting enzyme (TACE, also called ADAM17). The soluble 51 kDa trimeric sTNF may dissociate to the 17-kD monomeric form. Both the secreted and the membrane bound forms are biologically active. Tumor necrosis factor receptor 1 (TNFRI; TNFRSF1a; CD120a), is a trimeric cytokine receptor that is expressed in most tissues and binds both membranous and soluble TNF-α. The receptor cooperates with adaptor molecules (such as TRADD, TRAF, RIP), which is important in determining the outcome of the response (e.g., apoptosis, inflammation). Tumor necrosis factor II (TNFRII; TNFRSF1b; CD120b) has limited expression, primarily on immune cells (although during chronic inflammation, endothelial cells, including those of the lung and kidney, are induced to express TNFRII) and binds the membrane-bound form of the TNF-α homotrimer with greater affinity and avidity than soluble TNF-α. Unlike TNFRI, TNFRII does not contain a death domain (DD) and does not cause apoptosis, but rather contributes to the inflammatory response and acts as a co-stimulatory molecule in receptor-mediated B- and T-lymphocyte activation.

Fas, also known as apoptosis antigen 1 (APO-1 or APT), cluster of differentiation 95 (CD95) or tumor necrosis factor receptor superfamily member 6 (TNFRSF6) is a protein that in humans is encoded by the TNFRSF6 gene located on chromosome 10 in humans and 19 in mice. Fas is a death receptor on the surface of cells that leads to programmed cell death (apoptosis). Like other TNFR superfamily members, Fas is produced in membrane-bound form, but can be produced in soluble form, either via proteolytic cleavage or alternative splicing. The mature Fas protein has 319 amino acids, has a predicted molecular weight of 48 kD and is divided into 3 domains: an extracellular domain, a transmembrane domain, and a cytoplasmic domain. Fas forms the death-inducing signaling complex (DISC) upon ligand binding. Membrane-anchored Fas ligand on the surface of an adjacent cell causes oligomerization of Fas. Upon ensuing death domain (DD) aggregation, the receptor complex is internalized via the cellular endosomal machinery. This allows the adaptor molecule FADD to bind the death domain of Fas through its own death domain.

FADD also contains a death effector domain (DED) near its amino terminus, which facilitates binding to the DED of FADD-like interleukin-1 beta-converting enzyme (FLICE), more commonly referred to as caspase-8. FLICE can then self-activate through proteolytic cleavage into p10 and p18 subunits, two each of which form the active heterotetramer enzyme. Active caspase-8 is then released from the DISC into the cytosol, where it cleaves other effector caspases, eventually leading to DNA degradation, membrane blebbing, and other hallmarks of apoptosis.

In most cell types, caspase-8 catalyzes the cleavage of the pro-apoptotic BH3-only protein Bid into its truncated form, tBid. BH-3 only members of the Bcl-2 family exclusively engage anti-apoptotic members of the family (Bcl-2, Bcl-xL), allowing Bak and Bax to translocate to the outer mitochondrial membrane, thus permeabilizing it and facilitating release of pro-apoptotic proteins such as cytochrome c and Smac/DIABLO, an antagonist of inhibitors of apoptosis proteins (IAPs).

Fas ligand (FasL; CD95L; TNFSF6) is a type-II transmembrane protein that belongs to the tumor necrosis factor (TNF) family. Its binding with its receptor induces apoptosis. FasL/Fas interactions play an important role in the regulation of the immune system and the progression of cancer. Soluble Fas ligand is generated by cleaving membrane-bound FasL at a conserved cleavage site by the external matrix metalloproteinase MMP-7.

Apoptosis triggered by Fas-Fas ligand binding plays a fundamental role in the regulation of the immune system. Its functions include T-cell homeostasis (the activation of T-cells leads to their expression of the Fas ligand; T cells are initially resistant to Fas-mediated apoptosis during clonal expansion, but become progressively more sensitive the longer they are activated, ultimately resulting in activation-induced cell death (AICD)), cytotoxic T-cell activity (Fas-induced apoptosis and the perforin pathway are the two main mechanisms by which cytotoxic T lymphocytes induce cell death in cells expressing foreign antigens), immune privilege (cells in immune privileged areas such as the cornea or testes express Fas ligand and induce the apoptosis of infiltrating lymphocytes), maternal tolerance (Fas ligand may be instrumental in the prevention of leukocyte trafficking between the mother and the fetus, although no pregnancy defects have yet been attributed to a faulty Fas-Fas ligand system) and tumor counterattack (tumors may over-express Fas ligand and induce the apoptosis of infiltrating lymphocytes, allowing the tumor to escape the effects of an immune response).

CD154, also called CD40 ligand (CD40L), is a member of the TNF superfamily protein that is expressed primarily on activated T cells. CD40L binds to CD40 (TNFRSF4), which is constitutively expressed by antigen-presenting cells (APC), including dendritic cells, macrophages, and B cells. CD40L engagement of CD40 induces maturation and activation of dendritic cells and macrophages in association with T cell receptor stimulation by MHC molecules on the APC. CD40L regulates B cell activation, proliferation, antibody production, and isotype switching by engaging CD40 on the B cell surface. A defect in this gene results in an inability to undergo immunoglobulin class switch and is associated with hyper IgM syndrome. While CD40L was originally described on T lymphocytes, its expression has since been found on a wide variety of cells, including platelets, endothelial cells, and aberrantly on B lymphocytes during periods of chronic inflammation.

B-cell activating factor (BAFF) also known as B Lymphocyte Stimulator (BLyS), TNF- and APOL-related leukocyte expressed ligand (TALL-1), and CD27 is encoded by the TNFSF13C gene in humans. BLyS is a 285-amino acid long peptide glycoprotein which undergoes glycosylation at residue 124. It is expressed as a membrane-bound type II transmembrane protein on various cell types including monocytes, dendritic cells and bone marrow stromal cells. The transmembrane form can be cleaved from the membrane, generating a soluble protein fragment. This cytokine is expressed in B cell lineage cells, and acts as a potent B cell activator. It has been also shown to play an important role in the proliferation and differentiation of B cells.

BLyS is a ligand for receptors TNFRSF13B/TACI, TNFRSF17/BCMA, and TNFRSF13C/BAFFR. These receptors are expressed mainly on mature B lymphocytes and their expression varies in dependence of B cell maturation (TACI is also found on a subset of T-cells and BCMA on plasma cells). BAFF-R is involved in the positive regulation during B cell development. TACI binds BLyS with the least affinity; its affinity is higher for a protein similar to BLyS, called a proliferation-inducing ligand (APRIL). BCMA displays an intermediate binding phenotype and will bind to either BLyS or APRIL to varying degrees. Signaling through BAFF-R and BCMA stimulates B lymphocytes to undergo proliferation and to counter apoptosis. All these ligands act as homotrimers (i.e. three of the same molecule) interacting with homotrimeric receptors, although BAFF has been known to be active as either a hetero- or homotrimer.

Excessive level of BLyS causes abnormally high antibody production, results in systemic lupus erythmatosis, rheumatoid arthritis, and many other autoimmune diseases. Belimumab (BENLYSTA®) is a monoclonal antibody developed by Human Genome Sciences and GlaxoSmithKline, with significant discovery input by Cambridge Antibody Technology, which specifically recognizes and inhibits the biological activity of B-Lymphocyte stimulator (BLyS) and is in clinical trials for treatment of Systemic lupus erythematosus and other auto-immune diseases. Blisibimod, a fusion protein inhibitor of BLyS, is in development by Anthera Pharmaceuticals, also primarily for the treatment of systemic lupus erythematosus.

A proliferation-inducing ligand (APRIL), or tumor necrosis factor ligand superfamily member 13 (TNFSF13), is a protein that in humans is encoded by the TNFSF13 gene. APRIL has also been designated CD256 (cluster of differentiation 256). The protein encoded by this gene is a member of the tumor necrosis factor ligand (TNF) ligand family. This protein is a ligand for TNFRSF13B/TACI and TNFRSF17/BCMA receptors. This protein and its receptor are both found to be important for B cell development. In vivo experiments suggest an important role for APRIL in the long-term survival of plasma cells in the bone marrow. Mice deficient in APRIL demonstrate a reduced ability to support plasma cell survival. In vitro experiments suggested that this protein may be able to induce apoptosis through its interaction with other TNF receptor family proteins such as TNFRSF6/FAS and TNFRSF14/HVEM. Three alternatively spliced transcript variants of this gene encoding distinct isoforms have been reported.

Other Flare Factors.

Leptin is a 16-kDa protein hormone that plays a key role in regulating energy intake and expenditure, including appetite and hunger, metabolism, and behavior. It is one of a number of adipokines, including adiponectin and resistin. The reported rise in leptin following acute infection and chronic inflammation, including autoimmune disease, suggests that leptin actively participates in the immune response. Leptin levels increase in response to a number of innate cytokines, including TNF-α and IL-6. Leptin is a member of the cytokine family that includes IL-6, IL-12, and G-CSF. Leptin functions by binding to the leptin receptor, which is expressed by polymorphonuclear neutrophils, circulating leukocytes (including monocytes), and NK cells. Leptin influences the rise in the chemokine MCP-1, allowing for recruitment of monocytes and macrophages to sites of inflammation.

Stem Cell Factor (also known as SCF, kit-ligand, KL, or steel factor) is a cytokine that binds to the c-Kit receptor (CD117). SCF can exist both as a transmembrane protein and a soluble protein. This cytokine plays an important role in hematopoiesis (formation of blood cells), spermatogenesis, and melanogenesis. The gene encoding stem cell factor (SCF) is found on the Sl locus in mice and on chromosome 12q22-12q24 in humans. The soluble and transmembrane forms of the protein are formed by alternative splicing of the same RNA transcript.

The soluble form of SCF contains a proteolytic cleavage site in exon 6. Cleavage at this site allows the extracellular portion of the protein to be released. The transmembrane form of SCF is formed by alternative splicing that excludes exon 6. Both forms of SCF bind to c-Kit and are biologically active. Soluble and transmembrane SCF is produced by fibroblasts and endothelial cells. Soluble SCF has a molecular weight of 18.5 kDa and forms a dimer. SCF plays an important role in the hematopoiesis, providing guidance cues that direct hematopoietic stem cells (HSCs) to their stem cell niche (the microenvironment in which a stem cell resides), and it plays an important role in HSC maintenance. SCF plays a role in the regulation of HSCs in the stem cell niche in the bone marrow. SCF has been shown to increase the survival of HSCs in vitro and contributes to the self-renewal and maintenance of HSCs in vivo. HSCs at all stages of development express the same levels of the receptor for SCF (c-Kit). The stromal cells that surround HSCs are a component of the stem cell niche, and they release a number of ligands, including SCF.

A small percentage of HSCs regularly leave the bone marrow to enter circulation and then return to their niche in the bone marrow. It is believed that concentration gradients of SCF, along with the chemokine SDF-1, allow HSCs to find their way back to the niche.

In addition to hematopoiesis, SCF is thought to contribute to inflammation via its binding to c-kit on dendritic cells.

This engagement leads to increased secretion of IL-6 and the promoted development of Th2 and Th17-type immune responses. Th2 cytokines synergize with SCF in the activation of mast cells, and integral promoter of allergic inflammation. The induction of IL-17 allows for further upregulation of SCF by epithelial cells and the promotion of granulopoiesis. In the lung, the upregulation of IL-17 induces IL-8 and MIP-2 to recruit neutrophils to the lung. The chronic induction of IL-17 has been demonstrated to play a role in autoimmune diseases, including multiple sclerosis and rheumatoid arthritis.

B. Markers Depressed with Impending Flare

IL-10.

Interleukin-10 (IL-10), also known as human cytokine synthesis inhibitory factor (CSIF), is an anti-inflammatory cytokine. The IL-10 protein is a homodimer; each of its subunits is 178-amino-acid long. IL-10 is classified as a class-2 cytokine, a set of cytokines including IL-19, IL-20, IL-22, IL-24 (Mda-7), and IL-26, interferons and interferon-like molecules. In humans, IL-10 is encoded by the IL10 gene, which is located on chromosome 1 and comprises 5 exons. IL-10 is primarily produced by monocytes and lymphocytes, namely Th2 cells, CD4$^+$CD25$^+$Foxp3$^+$ regulatory T cells, and in a certain subset of activated T cells and B cells. IL-10 can be produced by monocytes upon PD-1 triggering in these cells. The expression of IL-10 is minimal in unstimulated tissues and requires receptor-mediated cellular activation for its expression. IL-10 expression is tightly regulated at the transcriptional and post-transcriptional level. Extensive IL-10 locus remodeling is observed in monocytes upon stimulation of TLR or Fc receptor pathways. IL-10 induction involves ERK1/2, p38 and NFκB signalling and transcriptional activation via promoter binding of the transcription factors NFκB and AP-1. IL-10 may autoregulate its expression via a negative feed-back loop involving autocrine stimulation of the IL-10 receptor and inhibition of the p38 signaling pathway. Additionally, IL-10 expression is extensively regulated at the post-transcriptional level, which may involve control of mRNA stability via AU-rich elements and by microRNAs such as let-7 or miR-106.

IL-10 is a cytokine with pleiotropic effects in immunoregulation and inflammation. It downregulates the expression of multiple Th-pathway cytokines, MHC class II antigens, and co-stimulatory molecules on macrophages. It also enhances B cell survival, proliferation, and antibody production. IL-10 can block NF-κB activity, and is involved in the regulation of the JAK-STAT signaling pathway.

TGF-β.

Transforming growth factor beta (TGF-β) controls proliferation, cellular differentiation, and other functions in most cells. TGF-β is a secreted protein that exists in at least three isoforms called TGF-β1, TGF-β2 and TGF-β3. It was also the original name for TGF-β1, which was the founding member of this family. The TGF-β family is part of a superfamily of proteins known as the transforming growth factor beta superfamily, which includes inhibins, activin, anti-müllerian hormone, bone morphogenetic protein, decapentaplegic and Vg-1.

Most tissues have high expression of the gene encoding TGF-β. That contrasts with other anti-inflammatory cytokines such as IL-10, whose expression is minimal in unstimulated tissues and seems to require triggering by commensal or pathogenic flora.

The peptide structures of the three members of the TGF-β family are highly similar. They are all encoded as large protein precursors; TGF-β1 contains 390 amino acids and TGF-β2 and TGF-β3 each contain 412 amino acids. They each have an N-terminal signal peptide of 20-30 amino acids that they require for secretion from a cell, a pro-region (called latency associated peptide or LAP), and a 112-114 amino acid C-terminal region that becomes the mature TGF-β molecule following its release from the pro-region by proteolytic cleavage. The mature TGF-β protein dimerizes to produce a 25 kDa active molecule with many conserved structural motifs.

TGF-β plays a crucial role in the regulation of the cell cycle. TGF-β causes synthesis of p15 and p21 proteins, which block the cyclin:CDK complex responsible for Retinoblastoma protein (Rb) phosphorylation. Thus TGF-β blocks advance through the G1 phase of the cycle TGF-β is necessary for CD4$^+$CD25$^+$Foxp3$^+$ T-regulatory cell differentiation and suppressive function. In the presence of IL-6, TGF-β contributes to the differentiation of pro-inflammatory Th17 cells.

SDF-1.

Stromal cell-derived factor 1 (SDF-1), also known as C—X—C motif chemokine 12 (CXCL12), is encoded by the CXCL12 gene on chromosome 10 in humans. SDF-1 is produced in two forms, SDF-1α/CXCL12a and SDF-1β/CXCL12b, by alternate splicing of the same gene. Chemokines are characterized by the presence of four conserved cysteines, which form two disulfide bonds. The CXCL12 proteins belong to the group of CXC chemokines, whose initial pair of cysteines are separated by one intervening amino acid.

CXCL12 is strongly chemotactic for lymphocytes. During embryogenesis it directs the migration of hematopoietic cells from fetal liver to bone marrow and the formation of large blood vessels. CXCL12 knockout mice are embryonic lethal.

The receptor for this chemokine is CXCR4, which was previously called LESTR or fusin. This CXCL12-CXCR4 interaction was initially thought to be exclusive (unlike for other chemokines and their receptors), but recently it was suggested that CXCL12 may also bind the CXCR7 receptor. The CXCR4 receptor is a G-Protein Coupled Receptor that is widely expressed, including on T-regulatory cells, allowing them to be recruited to promote lymphocyte homeostasis and immune tolerance. In addition to CXCL12, CXCR4 binds Granulocyte-Colony Stimulating Factor (G-CSF). G-CSF binds CXCR4 to prevent SDF-1 binding, which results in the inhibition of the pathway.

IL-1RA.

The interleukin-1 receptor antagonist (IL-1RA) is a protein that in humans is encoded by the IL1RN gene. A member of the IL-1 cytokine family, IL-1RA, is an agent that binds non-productively to the cell surface interleukin-1 receptor (IL-1R), preventing IL-1 from binding and inducing downstream signaling events.

IL1Ra is secreted by various types of cells including immune cells, epithelial cells, and adipocytes, and is a natural inhibitor of the pro-inflammatory effect of IL-1α and IL1β. This gene and five other closely related cytokine genes form a gene cluster spanning approximately 400 kb on chromosome 2. Four alternatively spliced transcript variants encoding distinct isoforms have been reported.

An interleukin 1 receptor antagonist is used in the treatment of rheumatoid arthritis, an autoimmune disease in which IL-1 plays a key role. It is commercially produced as anakinra, which is a human recombinant form of IL-1RA. Anakinra has shown both safety and efficacy in improving arthritis in an open trial on four SLE patients, with only short-lasting therapeutic effects in two patients.

III. ASSESSING BIOMARKER EXPRESSION

Thus, in accordance with the present invention, methods are provided for the assaying of expression of biomarkers as set forth above. As discussed above, the principle applications are to (a) determine if a patient has SLE as opposed to a distinct autoimmune condition, (b) to determine the severity of the disease, (c) to determine the current intensity of the inflammatory state, (d) to predict or assess an impending disease flare, and (e) to predict or assess the efficacy of a therapy. In each of these assays, the expression of various biomarkers will be measured, and in some, the expression is measured multiple times to assess not only absolute values, but changes in these values overtime. Virtually any method of measuring gene expression may be utilized, and the following discussion is exemplary in nature and in no way limiting.

A. Immunologic Assays

There are a variety of methods that can be used to assess protein expression. One such approach is to perform protein identification with the use of antibodies. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting. The term "antibody" also refers to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies, both polyclonal and monoclonal, are also well known in the art (see, e.g., Antibodies: A Laboratory Manual, Cold Spring Harbor Laboratory, 1988; incorporated herein by reference). In particular, antibodies to calcyclin, calpactin I light chain, astrocytic phosphoprotein PEA-15 and tubulin-specific chaperone A are contemplated.

In accordance with the present invention, immunodetection methods are provided. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle and Ben-Zeev O, 1999; Gulbis and Galand, 1993; De Jager et al., 1993; and Nakamura et al., 1987, each incorporated herein by reference.

In general, the immunobinding methods include obtaining a sample suspected of containing a relevant polypeptide, and contacting the sample with a first antibody under conditions effective to allow the formation of immunocomplexes. In terms of antigen detection, the biological sample analyzed may be any sample that is suspected of containing an antigen, such as, for example, a tissue section or specimen, a homogenized tissue extract, a cell, or even a biological fluid.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

As detailed above, immunoassays are in essence binding assays. Certain immunoassays are the various types of enzyme linked immunosorbent assays (ELISAs) and radioimmunoassays (RIA) known in the art. However, it will be readily appreciated that detection is not limited to such techniques, and Western blotting, dot blotting, FACS analyses, and the like may also be used.

In one exemplary ELISA, the antibodies of the invention are immobilized onto a selected surface exhibiting protein affinity, such as a well in a polystyrene microtiter plate. Then, a test composition suspected of containing the antigen, such as a clinical sample, is added to the wells. After binding and washing to remove non-specifically bound immune complexes, the bound antigen may be detected. Detection is generally achieved by the addition of another antibody that is linked to a detectable label. This type of ELISA is a simple "sandwich ELISA." Detection may also be achieved by the addition of a second antibody, followed by the addition of a third antibody that has binding affinity for the second antibody, with the third antibody being linked to a detectable label.

In another exemplary ELISA, the samples suspected of containing the antigen are immobilized onto the well surface and then contacted with the anti-ORF message and anti-ORF translated product antibodies of the invention. After binding and washing to remove non-specifically bound immune complexes, the bound anti-ORF message and anti-ORF translated product antibodies are detected. Where the initial anti-ORF message and anti-ORF translated product antibodies are linked to a detectable label, the immune complexes may be detected directly. Again, the immune complexes may be detected using a second antibody that has binding affinity for the first anti-ORF message and anti-ORF translated product antibody, with the second antibody being linked to a detectable label.

Another ELISA in which the antigens are immobilized, involves the use of antibody competition in the detection. In this ELISA, labeled antibodies against an antigen are added to the wells, allowed to bind, and detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/TWEEN® (polysorbate 20). These added agents also tend to assist in the reduction of nonspecific background. The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Another antibody-based approach to assessing biomarkers expression is Fluorescence-Activated Cell Sorting (FACS), a specialized type of flow cytometry. It provides a method for sorting a heterogeneous mixture of biological cells into two or more containers, one cell at a time, based upon the specific light scattering and fluorescent characteristics of each cell. It provides fast, objective and quantitative recording of fluorescent signals from individual cells as well as physical separation of cells of particular interest. A cell suspension is entrained in the center of a narrow, rapidly flowing stream of liquid. The flow is arranged so that there is a large separation between cells relative to their diameter. A vibrating mechanism causes the stream of cells to break into individual droplets. The system is adjusted so that there is a low probability of more than one cell per droplet. Just before the stream breaks into droplets, the flow passes through a fluorescence measuring station where the fluorescent character of interest of each cell is measured. An electrical charging ring is placed just at the point where the stream breaks into droplets. A charge is placed on the ring based on the immediately prior fluorescence intensity measurement, and the opposite charge is trapped on the droplet as it breaks from the stream. The charged droplets then fall through an electrostatic deflection system that diverts droplets into containers based upon their charge. In some systems, the charge is applied directly to the stream, and the droplet breaking off retains charge of the same sign as the stream. The stream is then returned to neutral after the droplet breaks off. One common way to use FAC is with a fluorescently labeled antibody that binds to a target on or in a cell, thereby identifying cells with a given target. This technique can be used quantitatively where the amount of fluorescent activity correlates to the amount of target, thereby permitting one to sort based on relative amounts of fluorescence, and hence relative amounts of the target.

Bead-based xMAP® Technology may also be applied to immunologic detection in conjunction with the presently claimed invention. This technology combines advanced fluidics, optics, and digital signal processing with proprietary microsphere technology to deliver multiplexed assay capabilities. Featuring a flexible, open-architecture design, xMAP® technology can be configured to perform a wide variety of bioassays quickly, cost-effectively and accurately.

Fluorescently-coded microspheres are arranged in up to 500 distinct sets. Each bead set can be coated with a reagent specific to a particular bioassay (e.g., an antibody), allowing the capture and detection of specific analytes from a sample, such as the biomarkers of the present application. Inside the xMAP® multiplex analyzer, a light source excites the internal dyes that identify each microsphere particle, and also any reporter dye captured during the assay. Many readings are made on each bead set, which further validates the results. Using this process, xMAP® Technology allows multiplexing of up to 500 unique bioassays within a single sample, both rapidly and precisely. Unlike other flow cytometer microsphere-based assays which use a combination of different sizes and color intensities to identify an individual microsphere, xMAP® technology uses 5.6 micron size microspheres internally dyed with red and infrared fluorophores via a proprietary dying process to create 500 unique dye mixtures which are used to identify each individual microsphere.

Some of the advantages of xMAP® include multiplexing (reduces costs and labor), generation of more data with less sample, less labor and lower costs, faster, more reproducible results than solid, planar arrays, and focused, flexible multiplexing of 1 to 500 analytes to meet a wide variety of applications.

B. Nucleic Acid Detection

In alternative embodiments for detecting protein expression, one may assay for gene transcription. For example, an indirect method for detecting protein expression is to detect mRNA transcripts from which the proteins are made. The following is a discussion of such methods, which are applicable particularly to calcyclin, calpactin I light chain, astrocytic phosphoprotein PEA-15 and tubulin-specific chaperone A in the context of the present invention.

1. Amplification of Nucleic Acids

Since many mRNAs are present in relatively low abundance, nucleic acid amplification greatly enhances the ability to assess expression. The general concept is that nucleic acids can be amplified using paired primers flanking the region of interest. The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to selected genes are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids containing one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemilluminescence, radioactive scintigraphy of incorporated radiolabel or fluorescent label or even via a system using electrical and/or thermal impulse signals.

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 1989). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Whereas standard PCR usually uses one pair of primers to amplify a specific sequence, multiplex-PCR (MPCR) uses multiple pairs of primers to amplify many sequences simultaneously. The presence of many PCR primers in a single tube could cause many problems, such as the increased formation of mispaired PCR products and "primer dimers," the amplification discrimination of longer DNA fragment and so on. Normally, MPCR buffers contain a Taq Polymerase additive, which decreases the competition among amplicons and the amplification discrimination of longer DNA fragment during MPCR. MPCR products can further be hybridized with gene-specific probe for verification. Theoretically, one should be able to use as many as primers as necessary. However, due to side effects (primer dimers, mispaired PCR products, etc.) caused during MPCR, there is a limit (less than 20) to the number of primers that can be used in a MPCR reaction. See also European Application No. 0 364 255 and Mueller and Wold (1989).

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which are incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site, may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

2. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 2001). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

3. Nucleic Acid Arrays

Microarrays comprise a plurality of polymeric molecules spatially distributed over, and stably associated with, the surface of a substantially planar substrate, e.g., biochips. Microarrays of polynucleotides have been developed and find use in a variety of applications, such as screening and DNA sequencing. One area in particular in which microarrays find use is in gene expression analysis.

In gene expression analysis with microarrays, an array of "probe" oligonucleotides is contacted with a nucleic acid sample of interest, i.e., target, such as polyA mRNA from a particular tissue type. Contact is carried out under hybridization conditions and unbound nucleic acid is then removed. The resultant pattern of hybridized nucleic acid provides information regarding the genetic profile of the sample tested. Methodologies of gene expression analysis on microarrays are capable of providing both qualitative and quantitative information.

A variety of different arrays which may be used are known in the art. The probe molecules of the arrays which are capable of sequence specific hybridization with target nucleic acid may be polynucleotides or hybridizing analogues or mimetics thereof, including: nucleic acids in which the phosphodiester linkage has been replaced with a substitute linkage, such as phophorothioate, methylimino, methylphosphonate, phosphoramidate, guanidine and the like; nucleic acids in which the ribose subunit has been substituted, e.g., hexose phosphodiester; peptide nucleic acids; and the like. The length of the probes will generally range from 10 to 1000 nts, where in some embodiments the probes will be oligonucleotides and usually range from 15 to 150 nts and more usually from 15 to 100 nts in length, and in other embodiments the probes will be longer, usually ranging in length from 150 to 1000 nts, where the polynucleotide probes may be single- or double-stranded, usually single-stranded, and may be PCR fragments amplified from cDNA.

The probe molecules on the surface of the substrates will correspond to selected genes being analyzed and be positioned on the array at a known location so that positive hybridization events may be correlated to expression of a particular gene in the physiological source from which the target nucleic acid sample is derived. The substrates with which the probe molecules are stably associated may be fabricated from a variety of materials, including plastics, ceramics, metals, gels, membranes, glasses, and the like. The arrays may be produced according to any convenient methodology, such as preforming the probes and then stably associating them with the surface of the support or growing the probes directly on the support. A number of different array configurations and methods for their production are known to those of skill in the art and disclosed in U.S. Pat. Nos. 5,445,934, 5,532,128, 5,556,752, 5,242,974, 5,384,261, 5,405,783, 5,412,087, 5,424,186, 5,429,807, 5,436,327, 5,472,672, 5,527,681, 5,529,756, 5,545,531, 5,554,501, 5,561,071, 5,571,639, 5,593,839, 5,599,695, 5,624,711, 5,658,734, 5,700,637, and 6,004,755.

Following hybridization, where non-hybridized labeled nucleic acid is capable of emitting a signal during the detection step, a washing step is employed where unhybridized labeled nucleic acid is removed from the support surface, generating a pattern of hybridized nucleic acid on the substrate surface. A variety of wash solutions and protocols for their use are known to those of skill in the art and may be used.

Where the label on the target nucleic acid is not directly detectable, one then contacts the array, now comprising bound target, with the other member(s) of the signal producing system that is being employed. For example, where the label on the target is biotin, one then contacts the array with streptavidin-fluorescer conjugate under conditions sufficient for binding between the specific binding member pairs to occur. Following contact, any unbound members of the signal producing system will then be removed, e.g., by washing. The specific wash conditions employed will necessarily depend on the specific nature of the signal producing system that is employed, and will be known to those of skill in the art familiar with the particular signal producing system employed.

The resultant hybridization pattern(s) of labeled nucleic acids may be visualized or detected in a variety of ways, with the particular manner of detection being chosen based on the particular label of the nucleic acid, where representative detection means include scintillation counting, autoradiography, fluorescence measurement, calorimetric measurement, light emission measurement and the like.

Prior to detection or visualization, where one desires to reduce the potential for a mismatch hybridization event to generate a false positive signal on the pattern, the array of hybridized target/probe complexes may be treated with an endonuclease under conditions sufficient such that the endonuclease degrades single stranded, but not double stranded DNA. A variety of different endonucleases are known and may be used, where such nucleases include: mung bean nuclease, S1 nuclease, and the like. Where such treatment is employed in an assay in which the target nucleic acids are not labeled with a directly detectable label, e.g., in an assay with biotinylated target nucleic acids, the endonuclease treatment will generally be performed prior to contact of the array with the other member(s) of the signal producing system, e.g., fluorescent-streptavidin conjugate. Endonuclease treatment, as described above, ensures that only end-labeled target/probe complexes having a substantially complete hybridization at the 3' end of the probe are detected in the hybridization pattern.

Following hybridization and any washing step(s) and/or subsequent treatments, as described above, the resultant hybridization pattern is detected. In detecting or visualizing the hybridization pattern, the intensity or signal value of the label will be not only be detected but quantified, by which is meant that the signal from each spot of the hybridization will be measured and compared to a unit value corresponding the signal emitted by known number of end-labeled target nucleic acids to obtain a count or absolute value of the copy number of each end-labeled target that is hybridized to a particular spot on the array in the hybridization pattern.

4. RNA Sequencing

RNA-seq (RNA Sequencing), also called Whole Transcriptome Shotgun Sequencing (WTSS), is a technology that utilizes the capabilities of next-generation sequencing to reveal a snapshot of RNA presence and quantity from a genome at a given moment in time.

The transcriptome of a cell is dynamic; it continually changes as opposed to a static genome. The recent developments of Next-Generation Sequencing (NGS) allow for increased base coverage of a DNA sequence, as well as higher sample throughput. This facilitates sequencing of the RNA transcripts in a cell, providing the ability to look at alternative gene spliced transcripts, post-transcriptional changes, gene fusion, mutations/SNPs and changes in gene expression. In addition to mRNA transcripts, RNA-Seq can look at different populations of RNA to include total RNA, small RNA, such as miRNA, tRNA, and ribosomal profiling. RNA-Seq can also be used to determine exon/intron boundaries and verify or amend previously annotated 5' and 3' gene boundaries, Ongoing RNA-Seq research includes observing cellular pathway alterations during infection, and gene expression level changes in cancer studies. Prior to NGS, transcriptomics and gene expression studies were previously done with expression microarrays, which contain thousands of DNA sequences that probe for a match in the target sequence, making available a profile of all transcripts being expressed. This was later done with Serial Analysis of Gene Expression (SAGE).

One deficiency with microarrays that makes RNA-Seq more attractive has been limited coverage; such arrays target the identification of known common alleles that represent approximately 500,000 to 2,000,000 SNPs of the more than 10,000,000 in the genome. As such, libraries aren't usually available to detect and evaluate rare allele variant transcripts, and the arrays are only as good as the SNP databases they're designed from, so they have limited application for research purposes. Many cancers for example are caused by rare <1% mutations and would go undetected. However, arrays still have a place for targeted identification of already known common allele variants, making them ideal for regulatory-body approved diagnostics such as cystic fibrosis.

RNA 'Poly(A)' Library.

Creation of a sequence library can change from platform to platform in high throughput sequencing, where each has several kits designed to build different types of libraries and adapting the resulting sequences to the specific requirements of their instruments. However, due to the nature of the template being analyzed, there are commonalities within each technology. Frequently, in mRNA analysis the 3' polyadenylated (poly(A)) tail is targeted in order to ensure that coding RNA is separated from noncoding RNA. This can be accomplished simply with poly (T) oligos covalently attached to a given substrate. Presently many studies utilize magnetic beads for this step. The Protocol Online web site provides a list of several protocols relating to mRNA isolation.

Studies including portions of the transcriptome outside poly(A) RNAs have shown that when using poly(T) magnetic beads, the flow-through RNA (non-poly(A) RNA) can yield important noncoding RNA gene discovery which would have otherwise gone unnoticed. Also, since ribosomal RNA represents over 90% of the RNA within a given cell, studies have shown that its removal via probe hybridization increases the capacity to retrieve data from the remaining portion of the transcriptome.

The next step is reverse transcription. Due to the 5' bias of randomly primed-reverse transcription as well as secondary structures influencing primer binding sites, hydrolysis of RNA into 200-300 nucleotides prior to reverse transcription reduces both problems simultaneously. However, there are trade-offs with this method where although the overall body of the transcripts are efficiently converted to DNA, the 5' and 3' ends are less so. Depending on the aim of the study, researchers may choose to apply or ignore this step.

Once the cDNA is synthesized it can be further fragmented to reach the desired fragment length of the sequencing system.

Small RNA/Non-Coding RNA Sequencing.

When sequencing RNA other than mRNA the library preparation is modified. The cellular RNA is selected based on the desired size range. For small RNA targets, such as miRNA, the RNA is isolated through size selection. This can be performed with a size exclusion gel, through size selection magnetic beads, or with a commercially developed kit. Once isolated, linkers are added to the 3' and 5' end then purified. The final step is cDNA generation through reverse transcription.

Direct RNA Sequencing.

As converting RNA into cDNA using reverse transcriptase has been shown to introduce biases and artifacts that may interfere with both the proper characterization and quantification of transcripts, single molecule Direct RNA Sequencing (DRS™) technology is currently under development by Helicos. DRS™ sequences RNA molecules directly in a massively-parallel manner without RNA conversion to cDNA or other biasing sample manipulations such as ligation and amplification.

Transcriptome Assembly.

Two different assembly methods are used for producing a transcriptome from raw sequence reads: de-novo and genome-guided.

The first approach does not rely on the presence of a reference genome in order to reconstruct the nucleotide sequence. Due to the small size of the short reads de novo assembly may be difficult though some software does exist (Velvet (algorithm), Oases, and Trinity to mention a few), as there cannot be large overlaps between each read needed to easily reconstruct the original sequences. The deep coverage also makes the computing power to track all the possible alignments prohibitive. This deficit can improved using longer sequences obtained from the same sample using other techniques such as Sanger sequencing, and using larger reads as a "skeleton" or a "template" to help assemble reads in difficult regions (e.g., regions with repetitive sequences).

An "easier" and relatively computationally cheaper approach is that of aligning the millions of reads to a "reference genome." There are many tools available for aligning genomic reads to a reference genome (sequence alignment tools), however, special attention is needed when alignment of a transcriptome to a genome, mainly when dealing with genes having intronic regions. Several software packages exist for short read alignment, and recently specialized algorithms for transcriptome alignment have been developed, e.g. Bowtie for RNA-seq short read alignment, TopHat for aligning reads to a reference genome to discover splice sites, Cufflinks to assemble the transcripts and compare/merge them with others, or FANSe. These tools can also be combined to form a comprehensive system.

Although numerous solutions to the assembly quest have been proposed, there is still room for improvement given the resulting variability of the approaches. A group from the Center for Computational Biology at the East China Normal University in Shanghai compared different de novo and genome-guided approaches for RNA-Seq assembly. They noted that, although most of the problems can be solved using graph theory approaches, there is still a consistent level of variability in all of them. Some algorithms outperformed the common standards for some species while still struggling for others. The authors suggest that the "most reliable" assembly could be then obtained by combining different approaches. Interestingly, these results are consistent with NGS-genome data obtained in a recent contest called Assemblathon where 21 contestants analyzed sequencing data from three different vertebrates (fish, snake and bird) and handed in a total of 43 assemblies. Using a metric made of 100 different measures for each assembly, the reviewers concluded that 1) assembly quality can vary a lot depending on which metric is used and 2) assemblies that scored well in one species didn't really perform well in the other species.

As discussed above, sequence libraries are created by extracting mRNA using its poly(A) tail, which is added to the mRNA molecule post-transcriptionally and thus splicing has taken place. Therefore, the created library and the short reads obtained cannot come from intronic sequences, so library reads spanning the junction of two or more exons will not align to the genome.

A possible method to work around this is to try to align the unaligned short reads using a proxy genome generated with known exonic sequences. This need not cover whole exons, only enough so that the short reads can match on both sides of the exon-exon junction with minimum overlap. Some experimental protocols allow the production of strand specific reads.

Gene expression. The characterization of gene expression in cells via measurement of mRNA levels has long been of interest to researchers, both in terms of which genes are expressed in what tissues, and at what levels. Even though it has been shown that due to other post transcriptional gene regulation events (such as RNA interference) there is not necessarily always a strong correlation between the abundance of mRNA and the related proteins, measuring mRNA concentration levels is still a useful tool in determining how the transcriptional machinery of the cell is affected in the presence of external signals (e.g., drug treatment), or how cells differ between a healthy state and a diseased state.

Expression can be deduced via RNA-seq to the extent at which a sequence is retrieved. Transcriptome studies in yeast show that in this experimental setting, a four-fold coverage is required for amplicons to be classified and characterized as an expressed gene. When the transcriptome is fragmented prior to cDNA synthesis, the number of reads corresponding to the particular exon normalized by its length in vivo yields gene expression levels which correlate with those obtained through qPCR.

The only way to be absolutely sure of the individual's mutations is to compare the transcriptome sequences to the germline DNA sequence. This enables the distinction of homozygous genes versus skewed expression of one of the alleles and it can also provide information about genes that were not expressed in the transcriptomic experiment. An R-based statistical package known as CummeRbund can be used to generate expression comparison charts for visual analysis.

IV. TREATING SLE

Advantages accruing to the present invention include earlier intervention, when the symptoms of a flare have not appeared. Thus, the present invention contemplates the treatment of SLE using standard therapeutic approaches where indicated. In general, the treatment of SLE involves treating elevated disease activity and trying to minimize the organ damage that can be associated with this increased inflammation and increased immune complex formation/deposition/complement activation. Foundational treatment can include corticosteroids and anti-malarial drugs. Certain types of lupus nephritis such as diffuse proliferative glomerulonephritis require bouts of cytotoxic drugs. These drugs include, most commonly, cyclophosphamide and mycophenolate. Hydroxychloroquine (HCQ) was approved by the FDA for lupus in 1955. Some drugs approved for other diseases are used for SLE 'off-label.' In November 2010, an FDA advisory panel recommended approving belimumab (BENLYSTA®) as a treatment for elevated disease activity seen in autoantibody-positive lupus patients. The drug was approved by the FDA in March 2011.

Due to the variety of symptoms and organ system involvement with SLE, its severity in an individual must be assessed in order to successfully treat SLE. Mild or remittent disease may, sometimes, be safely left minimally treated with hydroxychloroquine alone. If required, nonsteroidal anti-inflammatory drugs and low dose steroids may also be used. Hydroxychloroquine (HCQ) is an FDA-approved antimalarial used for constitutional, cutaneous, and articular manifestations. Hydroxychloroquine has relatively few side effects, and there is evidence that it improves survival among people who have SLE and stopping HCQ in stable SLE patients led to increased disease flares in Canadian lupus patients. Disease-modifying antirheumatic drugs (DMARDs) are oftentimes used off-label in SLE to decrease disease activity and lower the need for steroid use. DMARDs commonly in use are methotrexate and azathioprine. In more severe cases, medications that aggressively suppress the immune system (primarily high-dose corticosteroids and major immunosuppressants) are used to control the disease and prevent damage. Cyclophosphamide is used for severe glomerulonephritis, as well as other life-threatening or organ-damaging complications, such as vasculitis and lupus cerebritis. Mycophenolic acid is also used for treatment of lupus nephritis, but it is not FDA-approved for this indication.

Depending on the dosage, people who require steroids may develop Cushing's symptoms of truncal obesity, purple striae, buffalo hump and other associated symptoms. These may subside if and when the large initial dosage is reduced, but long-term use of even low doses can cause elevated blood pressure, glucose intolerance (including metabolic syndrome and/or diabetes), osteoporosis, insomnia, avascular necrosis and cataracts.

Numerous new immunosuppressive drugs are being actively tested for SLE. Rather than suppressing the immune system nonspecifically, as corticosteroids do, they target the responses of individual types of immune cells. Belimumab, or a humanized monoclonal antibody against B-lymphocyte stimulating factor (BlyS or BAFF), is FDA approved for lupus treatment and decreased SLE disease activity, especially in patients with baseline elevated disease activity and the presence of autoantibodies. Addition drugs, such as abatacept, epratuzimab, etanercept and others, are actively being studied in SLE patients and some of these drugs are already FDA-approved for treatment of rheumatoid arthritis or other disorders. Since a large percentage of people with SLE suffer from varying amounts of chronic pain, stronger prescription analgesics (pain killers) may be used if over-the-counter drugs (mainly nonsteroidal anti-inflammatory drugs) do not provide effective relief. Potent NSAIDs such as indomethacin and diclofenac are relatively contraindicated for patients with SLE because they increase the risk of kidney failure and heart failure.

Moderate pain is typically treated with mild prescription opiates such as dextropropoxyphene and co-codamol. Moderate to severe chronic pain is treated with stronger opioids, such as hydrocodone or longer-acting continuous-release opioids, such as oxycodone, MS Contin, or methadone. The fentanyl duragesic transdermal patch is also a widely used treatment option for the chronic pain caused by complications because of its long-acting timed release and ease of use. When opioids are used for prolonged periods, drug tolerance, chemical dependency, and addiction may occur. Opiate addiction is not typically a concern, since the condition is not likely to ever completely disappear. Thus, lifelong treatment with opioids is fairly common for chronic pain symptoms, accompanied by periodic titration that is typical of any long-term opioid regimen.

Intravenous immunoglobulins may be used to control SLE with organ involvement, or vasculitis. It is believed that they reduce antibody production or promote the clearance of immune complexes from the body, even though their mechanism of action is not well-understood. Unlike immunosuppressives and corticosteroids, IVIGs do not suppress the immune system, so there is less risk of serious infections with these drugs.

Avoiding sunlight is the primary change to the lifestyle of SLE sufferers, as sunlight is known to exacerbate the disease, as is the debilitating effect of intense fatigue. These two problems can lead to patients becoming housebound for long periods of time. Drugs unrelated to SLE should be prescribed only when known not to exacerbate the disease. Occupational exposure to silica, pesticides and mercury can also make the disease worsen.

Renal transplants are the treatment of choice for end-stage renal disease, which is one of the complications of lupus nephritis, but the recurrence of the full disease in the transplanted kidney is common in up to 30% of patients.

Antiphospholipid syndrome is also related to the onset of neural lupus symptoms in the brain. In this form of the disease the cause is very different from lupus: thromboses (blood clots or "sticky blood") form in blood vessels, which prove to be fatal if they move within the blood stream. If the thromboses migrate to the brain, they can potentially cause a stroke by blocking the blood supply to the brain. If this disorder is suspected in patients, brain scans are usually required for early detection. These scans can show localized areas of the brain where blood supply has not been adequate. The treatment plan for these patients requires anticoagulation. Often, low-dose aspirin is prescribed for this purpose, although for cases involving thrombosis anticoagulants such as warfarin are used.

B. Pharmaceutical Formulations and Delivery

Where therapeutic applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrases "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. Such routes include oral, nasal, buccal, rectal, vaginal or topical route. Alternatively, administration may be by orthotopic, intradermal, subcutaneous, intramuscular, intraperitoneal, or intravenous injection. Such compositions would normally be administered as pharmaceutically acceptable compositions.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," $15^{th}$ Ed., 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

V. KITS

For use in the applications described herein, kits are also within the scope of the invention. Such kits can comprise a carrier, package or container that is compartmentalized to receive one or more containers such as vials, tubes, and the like, each of the container(s) comprising one of the separate elements to be used in the method, in particular, a Bright inhibitor. The kit of the invention will typically comprise the container described above and one or more other containers comprising materials desirable from a commercial end user standpoint, including buffers, diluents, filters, and package inserts with instructions for use. In addition, a label can be provided on the container to indicate that the composition is used for a specific therapeutic application, and can also indicate directions for either in vivo or in vitro use, such as those described above. Directions and or other information can also be included on an insert which is included with the kit. In particular, kits according to the present invention contemplate the assemblage of agents for assessing levels of the biomarkers discussed above along with one or more of an SLE therapeutic and/or a reagent for assessing anti-nuclear antibody (ANA) testing and/or anti-extractable nuclear antigen (anti-ENA), as well as controls for assessing the same.

VI. EXAMPLES

The following examples are included to further illustrate various aspects of the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Study Population.

Experiments were performed in accordance with the Helsinki Declaration and approved by the Institutional Review Boards of the Oklahoma Medical Research Foundation and the University of Oklahoma Health Sciences Center. Study participants were enrolled in the SLE Influenza Vaccination Cohort (Crowe et al., 2011) after written informed consent. Female EA SLE patients (meeting ≥4 ACR classification criteria; Hochberg, 1997) with disease flare 6-12 weeks post-vaccination (age 47.0±13.5 years, n=28) were matched by age (±5 years), race, gender, and time of disease assessment to patients with stable disease (age 46.8±11.9 years, n=28), as well as unrelated healthy controls (age 46.8±13.5 years, n=28). Samples from 13 SLE patients pre-flare were compared to samples drawn from the same individuals in a different year with no flare.

Clinical Data and Sample Collection.

Demographic and clinical information were collected as previously described, including humoral response to influenza vaccination, disease activity, and SELENA-SLEDAI defined flare; severe flares were uncommon and not assessed independently (Crowe et al., 2011). Patients were evaluated at baseline/pre-vaccination and 6 and 12 weeks post-vaccination for disease activity by SELENA-SLEDAI (Crowe et al., 2011). Blood was collected from each participant before vaccination, and at 2, 6, and 12 weeks after vaccination. Plasma was isolated and stored at −20° C. until further use.

Soluble Analyte Determination.

Plasma levels of BLyS (R&D Systems, Minneapolis, Minn.) and APRIL (eBioscience/Affymetrix, San Diego, Calif.) were determined by enzyme-linked immunosorbent assay (ELISA), per the manufacturer protocol. An additional fifty analytes, including innate and adaptive cytokines, chemokines, and soluble TNFR superfamily members (Supplementary Table 1) were assessed by xMAP® multiplex assays (Panomics/Affymetrix, Santa Clara, Calif.) (Stringer et al., 2013). Data were analyzed on the Bio-Rad BioPlex 200® array system (Bio-Rad Technologies, Hercules, Calif.), with a lower boundary of 100 beads per sample/analyte. Median fluorescence intensity for each analyte was interpolated from 5-parameter logistic nonlinear regression standard curves. Analytes below the detection limit were assigned a value of 0.001 pg/mL. Well-specific validity was assessed by ASSAYCHEX™ QC microspheres (Radix Bio-Solutions, Georgetown, Tex., USA) to evaluate non-specific binding. A known control serum was included on each plate (Cellgro human AB serum, Cat#2931949, L/N#M1016). Mean inter-assay coefficient of variance (CV) of multiplexed bead-based assays for cytokine detection has previously been shown to be 10-14% (Dupont et al., 2005 and Dossus et al., 2009), and a similar average CV (10.5%) across the analytes in this assay was obtained using healthy control serum. Intra-assay precision of duplicate wells averaged <10% CV in each 25-plex assay.

Statistical Analysis.

Concentrations of plasma mediators were compared between pre-flare SLE patients and matched non-flare patients or self non-flare samples by Wilcoxon matched-pairs test and adjusted for multiple comparisons using the False Discovery Rate (FDR) via the Benjamini-Hochberg procedure (using R version 2.15.3). Differences between pre-flare patients, matched non-flare patients or self non-flare samples, and matched healthy controls were determined by Friedman test with correction by Dunn's multiple comparison. Except where noted, analyses were performed using GraphPad Prism 6.02 (GraphPad Software, San Diego, Calif.).

For descriptive analyses of soluble mediator data as continuous variables, a Z-score was calculated using the formula:

$$\text{(observed value)} - \text{(mean value of SLE patients with stable disease)}/\text{(standard deviation of SLE patients with stable disease)}$$

See (Sokolove et al., 2012). Normalized values represent the standard deviations above/below the mean for SLE patients with stable disease. Z-scores were used because of the differing magnitudes and variances between levels of cytokines. Without standardization the analyses are dominated by numerical differences rather than comparative differences in cytokine level.

To compare the overall level of inflammation in pre-flare vs. non-flare SLE patients (at baseline/pre-vaccination) in relationship to disease activity at flare (post-vaccination), a soluble mediator score was derived by the cumulative contribution of all pre-flare 52 plasma mediators assessed in relationship to SELENA-SLEDAI disease activity at flare, following an approach previously used for rheumatoid arthritis (Hughes-Austin et al., 2012). Briefly, the concentration of all 52 plasma analytes were log-transformed and standardized (using the mean and SD of all SLE patients). Spearman coefficients of each analyte were generated from a linear regression model testing associations between the flare SELENA-SLEDAI disease activity scores and each pre-flare soluble mediator. The transformed and standardized soluble mediator levels were weighted by the respective Spearman coefficients and summed for a total soluble mediator score (Hughes-Austin et al., 2012). By generating the weights, the pre-flare inflammatory mediators that explained the most variance in their associations with disease activity scores at flare contributed most to the score and therefore the overall level of inflammation resulting in disease flare.

Example 2—Results

Inflammatory Mediators and Regulatory Cytokines are Altered Prior to SLE Disease Flare.

SLE patients within this cohort were followed longitudinally and evaluated for evidence for SELENA-SLEDAI disease flare. The inventors hypothesized that clinical changes in disease activity are the result of a perturbation in the already dysregulated immune system of SLE patients. To test whether markers of immune dysregulation might precede clinical disease flares, 52 soluble analytes were compared in 28 EA SLE patients in whom flare was detected after influenza vaccination, matched SLE patients who did not experience flare for at least 12 weeks post-vaccination, and matched healthy individuals. All SLE patients, with or without subsequent flare, had similar SELENA-SLEDAI scores at baseline (3.8±3.7 flare vs. 2.6±3.2 non-flare [NF], p=0.2451 by Wilcoxon matched-pairs test).

At baseline and follow-up, non-flare SLE patients had levels of T cell mediators that were similar to those in healthy controls, despite significantly higher levels of cytokines from antigen presenting cells (APC), including IL-12, IL-5, IL-6, and IL-23 (FIGS. 6A-C). However, in those who later experienced a flare, baseline levels of several proinflammatory mediators were increased (FIGS. 1A-G), including Th1-, Th2-, and Th17-type cytokines (FIGS. 1A-C and Supplementary Table 2). Patients with impending flare also had higher baseline levels of IP-10, MCP-1, and MCP-3 (FIG. 1D), as well as IL-8 and soluble ICAM-1 (FIG. 6H). While levels of soluble TNF receptors TNFRI and TNFRII and CD40L were increased in all SLE patients compared to healthy controls (FIG. 6E), baseline levels of several soluble TNF superfamily members, including TNFRI, TNFRII, TNF-α, Fas, FasL, and CD40L, were significantly higher in patients with subsequent flare compared to non-flare patients (FIG. 1E and Supplementary Table 2).

In contrast to proinflammatory mediators, regulatory cytokines were higher in stable SLE patients compared to patients with subsequent flare and healthy controls. At baseline and follow-up, patients with no flare within 12 weeks had higher levels of regulatory cytokines IL-10 and TGF-β and chemokine SDF-1 compared to both SLE patients with subsequent flare (FIG. 1F) and healthy controls (FIG. 6F). Furthermore, the balance between inflammatory (IL-1α and IL-1β) and regulatory (IL-1 receptor antagonist; IL-1RA) IL-1 family cytokines was significantly altered. IL-1 receptor antagonist (IL-1RA) downregulates IL-1 mediated immune activation, binding to IL-1 receptor type I (IL-1R1) and preventing binding of IL-1 and subsequent signaling through the receptor (reviewed in Arend, 2002). Plasma levels of IL-1α and IL-1β were significantly higher in pre-flare compared to non-flare SLE patients (FIG. 1G and FIG. 6H), while non-flare patients had a 2-3 fold mean increase in plasma IL-1RA compared to SLE patients with flare (FIG. 1G and Supplementary Table 2) and healthy individuals (FIG. 6G). IL-1RA levels were similar in pre-flare patients and matched healthy controls (FIG. 6G). Given that an increased circulating IL-1RA:IL-1β ratio would favor an anti-inflammatory state (Arend 2002), the mean 2.5- and 3.2-fold increase in IL-1RA:IL-1β ratio in non-flare patients compared to pre-flare SLE patients (FIG. 1G) and healthy individuals (FIG. 6G), respectively, implicates a role for an anti-inflammatory state in stable periods of SLE.

Plasma Mediator Patterns Differ in the Same Patient During Stable Vs. Pre-Flare Periods.

Of the 28 patients with impending flare, 13 participated in the study in multiple years and had at least one flare and one non-flare year. No significant difference in baseline SELENA-SLEDAI scores preceded a flare compared to an observed non-flare period in the same patients (3.0±4.3 flare vs. 2.9±2.0 self non-flare [SNF], p=0.7065 by Wilcoxon matched-pairs test). In contrast, and consistent with the results above, levels of several inflammatory mediators varied between pre-flare and non-flare periods (FIGS. 2A-G and Supplementary Table 3). Impending flares were associated with increased Th1, Th2, and Th17 (FIGS. 2A-C) type cytokines, compared to both self non-flare and matched healthy control samples (Supplementary FIGS. 2A-C). In addition, levels of plasma IP-10, MCP-1 and MCP-3 (FIG. 2D), along with IL-8 and ICAM-1 (FIG. 7H), were significantly elevated in pre-flare periods compared to periods of stable disease. Levels of T-lymphocyte secreted IL-2, IFN-γ, IL-5, IL-13, and the Th17-type cytokines were similar in healthy controls and SLE patients during non-flare periods (FIGS. 7A-C), while APC-secreted IL-12 and IL-6 were higher in SLE patients in both pre-flare and non-flare periods compared to matched healthy controls (FIGS. 7A-C).

Figure 2:
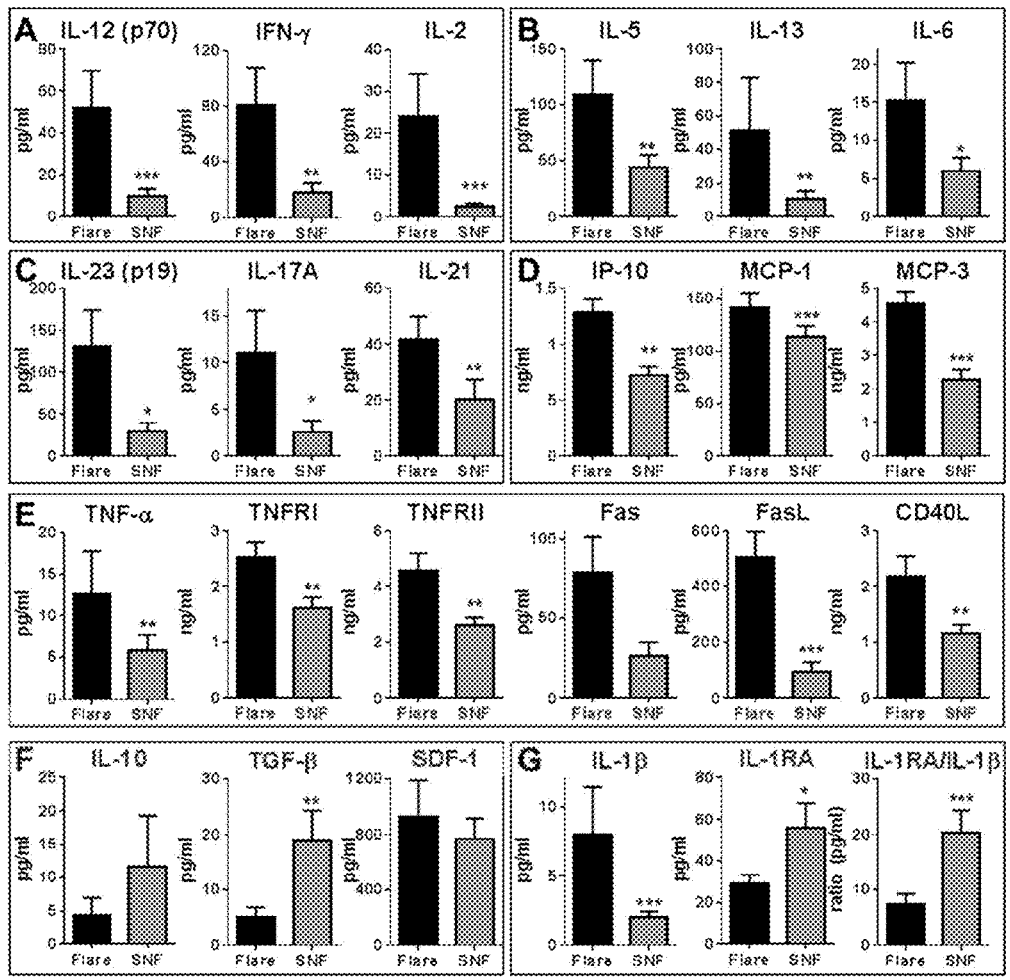
FIGS. 2A-G. SLE patients have altered baseline mediators in adaptive immunity pathways and soluble TNF superfamily members during pre-flare periods compared to the same patients during non-flare periods. Plasma was procured at baseline from 13 SLE patients who exhibited disease flare 6 to 12 weeks later (black bar) and from the same patients in a separate year of the study when they did not exhibit disease flare (SNF, gray bar). Plasma Th1—(FIG. 2A), Th2—(FIG. 2B), and Th17—(FIG. 2C) type cytokines, as well as chemokines (FIG. 2D), soluble TNF superfamily members (FIG. 2E), regulatory mediators (FIG. 2F), and IL-1RA:IL-1β ratio (FIG. 2G) were measured (mean±SEM). Significance was determined by Wilcoxon matched-pairs test. *p<0.05, p<0.01, *p<0.001, ****p, 0.0001.

During non-flare periods, levels of soluble TNF-α and Fas in SLE patients were similar to matched healthy controls, while TNFRI, TNFRII, FasL, and CD40L were persistently elevated in SLE patients regardless of impending flare (FIG. 7F). Compared to periods of stable disease, pre-flare periods were marked by increases in soluble TNF-α and sFas and further increases in TNFRI, TNFRII, FasL, and CD40L (FIG. 2E and Supplementary Table 3). Levels of SDF-1 were similar during pre-flare and non-flare periods. TGF-β significantly decreased during pre-flare periods, but the apparent decrease in IL-10 levels was not significant (FIG. 2F). A significant pre-flare increase in IL-1β and decrease in IL-1RA resulted in a 2.7-fold decrease in the IL-1RA:IL-1β ratio compared to stable periods in the same patient (FIG. 2G). Thus, when followed longitudinally, an altered balance of proinflammatory and regulatory cytokines precedes SLE flares.

Not all Inflammatory Mediators Increase Prior to Flare.

Figure 3:
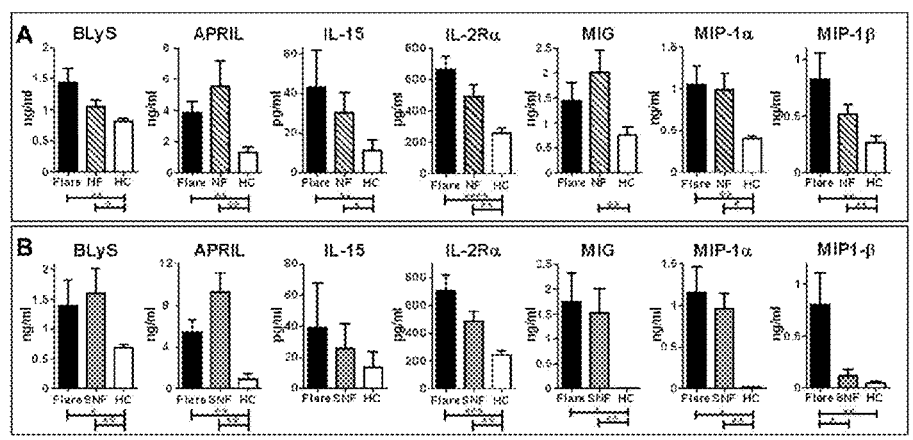
FIGS. 3A-B. Soluble mediators of inflammation in SLE patients which are elevated compared to healthy controls, but which do not discriminate between impending disease flare and non-flare. Plasma levels of BLyS, APRIL, IL-15, IL-2Rα, MIG, MIP-1α, and MP-1β were measured and compared between (FIG. 3A) pre-flare SLE patients (black bar), matched non-flare SLE patients (NF, striped bar), and matched healthy controls (HC, white bar) or (FIG. 3B) SLE patients during a pre-flare period (black bar), the same SLE patients during a non-flare period (SNF, gray bar), and matched healthy controls (HC, white bar). Data are shown as mean±SEM; significance between SLE patients (Flare and NF/SNF) and HC was determined by Wilcoxon matched-pairs test. *p<0.05, p<0.01, *p<0.001, ****p, 0.0001

BLyS and APRIL, TNFR superfamily ligands that support B cell survival, differentiation and autoantibody production (Chu et al., 2009), were increased in SLE patients compared to healthy controls at baseline (FIGS. 3A-B) and follow-up (data not shown). However, levels of these mediators were not different between pre-flare and non-flare patients in this study. Levels of IL-15 and IL-2Rα (CD25), along with MIG, MIP-1α, and MIP1-β, were also similar between both groups of SLE patients and higher in SLE patients than healthy controls (FIGS. 3A-B).

A Weighted Global Soluble Mediator Score Correlates with Impending Flare.

Figure 4:
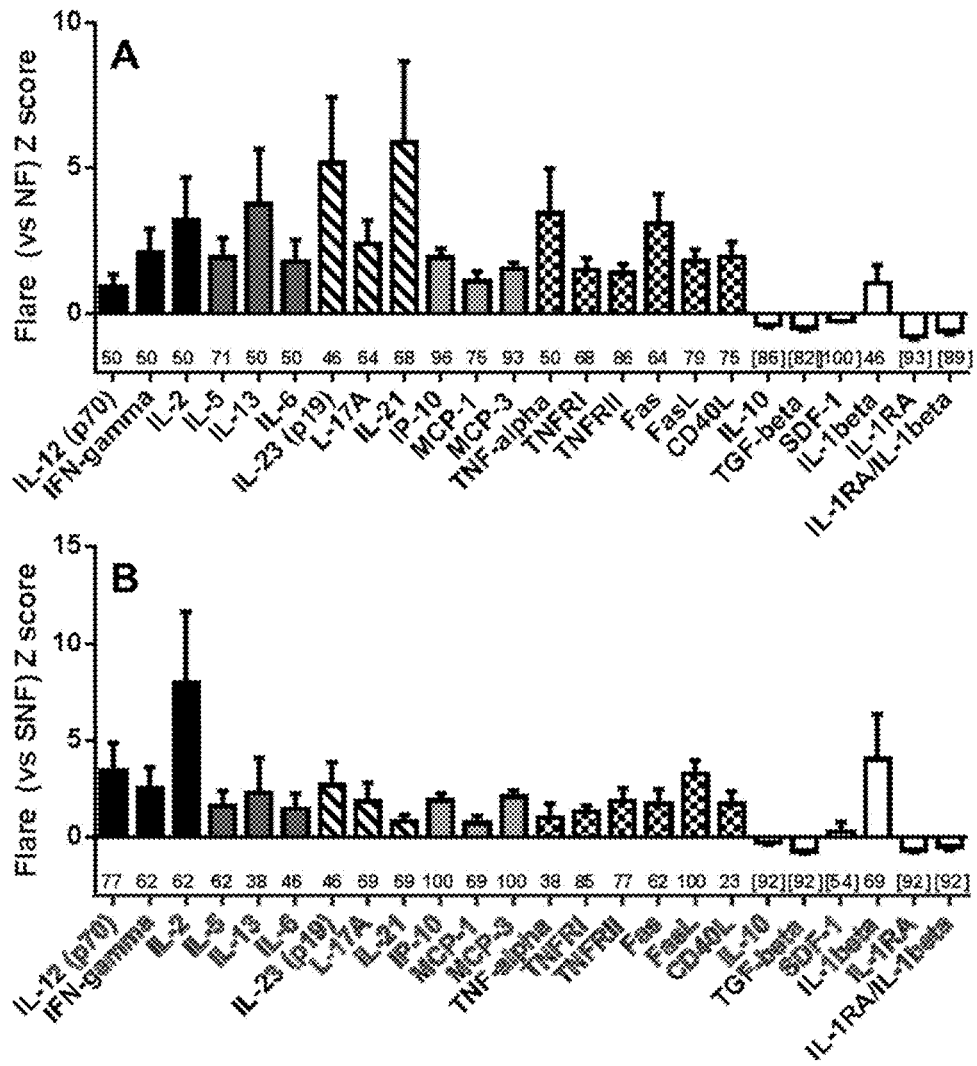
FIGS. 4A-B. Positive inflammatory and negative regulatory mediator Z-scores in SLE patients with impending disease flare. A Z-score was determined for each mediator for (FIG. 4A) each of 28 pre-flare SLE patients, relative to the set of 28 non-flare SLE patients (NF) or (FIG. 4B) each of 13 SLE patients during a non-flare period, relative to the set of the same 13 SLE patients during a non-flare period (SNF). Z-scores were determined for Th1—(black bar), Th2—(dark gray bar), and Th17—(striped bar) type cytokines, as well as chemokines (light gray bar), TNF receptor superfamily members (checkered bar), and regulatory cytokines (white bar (negative score) and crosshatched bar (positive score)). The percent of SLE patients with impending disease flare with a positive or negative (bracketed) z-score for each cytokine is presented numerically.

Despite observed differences in individual inflammatory vs. regulatory plasma mediators in SLE patients with impending flare, due to differing magnitudes and variances of response in soluble mediator levels, it is difficult to compare the contribution of each mediator to impending flare status relative to the other analytes tested. To perform a standardized comparison of mediator levels, a z-score was calculated for each analyte (FIGS. 4A-B). Comparing pre-flare and non-flare SLE patients (FIG. 4A) or comparing the same patients during pre-flare and stable periods (FIG. 4B). Z-scores for inflammatory and regulatory mediators discriminated SLE patients with impending disease flare vs. non-flare. Although adaptive Th mediators were heterogeneous in magnitude and percentage of positive z-scores, a high percentage of pre-flare SLE patients had positive z-scores for these mediators, particularly IP-10 and MCP-3 (FIGS. 4A-B). Of the TNFR superfamily members, TNFRI, TNFRII, and FasL had the highest percentage of pre-flare SLE patients with a positive z-score. The percentage of negative z-scores for regulatory mediators, including IL-10 and TGF-β, as well as the IL-1 family negative regulator IL-1RA, was particularly striking (FIGS. 4A-B). The high percentage of negative z-scores for the IL-1RA:IL-1β ratio further underscored the pro-inflammatory state of pre-flare SLE patients.

To determine the correlation and relative contribution of pre-flare inflammatory and regulatory soluble analytes to SLE disease flare risk, the inventors developed a combined soluble mediator score based on a previously described approach used to identify individuals at increased risk of developing rheumatoid arthritis (Hughes-Austin et al., 2012.). This weighted score gives more impact to those pre-flare analytes with stronger associations to disease activity at time of flare (Supplementary Tables 2-3, center panel). Twenty-eight of 52 pre-flare analytes assessed, as well as the IL-1RA:IL-β ratio, were significantly altered in SLE patients with impending flare compared to matched, non-flare patients, or the same patients during a non-flare period (with 25/52 significant after controlling for false discovery rate; Supplementary Tables 2-3, far left panel).

In order to compare the overall state of immune dysregulation between SLE patients and to assess the potential risk of impending disease flare, a soluble analyte score was derived from the cumulative contribution of log-transformed and standardized pre-flare soluble mediator levels weighted by their respective correlation coefficients of SELENA-SLEDAI disease activity scores at the time of flare (Hughes-Austin et al., 2012.). A distinct advantage of this approach is that it does not require cut-offs for each cytokine/chemokine to establish positivity. The soluble mediator score discriminated SLE patients with impending flare from stable patients (median soluble mediator score 4.14 [pre-flare] vs. −1.70 [non-flare], p<0.0001; Table 1A and FIG. 8A) and from the same patients during non-flare periods (median soluble analyte score 7.41 [pre-flare] vs. −3.09 [self non-flare], p=0.0002; Table 1B and FIGS. 8B-C). Compared to stable patients or to non-flare periods in the same patients, pre-flare patients were 13.8 or 11.1 times more likely, respectively, to have a positive soluble analyte score (Tables 1A-B).

The Global Soluble Mediator Score and Altered Inflammatory and Regulatory Cytokines are Confirmed in a Second Group of SLE Patients.

In order to validate that the soluble mediator score described above can differentiate SLE patients with impending disease flare from either unique SLE patients or the same SLE patients during a period of non-flare (over longitudinal samples), a confirmatory group of 31 SLE patients with disease activity data and plasma samples available six or twelve weeks prior to disease flare were selected (13 pre-flare SLE patients vs. age (±5 years)/race/gender-matched non-flare/NF SLE patients (Table 5A) and 18 pre-flare SLE patients vs. samples during a comparable period of non-flare/SNF in the same SLE patient (Table 5B)). The soluble mediator score discriminated SLE patients with impending flare from stable patients (median soluble mediator score 7.41 (pre-flare) vs. −8.46 (non-flare), p<0.0001; Table 5A and FIG. 12A) and from the same patients during non-flare periods (median soluble analyte score 4.09 (pre-flare] vs. −4.01 (self non-flare), p<0.0001; Table 5B and FIGS. 12B-C) in the validation group. Compared to stable patients or to non-flare periods in the same patients, pre-flare patients were 729 or 164 times more likely, respectively, to have a positive soluble analyte score (Tables 5A-B) in the validation group.

Similar to the altered soluble mediators detected in the initial group of pre-flare SLE patients, alterations in inflammatory and regulatory mediators were noted in the confirmatory group of pre-flare SLE patients (vs. NF SLE patients or SNF time points in the same SLE patients, FIGS. 9-11 and 13-14). Whether compared to NF SLE patients (FIGS. 9, 11, and 13) or a comparable SNF period in the same SLE patients (FIGS. 10-11 and 14), pre-flare SLE patients had increased soluble mediators in multiple immune pathways, including Th1 (FIGS. 9A, 10A, 13A, and 14A), Th2 (FIGS. 9B, 10B, 13B, and 14B), Th17 (FIGS. 9C, 10C, 13C, and 14C), inflammatory chemokines (FIGS. 9D, 10D, 13D, and 14D) and TNF-R superfamily members (FIGS. 9E, 10E, 13E, and 14E). In addition, SLE patients during a period of stable disease (NF or SNF) had higher levels of plasma regulatory mediators, including the adaptive regulatory mediators IL-10 and TGF-β (FIGS. 9F, 10F, 13F, and 14F).

Additional innate mediators, including IFN-α, IFN-β, and IL-1α were significantly higher in pre-flare SLE patients (compared to NF SLE patients (FIG. 13H), p<0.05, or the same SLE patient during a SNF period (FIG. 14H), p<0.05) in the confirmatory group. As was the case in the initial group of pre-flare SLE patients, multiple pre-flare soluble mediators correlated with disease activity at time of disease flare in the confirmatory group (Tables 6-7) and significantly contributed to the soluble mediator score that differentiates SLE patients with impending flare from SLE patients with stable disease (Tables 6-7).

TABLE 1

Association between Soluble Mediator Score and SLE Disease Activity

| | | Soluble Mediator Score | | | | | |
|---|---|---|---|---|---|---|---|
| | | Median | SD | p value[a] | OR[b] | 95% CI | P value[c] |
| A. | Flare subjects (n = 28) | 4.14 | 4.40 | <0.0001 | 13.8 | 3.79 to 50.2 | <0.0001 |
| | NF subjects (n = 28) | −1.70 | 4.64 | | | | |
| B. | Flare subjects (n = 13) | 7.41 | 8.12 | 0.0002 | 11.1 | 1.79 to 68.9 | 0.0469 |
| | SNF subjects (n = 13) | −3.09 | 8.47 | | | | |

A - SLE patients with flare vs. non-flare [NF] post-vaccination)
B - SLE patients with flare vs. a self non-flare (SNF) period
[a]Wilcoxon Matched-Pairs test (2-tailed)
[b]Odds Ratio (# of Flare vs. NF [or SNF] subjects with positive or negative soluble analyte score)
[c]Fisher's Exact test (2-tailed)

TABLE 2

Soluble Mediators Tested in SLE and Control Plasma

Innate
IL-1-α
IL-1β
IL-1RA
IFN-α
IFN-β
G-CSF
Homeostasis
IL-7
IL-15
Other
LIF
PAI-1
PDGF-BB
Resistin
Leptin
SCF
IL-2RA
Th1-like
IL-12 (p70)
IFN-γ
IL-2
Th-17 like
IL-17A
IL-21
IL-23
IL-6
Th2-like
IL-4
IL-5
IL-13

TABLE 2-continued

| Soluble Mediators Tested in SLE and Control Plasma |
|---|
| Regulatory |
| IL-10 |
| TGF-β |
| NGF/TNFR Superfamily |
| BLyS* |
| APRIL* |
| sCD40L |
| sFas |
| sFasL |
| TNF-α |
| TNFRI (p55) |
| TNFRII (p75) |
| TRAIL |
| NGFβ |
| Chemokine/Adhesion molecules |
| IL-8/CXCL8 |
| IP-10/CXCL10 |
| RANTES/CCL5 |
| MIP-1α/CCL3 |
| MIP-1β/CCL4 |
| MCP-1/CCL2 |
| MCP-3/CCL7 |
| GROα/CXCL1 |
| SDF-1/CXCL12 |
| MIG/CXCL9 |
| Eotaxin/CCL11 |
| ICAM-1 |
| VCAM-1 |
| sE-selectin |
| VEGF-A |

*assessed by ELISA

TABLE 3

Soluble Mediators in Flare vs. Non-Flare SLE Patients

| Analyte | Pre-flare Concentration (pg/ml) | | | | | Pre-flare Mediator vs. SELENA-SLEDAI score (at Flare) | | | | Soluble Mediator Score Component | | | | | | |
|---|---|---|---|---|---|---|---|---|---|---|---|---|---|---|---|---|
| | Flare mean | SEM | NF mean | SEM | p value[a] | q value[b] | Spearman r | 95% CI | P value[c] | Flare mean | SD | NF mean | SD | Or[d] | 95% CI | P value[e] |
| Fas | 118.01 | 34.69 | 14.26 | 6.36 | 0.001 | 0.006 | 0.4077 | 0.1544 to 0.6107 | 0.0018 | 0.1840 | 0.3842 | -0.1840 | 0.3475 | 6.25 | 1.96 to 19.9 | 0.0229 |
| IL-1β | 5.46 | 1.79 | 2.31 | 0.55 | 0.019 | 0.045 | 0.2737 | 0.0086 to 0.5066 | 0.0412 | 0.0114 | 0.2580 | -0.0114 | 0.2916 | 1.67 | 0.53 to 5.28 | 0.5629 |
| IL-2 | 27.99 | 10.41 | 4.90 | 1.35 | 0.020 | 0.045 | 0.3695 | 0.1102 to 0.5815 | 0.0051 | 0.0837 | 0.3578 | -0.0837 | 0.3681 | 1.88 | 0.62 to 5.69 | 0.4032 |
| IL-4 | 11.01 | 1.77 | 16.32 | 3.96 | 0.578 | 0.658 | 0.2032 | -0.0710 to 0.4483 | 0.1331 | 0.0127 | 0.1075 | -0.0127 | 0.2687 | 1.17 | 0.39 to 3.55 | 1.0000 |
| IL-5 | 90.54 | 19.18 | 35.91 | 5.35 | 0.002 | 0.008 | 0.2522 | -0.0195 to 0.4892 | 0.0507 | 0.0800 | 0.2898 | -0.0300 | 0.2343 | 1.67 | 0.53 to 5.28 | 0.5619 |
| IL-6 | 21.22 | 5.41 | 8.11 | 1.38 | 0.050 | 0.094 | 0.2568 | -0.0146 to 0.4929 | 0.0561 | 0.0184 | 0.3326 | -0.0184 | 0.1517 | 1.00 | 0.35 to 2.86 | 1.0000 |
| IL-7 | 67.60 | 19.15 | 32.30 | 12.19 | 0.002 | 0.008 | 0.1137 | -0.1617 to 0.3726 | 0.4042 | 0.0184 | 0.1293 | -0.0184 | 0.0900 | 4.00 | 1.28 to 12.5 | 0.0253 |
| IL-8 | 5.94 | 1.61 | 1.72 | 0.24 | 0.004 | 0.012 | 0.2453 | -0.0257 to 0.4844 | 0.0672 | 0.0271 | 0.2622 | -0.0271 | 0.2252 | 2.25 | 0.72 to 7.01 | 0.2563 |
| IL-10 | 4.67 | 1.34 | 10.72 | 3.05 | 0.091 | 0.134 | 0.0896 | -0.1852 to 0.3515 | 0.5112 | -0.0446 | 0.0823 | 0.0037 | 0.0978 | 1.62 | 0.53 to 4.54 | 0.5731 |
| TGF-β | 9.91 | 2.21 | 20.08 | 4.05 | 0.073 | 0.112 | 0.1210 | -0.1544 to 0.3790 | 0.3743 | -0.0037 | 0.1011 | -0.0057 | 0.1397 | 1.00 | 0.31 to 3.19 | 1.0000 |
| IFN-β | 331.53 | 249.36 | 34.60 | 7.77 | 0.834 | 0.920 | -0.1394 | -0.3919 to 0.1361 | 0.3058 | 0.0328 | 0.1748 | -0.0328 | 0.0825 | 6.25 | 1.52 to 25.7 | 0.0141 |
| IL-12(p70) | 47.54 | 9.80 | 24.24 | 4.60 | 0.001 | 0.006 | 0.2761 | 0.0062 to 0.5085 | 0.0394 | 0.0251 | 0.3485 | -0.0251 | 0.1802 | 1.54 | 0.54 to 4.42 | 0.5932 |
| IL-13 | 40.13 | 16.12 | 7.93 | 1.61 | 0.059 | 0.103 | 0.1767 | -0.0363 to 0.4283 | 0.1876 | 0.0225 | 0.1766 | -0.0225 | 0.1811 | 0.72 | 0.23 to 2.22 | 0.7753 |
| IL-23(p19) | 163.70 | 59.56 | 28.19 | 4.95 | 0.070 | 0.110 | 0.3465 | 0.0841 to 0.5641 | 0.0089 | 0.0355 | 0.3809 | -0.0655 | 0.3051 | 1.16 | 0.40 to 3.32 | 1.0000 |
| IFN-γ | 61.95 | 16.45 | 20.37 | 3.77 | 0.120 | 0.164 | 0.2841 | 0.0148 to 0.5149 | 0.0339 | 0.0892 | 0.1533 | -0.0892 | 0.3528 | 1.67 | 0.53 to 5.28 | 0.5619 |
| TNF-α | 20.90 | 7.31 | 4.60 | 0.89 | 0.008 | 0.020 | 0.3133 | 0.0470 to 0.5381 | 0.0187 | 0.1014 | 0.2015 | -0.1014 | 0.3715 | 1.00 | 0.34 to 2.98 | 1.0000 |
| G-CSF | 14.63 | 3.76 | 6.63 | 2.43 | 0.034 | 0.073 | 0.2776 | 0.0078 to 0.5037 | 0.0383 | 0.0464 | 0.2899 | -0.0454 | 0.2616 | 1.80 | 0.62 to 5.25 | 0.4187 |
| IFN-α | 19.37 | 9.56 | 3.10 | 1.61 | 0.051 | 0.094 | 0.2870 | -0.0571 to 0.4521 | 0.1258 | 0.0683 | 0.2156 | -0.6083 | 0.1751 | 4.00 | 1.28 to 12.5 | 0.0288 |
| IL-1α | 76.85 | 13.30 | 38.38 | 8.33 | 0.002 | 0.008 | 0.2870 | 0.0181 to 0.5173 | 0.0320 | 0.0701 | 0.2115 | -0.0701 | 0.3350 | 1.78 | 0.62 to 5.16 | 0.4218 |
| IL-1RA | 53.99 | 9.00 | 121.71 | 16.77 | <0.0001 | <0.0001 | -0.2630 | -0.5020 to 0.0025 | 0.0458 | 0.1242 | 0.2326 | -0.1242 | 0.2455 | 6.25 | 1.96 to 19.9 | 0.0029 |
| IL-15 | 43.10 | 18.89 | 30.41 | 10.18 | 1.000 | 1.000 | 0.2010 | -0.0733 to 0.4471 | 0.1373 | -0.0124 | 0.2072 | 0.0124 | 0.1976 | 0.74 | 0.25 to 2.17 | 0.7848 |
| IL-21 | 90.45 | 32.26 | 21.57 | 2.20 | <0.0001 | <0.0001 | 0.4239 | 0.1735 to 0.6229 | 0.0011 | 0.0691 | 0.5785 | -0.0691 | 0.1464 | 3.80 | 1.26 to 11.5 | 0.0315 |
| ICAM-1 | 117965.41 | 7238.79 | 65233.03 | 6607.47 | <0.0001 | <0.0001 | 0.3807 | 0.1230 to 0.5903 | 0.0038 | 0.2301 | 0.2194 | -0.2301 | 0.3706 | 17.59 | 4.18 to 74.0 | <0.0001 |
| IL-17A | 11.41 | 2.37 | 4.46 | 0.58 | 0.005 | 0.026 | 0.2450 | -0.0261 to 0.4841 | 0.0677 | 0.0430 | 0.2353 | -0.0430 | 0.2531 | 1.94 | 0.62 to 6.09 | 0.3911 |
| NGF-β | 99.16 | 29.41 | 144.46 | 35.68 | 0.362 | 0.448 | 0.1554 | -0.1200 to 0.4086 | 0.2528 | -0.0023 | 0.1307 | 0.0023 | 0.1792 | 0.47 | 0.16 to 1.40 | 0.2772 |
| Leptin | 25046.06 | 5202.72 | 45704.99 | 6244.91 | 0.002 | 0.008 | -0.1416 | -0.3967 to 0.1333 | 0.2980 | -0.0624 | 0.1437 | 0.0624 | 0.1017 | 4.50 | 1.45 to 13.9 | 0.0151 |
| SCF | 615.58 | 63.48 | 299.68 | 27.14 | <0.0001 | <0.0001 | 0.4385 | 0.1508 to 0.6337 | 0.0007 | 0.1904 | 0.4608 | -0.1904 | 0.3227 | 7.50 | 2.29 to 24.5 | 0.0022 |
| IL-2Rα | 666.72 | 84.10 | 492.55 | 74.83 | 0.050 | 0.094 | 0.3445 | 0.0818 to 0.5625 | 0.0055 | 0.0832 | 0.3273 | -0.0832 | 0.3468 | 2.39 | 0.82 to 6.98 | 0.1810 |
| SDF-1 | 493.30 | 84.69 | 1431.00 | 203.50 | 0.018 | 0.047 | -0.1609 | -0.4133 to 0.1144 | 0.2360 | -0.0692 | 0.0918 | 0.0692 | 0.1925 | 3.46 | 1.11 to 10.7 | 0.0543 |
| MIG | 1442.54 | 363.91 | 2007.84 | 447.56 | 0.132 | 0.175 | 0.0034 | -0.2625 to 0.2781 | 0.9509 | -0.0015 | 0.0082 | 0.0015 | 0.0084 | 0.36 | 0.12 to 1.06 | 0.1078 |

TABLE 3-continued

Soluble Mediators in Flare vs. Non-Flare SLE Patients

| | Pre-flare Concentration (pg/ml) | | | | | | Pre-flare Mediator vs. SELENA-SLEDAI score (at Flare) | | | | Soluble Mediator Score Component | | | | | |
|---|---|---|---|---|---|---|---|---|---|---|---|---|---|---|---|---|
| Analyte | Flare mean | SEM | NF mean | SEM | P value[a] | q value[b] | Spearman r | 95% CI | P value[c] | Flare mean | SD | NF mean | SD | Or[d] | 95% CI | P value[e] |
| MIP-1α | 1045.48 | 231.84 | 989.44 | 199.72 | 0.678 | 0.735 | 0.0960 | −0.1790 to 0.3571 | 0.4815 | −0.0014 | 0.1021 | 0.0014 | 0.0914 | 1.16 | 0.40 to 3.32 | 1.0000 |
| MCP-3 | 3926.00 | 281.30 | 1907.21 | 246.21 | <0.0001 | <0.0001 | 0.4243 | 0.1739 to 0.6232 | 0.0011 | 0.2013 | 0.3480 | −0.2013 | 0.4020 | 12.83 | 3.12 to 53.2 | 0.0002 |
| PAI-1 | 11973.53 | 1473.37 | 11027.44 | 1665.52 | 0.425 | 0.514 | 0.2359 | −0.0358 to 0.4759 | 0.0801 | 0.0126 | 0.2522 | −0.0126 | 0.2223 | 1.34 | 0.46 to 3.87 | 0.7875 |
| FasL | 455.10 | 58.30 | 193.83 | 27.38 | 0.0002 | 0.002 | 0.3981 | 0.1432 to 0.6035 | 0.0024 | 0.2022 | 0.2894 | −0.2022 | 0.3928 | 3.86 | 1.26 to 11.8 | 0.0306 |
| IP-10 | 1233.17 | 89.37 | 668.14 | 58.37 | <0.0001 | <0.0001 | 0.4151 | 0.1542 to 0.6171 | 0.0014 | 0.2676 | 0.2795 | −0.2676 | 0.3550 | 13.80 | 3.79 to 50.2 | <0.0001 |
| PDGF-88 | 6070.78 | 1247.68 | 7038.83 | 1697.21 | 0.678 | 0.735 | 0.0037 | −0.2669 to 0.2738 | 0.9784 | −0.0002 | 0.0035 | 0.0002 | 0.0038 | 0.49 | 0.17 to 1.41 | 0.2847 |
| RANTES | 4449.33 | 628.53 | 8611.44 | 1634.84 | 0.008 | 0.020 | −0.1764 | −0.4264 to 0.0987 | 0.1934 | 0.0682 | 0.1639 | −0.0682 | 0.1639 | 2.78 | 0.94 to 8.22 | 0.2078 |
| MIP-1β | 824.79 | 231.91 | 517.56 | 83.75 | 0.695 | 0.737 | −0.0010 | −0.2740 to 0.2657 | 0.9768 | −0.0003 | 0.0042 | 0.0003 | 0.0033 | 0.86 | 0.29 to 2.54 | 1.0000 |
| LIF | 16.22 | 3.91 | 23.24 | 2.83 | 0.063 | 0.105 | −0.0225 | −0.2910 to 0.2494 | 0.8696 | 0.0078 | 0.0238 | −0.0078 | 0.0183 | 3.80 | 1.26 to 11.5 | 0.0315 |
| MCP-1 | 143.85 | 16.23 | 89.89 | 9.06 | 0.003 | 0.011 | 0.3541 | 0.0927 to 0.5699 | 0.0074 | 0.1431 | 0.3288 | −0.1431 | 0.3238 | 5.28 | 1.69 to 16.5 | 0.0069 |
| Eotaxin | 502.39 | 83.84 | 381.39 | 44.35 | 0.104 | 0.150 | 0.2320 | −0.0410 to 0.4727 | 0.0854 | 0.0393 | 0.2205 | −0.0393 | 0.2404 | 1.00 | 0.35 to 2.86 | 1.0000 |
| VEGF | 1271.98 | 859.61 | 413.95 | 153.94 | 0.227 | 0.295 | −0.1318 | −0.3883 to 0.1437 | 0.3329 | 0.0106 | 0.1584 | −0.0106 | 0.1003 | 2.50 | 0.83 to 7.55 | 0.1707 |
| TNFRI | 2062.88 | 210.58 | 1295.65 | 95.93 | 0.001 | 0.005 | 0.3683 | 0.1087 to 0.3808 | 0.0052 | 0.1099 | 0.4230 | −0.1099 | 0.2690 | 2.40 | 0.82 to 7.04 | 0.1799 |
| TRAIL | 10776.55 | 5367.60 | 920.54 | 173.12 | 0.055 | 0.108 | 0.1219 | −0.1535 to 0.3798 | 0.3707 | 0.0238 | 0.1562 | −0.0238 | 0.0585 | 1.83 | 0.62 to 5.42 | 0.4121 |
| TNFRII | 3933.13 | 364.60 | 2249.45 | 227.27 | 0.0003 | 0.002 | 0.4238 | 0.1733 to 0.6228 | 0.0011 | 0.2178 | 0.3594 | −0.2178 | 0.3718 | 7.50 | 2.29 to 24.5 | 0.0011 |
| GRD-α | 145.67 | 20.06 | 202.53 | 19.46 | 0.029 | 0.043 | −0.0826 | −0.3452 to 0.1920 | 0.5450 | 0.0271 | 0.0801 | −0.0271 | 0.0772 | 3.80 | 175 to 11.5 | 0.0315 |
| E-selectin | 6654.90 | 1054.13 | 5875.10 | 1169.84 | 0.109 | 0.154 | −0.1051 | −0.3551 to 0.1700 | 0.4405 | 0.0309 | 0.1090 | −0.0309 | 0.0580 | 1.78 | 0.62 to 5.12 | 0.4230 |
| CD40L | 2112.31 | 350.82 | 764.60 | 130.10 | <0.0002 | <0.0002 | 0.2803 | 0.0108 to 0.5119 | 0.0354 | 0.1251 | 0.2683 | −0.1251 | 0.2357 | 6.33 | 1.97 to 20.3 | 0.0029 |
| Resistin | 6829.88 | 760.92 | 8159.86 | 1112.94 | 0.245 | 0.321 | 0.0147 | −0.2567 to 0.2839 | 0.9145 | −0.0015 | 0.0137 | 0.0015 | 0.0157 | 0.74 | 0.25 to 2.17 | 0.7848 |
| VCAM | 16038.64 | 2323.07 | 17690.47 | 1960.88 | 0.452 | 0.534 | −0.1239 | −0.3825 to 0.1516 | 0.3630 | 0.0137 | 0.1265 | −0.0137 | 0.1220 | 1.55 | 0.54 to 4.45 | 0.5913 |
| BLyS | 1431.47 | 237.33 | 1048.03 | 101.72 | 0.582 | 0.658 | 0.2108 | −0.0532 to 0.4552 | 0.1189 | 0.0303 | 0.2497 | −0.0303 | 0.1621 | 2.50 | 0.83 to 7.55 | 0.1707 |
| APRIL | 3833.97 | 740.04 | 5564.93 | 1625.30 | 0.575 | 0.999 | 0.0465 | −0.2267 to 0.3129 | 0.7338 | −0.0038 | 0.0501 | 0.0038 | 0.0432 | 0.65 | 0.18 to 2.37 | 0.7458 |
| IL-1RA/IL-1β | 24.35 | 6.65 | 62.03 | 12.10 | <0.0002 | N.D. | −0.3497 | −0.3665 to −0.0876 | 0.0083 | 0.1482 | 0.3345 | −0.1432 | 0.3028 | 4.50 | 1.46 to 13.9 | 0.0151 |

[a]Wilcoxon Matched-Pairs test (2-tailed); significant values (p ≤ 0.05) highlighted in yellow
[b]Benjamini-Hochberg multiple testing procedure (False Discovery Rate ≤ 0.05) using R version 2.15.3; significant values (q ≤ 0.05) highlighted in yellow
[c]Spearman Rank Correlation; significant values (p < 0.05) highlighted in blue
[d]Odds Ratio (# of Flare vs. NFSLE patients with positive or negative soluble analyte score component value)
[e]Fisher's Exact test (2-tailed); significant values (p < 0.05) highlighted in green

TABLE 4

Soluble Meidators in Flare v. SNF SLE Samples

| Analyte | Pre-flare Concentration (pg/ml) | | | | | | Pre-flare Mediator vs. SELENA-SLEDAI score (at Flare) | | | | Soluble Mediator Score Component | | | | | |
|---|---|---|---|---|---|---|---|---|---|---|---|---|---|---|---|---|
| | Flare mean | SEM | SNF mean | SEM | p value[a] | q value[b] | Spearman r | 95% CI | P value[c] | | Flare mean | SD | SNF mean | SD | Orc | 95% CI | P value[e] |
| Fas | 78.73 | 22.63 | 526.43 | 8.31 | 0.092 | 0.158 | 0.4594 | 0.0756 to 0.7247 | 0.0182 | | 0.0934 | 0.417 | −0.0934 | 0.4971 | 1.00 | 0.16 to 6.20 | 1.0000 |
| IL-1β | 8.01 | 3.42 | 2.03 | 0.41 | 0.001 | 0.014 | 0.5381 | 0.1787 to 0.7708 | 0.0046 | | 0.1850 | 0.537 | −0.1850 | 0.4911 | 2.63 | 0.53 to 13.1 | 0.4283 |
| IL-2 | 23.99 | 10.11 | 2.46 | 0.75 | 0.001 | 0.014 | 0.5140 | 0.1462 to 0.7569 | 0.0072 | | 0.2263 | 0.354 | −0.2253 | 0.5602 | 3.60 | 0.71 to 18.3 | 0.2377 |
| IL-4 | 9.47 | 1.79 | 7.49 | 2.04 | 0.255 | 0.355 | 0.3616 | −0.0421 to 0.6638 | 0.0695 | | 0.0820 | 0.313 | −0.0820 | 0.4000 | 2.56 | 0.53 to 12.4 | 0.4338 |
| IL-5 | 108.64 | 31.62 | 43.84 | 11.04 | 0.017 | 0.039 | 0.5597 | 0.224 to 0.7887 | 0.0024 | | 0.0113 | 0.796 | −0.0113 | 0.2060 | 10.30 | 1.02 to 10.4 | 0.0730 |
| IL-6 | 15.21 | 5.05 | 5.95 | 1.74 | 0.034 | 0.072 | 0.3802 | −0.0205 to 0.5757 | 0.0553 | | 0.0404 | 0.408 | −0.0404 | 0.3626 | 0.48 | 0.09 to 2.65 | 0.6728 |
| IL-7 | 50.73 | 30.07 | 94.72 | 48.23 | 0.094 | 0.158 | 0.300 | −0.1108 to 0.6233 | 0.1364 | | 0.0307 | 0.295 | −0.0307 | 0.3141 | 1.37 | 0.29 to 6.54 | 1.0000 |
| IL-8 | 5.84 | 1.63 | 1.79 | 0.42 | 0.003 | 0.014 | 0.2992 | −0.1118 to 0.6227 | 0.1376 | | 0.1427 | 0.311 | −0.1427 | 0.2136 | 5.33 | 0.97 to 29.4 | 0.1107 |
| IL-10 | 4.37 | 2.55 | 11.57 | 7.67 | 0.569 | 0.657 | 0.2486 | −0.1675 to 0.5867 | 0.2245 | | 0.0475 | 0.183 | −0.0475 | 0.2971 | 3.44 | 0.53 to 22.4 | 0.3783 |
| TGF-β | 5.11 | 1.78 | 18.95 | 5.35 | 0.015 | 0.045 | 0.2186 | −0.1961 to 0.5670 | 0.2833 | | −0.0605 | 0.228 | 0.0605 | 0.1995 | 0.38 | 0.08 to 1.90 | 0.4283 |
| IFN-β | 25.25 | 14.35 | 14.73 | 8.01 | 0.078 | 0.144 | 0.4109 | 0.0159 to 0.0950 | 0.0370 | | 0.0808 | 0.405 | −0.0808 | 0.4164 | 2.58 | 0.53 to 12.4 | 0.4338 |
| IL-12(p70) | 52.06 | 17.56 | 9.90 | 3.40 | 0.002 | 0.005 | 0.4128 | 0.0181 to 0.8962 | 0.0361 | | 0.0791 | 0.547 | −0.0791 | 0.2053 | 7.50 | 1.31 to 43.0 | 0.0472 |
| IL-13 | 51.69 | 31.23 | 10.48 | 4.90 | 0.002 | 0.019 | 0.4857 | 0.1104 to 0.7409 | 0.0117 | | 0.1480 | 0.394 | −0.1480 | 0.5396 | 1.41 | 0.28 to 7.13 | 1.0000 |
| IL-23(p19) | 130.73 | 43.04 | 29.32 | 10.30 | 0.011 | 0.030 | 0.5549 | 0.2018 to 0.7804 | 0.0033 | | 0.2047 | 0.58 | −0.2047 | 0.4633 | 1.87 | 0.39 to 8.50 | 0.6951 |
| INF-γ | 80.64 | 27.24 | 18.30 | 6.84 | 0.002 | 0.014 | 0.4340 | 0.0439 to 0.7093 | 0.0267 | | 0.1798 | 0.213 | −0.1798 | 0.5164 | 2.63 | 0.53 to 13.1 | 0.4283 |
| TNF-α | 12.53 | 5.29 | 5.82 | 1.87 | 0.007 | 0.030 | 0.5177 | 0.1512 to 0.7591 | 0.0068 | | 0.1115 | 0.563 | −0.1115 | 0.4631 | 1.00 | 0.21 to 4.80 | 1.0000 |
| G-CSF | 13.36 | 5.10 | 10.76 | 9.44 | 0.297 | 0.355 | 0.4366 | 0.0471 to 0.7108 | 0.0258 | | 0.1127 | 0.459 | −0.1127 | 0.3985 | 2.63 | 0.53 to 13.1 | 0.4283 |
| INF-α | 12.73 | 8.38 | 6.19 | 4.31 | 0.297 | 0.355 | 0.3277 | −0.0805 to 0.6417 | 0.1022 | | 0.0935 | 0.338 | −0.0935 | 0.3010 | 3.89 | 0.72 to 21.1 | 0.2262 |
| IL-1α | 56.55 | 15.53 | 13.39 | 2.53 | 0.0002 | 0.005 | 0.5628 | 0.1989 to 0.7792 | 0.0034 | | 0.2547 | 0.586 | −0.2547 | 0.3904 | 3.89 | 0.72 to 21.1 | 0.2262 |
| IL-1RA | 28.50 | 4.31 | 55.92 | 11.70 | 0.022 | 0.045 | 0.1157 | −0.2965 to 0.4908 | 0.5734 | | −0.0272 | 0.073 | 0.0272 | 0.1448 | 0.19 | 0.03 to 1.03 | 0.1107 |
| IL-15 | 38.97 | 28.90 | 25.86 | 15.91 | 0.688 | 0.727 | 0.3821 | −0.0415 to 0.6641 | 0.0691 | | 0.0280 | 0.374 | −0.0280 | 0.3628 | 1.37 | 0.29 to 6.54 | 1.0000 |
| IL-21 | 41.60 | 8.31 | 20.15 | 7.20 | 0.003 | 0.025 | 0.4780 | 0.0991 to 0.7358 | 0.0135 | | 0.0593 | 0.619 | −0.0593 | 0.2923 | 0.42 | 1.00 to 41.2 | 0.0988 |
| ICAM-1 | 108578.24 | 8896.24 | 53713.29 | 10242.34 | 0.0002 | 0.014 | 0.4169 | 0.0231 to 0.6988 | 0.0341 | | 0.2655 | 0.209 | −0.2655 | 0.4011 | 40.00 | 3.58 to 44.7 | 0.0010 |
| IL-17A | 11.13 | 4.45 | 2.52 | 1.28 | 0.002 | 0.084 | 0.5739 | 0.2283 to 0.7910 | 0.0022 | | 0.2818 | 0.42 | −0.2818 | 0.5810 | 12.40 | 1.83 to 83.8 | 0.0154 |
| NGF-β | 49.63 | 12.79 | 52.30 | 12.39 | 0.945 | 0.945 | 0.3124 | −0.0573 to 0.6316 | 0.1202 | | −0.0251 | 0.336 | 0.0251 | 0.2980 | 0.73 | 0.15 to 3.43 | 1.0000 |
| Leptin | 18791.32 | 4971.67 | 43891.24 | 10809.80 | 0.013 | 0.035 | −0.3479 | −0.6550 to 0.0577 | 0.0816 | | −0.1136 | 0.307 | 0.1136 | 0.3606 | 2.56 | 0.53 to 12.4 | 0.4338 |
| SCF | 783.41 | 73.72 | 415.77 | 49.76 | 0.001 | 0.005 | 0.5428 | 0.1851 to 0.7735 | 0.0042 | | 0.3598 | 0.358 | −0.3598 | 0.4529 | 11.10 | 1.79 to 68.9 | 0.0169 |
| IL-2Rα | 706.23 | 114.17 | 487.98 | 70.99 | 0.017 | 0.039 | 0.4201 | 0.0289 to 0.7007 | 0.0326 | | 0.1534 | 0.367 | −0.1534 | 0.4264 | 1.00 | 0.21 to 4.68 | 1.0000 |
| SDF-1 | 268.80 | 113.50 | 249.70 | 113.80 | 0.273 | 0.355 | 0.3078 | −0.1024 to 0.6285 | 0.1260 | | 0.0229 | 0.469 | −0.0229 | 0.3834 | 0.735 | 0.16 to 3.44 | 1.0000 |

TABLE 4-continued

Soluble Meidators in Flare v. SNF SLE Samples

| | Pre-flare Concentration (pg/ml) | | | | | Pre-flare Mediator vs. SELENA-SLEDAI score (at Flare) | | | Soluble Mediator Score Component | | | | | |
|---|---|---|---|---|---|---|---|---|---|---|---|---|---|---|
| Analyte | Flare mean | SEM | SNF mean | SEM | p value[a] | q value[b] | Spearman r | 95% CI | P value[c] | Flare mean | SD | SNF mean | SD | Orc | 95% CI | P value[e] |
| MIG | 1741.82 | 574.77 | 1526.20 | 481.68 | 0.945 | 0.945 | 0.2308 | −0.1837 to 0.5756 | 0.2567 | 0.0125 | 0.232 | −0.0125 | 0.2384 | 0.73 | 0.15 to 3.48 | 1.0000 |
| MIP-1α | 1154.38 | 307.02 | 965.41 | 184.81 | 0.414 | 0.513 | 0.2109 | −0.2038 to 0.5615 | 0.3010 | 0.0048 | 0.242 | −0.0048 | 0.1841 | 0.73 | 0.15 to 3.43 | 1.0000 |
| MCP-3 | 4529.77 | 363.54 | 2271.34 | 297.78 | 0.001 | 0.005 | 0.4560 | 0.0713 to 0.7226 | 0.0192 | 0.3169 | 0.264 | −0.3169 | 0.3820 | 40.00 | 3.58 to 44.7 | 0.0010 |
| PAI-1 | 16030.41 | 2507.20 | 18370.03 | 4762.39 | 0.853 | 0.928 | 0.2622 | −0.1513 to 0.5975 | 0.1957 | −0.0149 | 0.268 | 0.0149 | 0.2665 | 1.00 | 0.21 to 4.68 | 1.0000 |
| FasL | 507.27 | 90.16 | 92.31 | 35.15 | 0.0002 | 0.0050 | 0.4853 | 0.1086 to 0.7401 | 0.0120 | 0.3620 | 0.215 | −0.3620 | 0.4008 | 40.00 | 3.58 to 44.7 | 0.0010 |
| IP-10 | 1287.41 | 111.39 | 718.69 | 81.67 | 0.005 | 0.017 | 0.4274 | 0.0358 to 0.7052 | 0.0294 | 0.2737 | 0.287 | −0.2737 | 0.3687 | 7.50 | 1.31 to 43.0 | 0.0472 |
| PDGF-88 | 7955.58 | 2038.23 | 5183.78 | 604.69 | 0.244 | 0.355 | −0.1471 | −0.5147 to 0.2661 | 0.4733 | −0.0217 | 0.185 | 0.0217 | 0.1000 | 1.00 | 0.21 to 4.86 | 1.0000 |
| RANTES | 3822.87 | 995.56 | 3673.48 | 815.03 | 0.340 | 0.431 | 0.2583 | −0.1553 to 0.5949 | 0.2026 | −0.0097 | 0.287 | 0.0097 | 0.2373 | 0.73 | 0.15 to 3.43 | 1.0000 |
| MIP1-β | 806.02 | 300.32 | 118.10 | 60.86 | 0.002 | 0.014 | 0.2500 | −0.1640 to 0.5891 | 0.2181 | 0.1341 | 0.23 | −0.1341 | 0.1956 | 7.50 | 1.31 to 43.0 | 0.0472 |
| LIF | 7.15 | 1.01 | 9.82 | 2.16 | 0.163 | 0.273 | 0.1362 | −0.2765 to 0.5064 | 0.5072 | −0.0117 | 0.108 | 0.0117 | 0.1634 | 0.73 | 0.15 to 3.48 | 1.0000 |
| MCP-1 | 141.54 | 13.89 | 113.53 | 10.56 | 0.001 | 0.011 | 0.2845 | −0.1276 to 0.6128 | 0.1590 | 0.0858 | 0.28 | −0.0858 | 0.2723 | 3.60 | 0.71 to 18.3 | 0.2377 |
| Eotaxin | 661.07 | 159.16 | 550.32 | 69.89 | 0.455 | 0.550 | 0.2737 | −0.1391 to 0.6054 | 0.1761 | −0.0106 | 0.318 | −0.0106 | 0.2336 | 0.38 | 0.08 to 1.50 | 0.4283 |
| VEGF | 575.04 | 436.33 | 358.62 | 236.66 | 0.685 | 0.727 | 0.2210 | −0.1537 to 0.5687 | 0.2779 | 0.0071 | 0.237 | −0.0071 | 0.2127 | 0.52 | 0.10 to 2.58 | 0.6882 |
| TNFRI | 2534.61 | 267.16 | 1604.96 | 197.11 | 0.003 | 0.025 | 0.5187 | 0.1526 to 0.7597 | 0.0066 | 0.2294 | 0.517 | −0.2294 | 0.4236 | 18.30 | 2.52 to 13.3 | 0.0048 |
| TRAIL | 22588.03 | 10857.20 | 13627.54 | 7721.25 | 0.588 | 0.679 | 0.0750 | −0.3326 to 0.4589 | 0.7159 | 0.0058 | 0.084 | −0.0058 | 0.0677 | 1.48 | 0.26 to 8.50 | 1.0000 |
| TNFRII | 4550.71 | 657.88 | 2606.88 | 282.64 | 0.017 | 0.039 | 0.5254 | 0.1614 to 0.7635 | 0.0058 | 0.2417 | 0.559 | −0.2417 | 0.3692 | 7.50 | 1.31 to 43.0 | 0.0472 |
| GRD-α | 124.01 | 13.63 | 147.66 | 22.99 | 0.191 | 0.292 | 0.1318 | −0.2806 to 0.5031 | 0.5211 | −0.0116 | 0.103 | 0.0115 | 0.1592 | 0.54 | 0.11 to 2.55 | 0.6951 |
| E-selectin | 3861.51 | 668.22 | 3901.71 | 852.55 | 0.685 | 0.727 | 0.3493 | −0.0531 to 0.6559 | 0.0803 | 0.0209 | 0.312 | −0.0209 | 0.3946 | 1.37 | 0.29 to 6.54 | 1.0000 |
| CD40L | 2173.43 | 383.13 | 1152.51 | 162.68 | 0.003 | 0.014 | 0.2329 | −0.1816 to 0.5771 | 0.2523 | 0.1064 | 0.166 | −0.1054 | 0.2466 | 3.60 | 0.71 to 18.3 | 0.2377 |
| Resistin | 6135.91 | 618.15 | 6396.30 | 856.48 | 0.685 | 0.727 | −0.2127 | −0.5627 to 0.2021 | 0.2969 | 0.0013 | 0.194 | −0.0013 | 0.2382 | 1.00 | 0.21 to 4.68 | 1.0000 |
| VCAM | 17983.25 | 3556.02 | 8977.59 | 844.15 | 0.027 | 0.053 | 0.3709 | −0.0314 to 0.6698 | 0.0621 | 0.1776 | 0.406 | −0.1776 | 0.2307 | 12.40 | 1.83 to 83.8 | 0.0154 |
| BLyS | 1394.01 | 424.73 | 1593.04 | 423.06 | 0.191 | 0.292 | 0.1774 | −0.2369 to 0.5372 | 0.3958 | −0.0176 | 0.177 | 0.0176 | 0.1837 | 0.71 | 0.14 to 3.61 | 1.0000 |
| APRIL | 5423.03 | 1224.79 | 9245.06 | 1812.55 | 0.265 | 0.355 | 0.1417 | −0.2713 to 0.5106 | 0.4900 | 0.0038 | 0.122 | −0.0038 | 0.1644 | 1.00 | 0.12 to 8.43 | 1.0000 |
| IL-1RA/IL-1β | 7.42 | 1.88 | 20.38 | 3.98 | 0.001 | N.D. | −0.3493 | −0.6559 to 0.5931 | 0.0803 | 0.1559 | 0.322 | −0.1559 | 0.3130 | 3.89 | 0.72 to 21.1 | 0.2262 |

[a]Wilcoxon Matched-Pairs test (2-tailed); significant values ($p \leq 0.05$) highlighted in yellow
[b]Benjamini-Hochberg multiple testing procedure (False Discovery Rate < 0.05) using R version 2.15.3; significant values ($q < 0.05$) highlighted in yellow
[c]Spearman Rank Correlation; significant values ($p < 0.05$) highlighted in blue
[d]Odds Ratio (# of Flare vs. NF SLE patients with positive or negative soluble analyte score component value)
[e]Fisher's Exact test (2-tailed); significant values ($p < 0.05$) highlighted in green
N.D. = Not Determined

TABLE 5

Association Between Soluble Mediator Score and SLE Disease Activity in a Confirmatory Group of SLE Patients

| | | Soluble Mediator Score | | | | | | |
|---|---|---|---|---|---|---|---|---|
| | | Mean | Median | SD | p value[a] | OR[b] | 95% CI | P value[c] |
| A. | Flare subjects (n = 13) | 8.54 | 7.41 | 4.73 | <0.0001 | 729 | 13.4 to 13518 | <0.0001 |
| | NF subjects (n = 13) | −8.52 | −8.46 | 2.36 | | | | |
| B. | Flare subjects (n = 18) | 4.01 | 4.09 | 2.61 | <0.0001 | 164 | 7.8 to 3425 | <0.0001 |
| | SNF subjects (n = 18) | −4.06 | −4.01 | 2.81 | | | | |

A - SLE patients with flare vs. non-flare [NF] post-vaccination)
B - SLE patients with flare vs. a self non-flare (SNF) period
[a]Wilcoxon Matched-Pairs test (2-tailed)
[b]Odds Ratio (# of Flare vs. NF [or SNF] subjects with positive or negative soluble analyte score)
[c]Fisher's Exact test (2-tailed)

TABLE 6

Soluble Mediators in Confirmatory Group of Flare v. Non-Flare SLE Patients

| | Pre-flare Concentration (pg/ml) | | | | | Pre-flare Mediators vs. SELENA-SLEDAI score (at Flare) | | | | Soluble Mediator Score Component | | | | | |
|---|---|---|---|---|---|---|---|---|---|---|---|---|---|---|---|
| Analyte | Flare mean | SEM | SNF mean | SEM | p value[a] | q value[b] | Spearman r | 95% CI | P value[c] | Flare mean | SD | SNF mean | SD | OR[d] | 95% CI | P value[e] |
| Fas | 3.57 | 29.44 | 0.001 | 0.03 | 0.1250 | 0.1026 | 0.1728 | −0.2413 to 0.5337 | 0.3985 | 0.0734 | 0.225 | −0.0714 | 0.0000 | 12.80 | 0.61 to 2.67 | 0.0957 |
| IL-1β | 0.40 | 0.27 | 0.19 | 0.34 | 0.4375 | 0.3320 | −0.1244 | −0.4374 to 0.2874 | 0.5948 | 0.0000 | 0.131 | 0.0000 | 0.1227 | 1.00 | 0.19 to 5.29 | 1.0000 |
| IL-2 | 48.43 | 17.53 | 3.27 | 3.23 | 0.0002 | 0.0004 | 0.3512 | −0.0539 to 0.6570 | 0.0785 | 0.3067 | 0.075 | −0.2944 | 0.2358 | 1.24 | 5.38 to 28.52 | <0.0001 |
| IL-4 | 0.33 | 0.33 | 0.05 | 0.05 | 1.0000 | 0.5784 | −0.2576 | −0.3943 to 0.1559 | 0.2039 | −0.0094 | 0.294 | 0.0094 | 0.2266 | 1.00 | 0.05 to 17.9 | 1.0000 |
| IL-5 | 85.82 | 36.13 | 2.69 | 0.97 | 0.0002 | 0.0004 | 0.2850 | −0.3259 to 0.6131 | 0.1581 | 0.1913 | 0.039 | −0.1913 | 0.2862 | 31.20 | 1.53 to 53.4 | 0.0052 |
| IL-6 | 11.52 | 3.34 | 0.91 | 0.33 | 0.0002 | 0.0004 | 0.4108 | 0.0159 to 0.5549 | 0.0371 | 0.2703 | 0.125 | −0.2703 | 0.4216 | 41.70 | 2.04 to 85.5 | 0.0016 |
| IL-7 | 633.60 | 185.20 | 141.60 | 46.15 | 0.0005 | 0.0008 | 0.3631 | −0.0580 to 0.6550 | 0.557 | 0.2177 | 0.050 | −0.2127 | 0.4210 | 23.40 | 1.15 to 4.76 | 0.0149 |
| IL-8 | 1.12 | 0.63 | 0.05 | 0.05 | 0.0273 | 0.0239 | 0.5533 | 0.1995 to 0.7794 | 0.0034 | 0.3332 | 0.555 | −0.3332 | 0.2985 | 27.00 | 2.36 to 28.5 | 0.0035 |
| IL-10 | 1.95 | 0.43 | 11.42 | 3.12 | 0.0034 | 0.0045 | −0.2268 | −0.3727 to 0.1877 | 0.2602 | 0.0444 | 0.203 | −0.0444 | 0.2486 | 1.48 | 0.26 to 8.50 | 1.0000 |
| TGF-β | 2.85 | 1.32 | 24.80 | 6.03 | 0.0002 | 0.0004 | −0.5936 | −0.8019 to −0.2355 | 0.0014 | 0.4218 | 0.576 | −0.4218 | 0.1285 | 41.70 | 2.04 to 85.5 | 0.0016 |
| IFN-β | 199.80 | 68.81 | 20.63 | 6.11 | 0.0053 | 0.0080 | 0.4262 | 0.0345 to 0.7044 | 0.0299 | 0.3251 | 0.153 | −0.3251 | 0.3551 | 57.00 | 2.73 to 11.89 | 0.0005 |
| IL-12(p70) | 23.20 | 6.16 | 1.21 | 0.54 | 0.0005 | 0.0008 | 0.5083 | 0.1388 to 0.7536 | 0.0080 | 0.3889 | 0.132 | −0.3889 | 0.4395 | 57.00 | 2.73 to 11.89 | 0.0005 |
| IL-13 | 51.99 | 20.29 | 0.85 | 0.85 | 0.0039 | 0.0048 | 0.3765 | −0.02479 to 0.6793 | 0.0580 | 0.2369 | 0.373 | −0.2369 | 0.1851 | 27.00 | 2.56 to 23.5 | 0.0036 |
| IL-23(p19) | 82.63 | 33.21 | 14.20 | 7.30 | 0.0137 | 0.0195 | 0.3832 | −0.0170 to 0.5776 | 0.0533 | 0.1538 | 0.323 | −0.1538 | 0.3375 | 4.71 | 0.734 to 30.3 | 0.2016 |
| INF-γ | 2.97 | 1.49 | 0.003 | 0.001 | 0.0625 | 0.0577 | 0.3051 | −0.1050 to 0.6257 | 0.1295 | 0.1423 | 0.377 | −0.1423 | 0.0897 | 17.50 | 0.85 to 35.8 | 0.0391 |
| TNF-α | 1.46 | 1.33 | 1.10 | 0.65 | 0.4922 | 0.3465 | −0.1155 | −0.4828 to 0.3049 | 0.6081 | 0.0218 | 0.102 | −0.0218 | 0.1035 | 2.63 | 0.53 to 13.10 | 0.4283 |
| G-CSF | 13.74 | 8.16 | 0.18 | 0.43 | 0.1250 | 0.1026 | 0.2514 | −0.1624 to 0.5900 | 0.2154 | 0.0818 | 0.315 | −0.0818 | 0.1346 | 0.39 | 0.08 to 1.84 | 0.2761 |
| INF-α | 133.70 | 29.63 | 9.05 | 3.35 | 0.0005 | 0.0008 | 0.3781 | −0.0229 to 0.6743 | 0.0568 | 0.2258 | 0.127 | −0.2258 | 0.4144 | 40.00 | 3.58 to 44.7 | 0.0010 |
| IL-1α | 35.02 | 3.81 | 2.80 | 1.97 | 0.0050 | 0.0015 | 0.4838 | 0.1093 to 0.7403 | 0.0119 | 0.3234 | 0.371 | −0.3234 | 0.3564 | 18.30 | 2.52 to 13.3 | 0.0048 |
| IL-1RA | 243.50 | 107.70 | 200.50 | 43.85 | 0.6221 | 0.4058 | −0.2121 | −0.3623 to 0.2025 | 0.2582 | 0.0745 | 0.283 | −0.0745 | 0.0895 | 12.80 | 0.61 to 25.7 | 0.0957 |
| IL-15 | 14.34 | 9.60 | 0.001 | 0.00 | 0.1250 | 0.1026 | 0.2790 | −0.1334 to 0.6090 | 0.1675 | 0.1162 | 0.365 | −0.1162 | 0.0000 | 12.80 | 0.61 to 25.7 | 0.0957 |
| IL-21 | 25.00 | 12.71 | 0.001 | 0.00 | 0.0625 | 0.0577 | 0.5164 | 0.1495 to 0.7583 | 0.0059 | 0.2453 | 0.652 | −0.2453 | 0.0000 | 17.50 | 0.85 to 35.8 | 0.0391 |
| ICAM-1 | 450.33 | 63.70 | 370.51 | 103.14 | 0.0338 | 0.0394 | 0.3603 | 0.2097 to 0.7835 | 0.0029 | 0.1674 | 0.457 | −0.1674 | 0.6206 | 5.33 | 0.97 to 29.4 | 0.1107 |
| IL-17A | 8.90 | 2.25 | 0.14 | 0.34 | 0.0002 | 0.0004 | 0.3810 | 0.2385 to 0.7950 | 0.0019 | 0.5325 | 0.124 | −0.5325 | 0.2711 | 22.5 | 8.35 to 60.33 | <0.0001 |
| NGF-β | 21.18 | 8.48 | 1.05 | 0.54 | 0.0039 | 0.0048 | 0.2302 | −0.1842 to 0.5751 | 0.2579 | 0.1100 | 0.216 | −0.1100 | 0.1937 | 5.33 | 0.97 to 29.4 | 0.1107 |
| Leptin | 1419.46 | 175.48 | 483.74 | 74.46 | 0.0002 | 0.0004 | 0.2652 | −0.1480 to 0.5995 | 0.1504 | 0.1704 | 0.192 | −0.1704 | 0.2138 | 18.30 | 2.52 to 13.3 | 0.0048 |
| SCF | 363.50 | 163.80 | 81.48 | 10.65 | 0.0002 | 0.0004 | 0.4138 | 0.0218 to 0.6980 | 0.0346 | 0.2488 | 0.403 | −0.2488 | 0.2435 | 12.40 | 1.83 to 83.8 | 0.0154 |
| IL-2Rα | 282.50 | 38.83 | 118.40 | 10.78 | 0.0002 | 0.0004 | 0.4143 | 0.0120 to 0.6970 | 0.0354 | 0.2873 | 0.343 | −0.2873 | 0.2468 | 65.00 | 5.22 to 83.4 | 0.0002 |
| SDF-1 | 1955.00 | 105.20 | 2245.00 | 170.50 | 0.1272 | 0.1025 | 0.1733 | −0.2403 to 0.5341 | 0.3571 | −0.0508 | 0.150 | 0.0508 | 0.1835 | 0.38 | 0.08 to 1.90 | 0.4283 |
| MIG | 1265.00 | 400.80 | 203.90 | 29.94 | 0.0002 | 0.0004 | 0.4680 | 0.0385 to 0.7293 | 0.0159 | 0.3024 | 0.455 | −0.3024 | 0.2233 | 6.42 | 0.99 to 41.2 | 0.0368 |
| MIP-1α | 491.10 | 201.30 | 122.20 | 35.01 | 0.0005 | 0.0008 | 0.0471 | −0.3071 to 0.4365 | 0.8191 | 0.0225 | 0.043 | −0.0225 | 0.0405 | 5.33 | 0.97 to 29.4 | 0.1107 |

TABLE 6-continued

Soluble Mediators in Confirmatory Group of Flare v. Non-Flare SLE Patients

| | Pre-flare Concentration (pg/ml) | | | | | | Pre-flare Mediators vs. SELENA-SLEDAI score (at Flare) | | | Soluble Mediator Score Component | | | | | |
|---|---|---|---|---|---|---|---|---|---|---|---|---|---|---|---|
| Analyte | Flare mean | SEM | SNF mean | SEM | p value[a] | q value[b] | Spearman r | 95% CI | P value[c] | Flare mean | SD | SNF mean | SD | OR[d] | 95% CI | P value[e] |
| MCP-3 | 1552.00 | 203.60 | 812.60 | 105.80 | 0.0002 | 0.0004 | 0.5737 | 0.2282 to 0.7509 | 0.0022 | 0.3731 | 0.355 | −0.3731 | 0.5080 | 18.30 | 2.52 to 13.3 | 0.0048 |
| PAI-1 | 2954.00 | 200.30 | 2883.00 | 324.80 | 0.3879 | 0.3318 | 0.2343 | −0.1300 to 0.5781 | 0.2492 | 0.0254 | 0.176 | −0.0254 | 0.2854 | 0.74 | 0.16 to 3.44 | 1.0000 |
| FasL | 70.53 | 4.63 | 32.61 | 4.00 | 0.0002 | 0.0004 | 0.3158 | −0.0935 to 0.6338 | 0.1150 | 0.2390 | 0.150 | −0.2390 | 0.2480 | 30.30 | 3.59 to 25.5 | 0.0012 |
| IP-10 | 2390.00 | 463.30 | 731.20 | 148.70 | 0.0002 | 0.0004 | 0.4254 | 0.0347 to 0.7045 | 0.0293 | 0.2427 | 0.404 | −0.2427 | 0.2970 | 11.10 | 1.79 to 63.9 | 0.0169 |
| PDGF-88 | 73.49 | 15.26 | 65.18 | 13.70 | 0.8925 | 0.3585 | −0.0988 | −0.4776 to 0.3110 | 0.6311 | −0.0102 | 0.087 | 0.0102 | 0.1123 | 1.00 | 0.21 to 4.53 | 1.0000 |
| RANTES | 2445.00 | 605.00 | 1743.00 | 180.10 | 0.4548 | 0.3320 | 0.0125 | −0.3870 to 0.4080 | 0.9713 | 0.0021 | 0.013 | −0.0021 | 0.0115 | 1.00 | 0.21 to 4.53 | 1.0000 |
| MIP1-β | 342.20 | 82.17 | 295.10 | 49.56 | 0.0002 | 0.0004 | 0.4076 | 0.0119 to 0.6929 | 0.0388 | 0.2204 | 0.323 | −0.2204 | 0.3691 | 5.33 | 0.97 to 29.4 | 0.1107 |
| LIF | 4.74 | 1.20 | 3.27 | 0.59 | 0.4548 | 0.3320 | 0.0157 | −0.3335 to 0.4115 | 0.9357 | 0.0035 | 0.016 | −0.0035 | 0.0173 | 1.36 | 0.29 to 6.35 | 1.0000 |
| MCP-1 | 314.80 | 70.73 | 92.19 | 18.76 | 0.0002 | 0.0004 | 0.4524 | 0.0563 to 0.7204 | 0.0203 | 0.2575 | 0.335 | −0.2575 | 0.3986 | 7.50 | 1.31 to 43.0 | 0.0472 |
| Eotaxin | 319.90 | 101.10 | 335.50 | 79.73 | 0.4973 | 0.3465 | 0.0524 | −0.3437 to 0.4488 | 0.7620 | −0.0032 | 0.063 | 0.0032 | 0.0543 | 1.00 | 0.21 to 4.53 | 1.0000 |
| VEGF | 175.50 | 22.45 | 153.40 | 20.68 | 0.3879 | 0.3918 | 0.0539 | −0.3512 to 0.4420 | 0.7935 | −0.0102 | 0.043 | 0.0102 | 0.0531 | 1.00 | 0.21 to 4.85 | 1.0000 |
| TNFRI | 3799.00 | 633.40 | 1387.00 | 134.50 | 0.0012 | 0.0017 | 0.2947 | −0.1166 to 0.6196 | 0.1440 | 0.1896 | 0.269 | −0.1896 | 0.1738 | 27.00 | 2.56 to 28.3 | 0.0035 |
| TRAIL | 408.50 | 122.00 | 211.00 | 47.65 | 0.0005 | 0.0008 | 0.3020 | 0.1304 to 0.7499 | 0.0090 | 0.2133 | 0.579 | −0.2133 | 0.3022 | 12.40 | 1.83 to 83.8 | 0.0154 |
| TNFRII | 1392.00 | 105.90 | 993.60 | 89.45 | 0.0398 | 0.0394 | 0.1889 | 0.1304 to 0.7499 | 0.3553 | 0.0927 | 0.144 | −0.0927 | 0.1874 | 7.50 | 1.31 to 43.0 | 0.0472 |
| GRD-α | 31.75 | 11.10 | 47.10 | 9.17 | 1.0000 | 0.5784 | 0.0142 | −0.3355 to 0.4095 | 0.9451 | 0.0000 | 0.016 | 0.0000 | 0.0130 | 2.36 | 0.49 to 11.5 | 0.4328 |
| E-selectin | 3129.00 | 320.40 | 2933.00 | 371.30 | 0.7869 | 0.5026 | 0.0915 | −0.3176 to 0.4719 | 0.6565 | 0.0114 | 0.071 | −0.0114 | 0.1102 | 1.36 | 0.29 to 6.36 | 1.0000 |
| CD40L | 1790.00 | 226.80 | 360.00 | 76.78 | 0.0005 | 0.0008 | 0.6164 | 0.2893 to 0.8144 | 0.0008 | 0.4503 | 0.305 | −0.4503 | 0.4893 | 144.00 | 8.04 to 25.80 | <0.0001 |
| Resistin | 2203.00 | 339.00 | 1250.00 | 287.30 | 0.0171 | 0.0187 | 0.2818 | −0.1303 to 0.6109 | 0.1531 | 0.1254 | 0.237 | −0.1254 | 0.2731 | 3.60 | 0.71 to 53.3 | 0.2377 |
| VCAM | 143.63 | 28.15 | 109.29 | 13.56 | 0.9460 | 0.5784 | 0.0059 | −0.3925 to 0.4025 | 0.9772 | 0.0015 | 0.004 | −0.0015 | 0.0070 | 1.35 | 0.29 to 6.35 | 1.0000 |
| BLyS | 1015.00 | 187.50 | 905.50 | 232.50 | 1.0000 | 0.5784 | −0.0895 | −0.4303 to 0.3638 | 0.8480 | −0.0097 | 0.040 | 0.0097 | 0.0381 | 0.38 | 0.03 to 1.90 | 0.4283 |
| APRIL | 2493.00 | 982.70 | 3935.00 | 1345.00 | 0.3750 | 0.2948 | −0.1154 | −0.4913 to 0.2948 | 0.5711 | 0.0238 | 0.121 | −0.0238 | 0.1105 | 2.63 | 0.53 to 13.10 | 0.4283 |
| IL-1RA/IL-1β | 715.12 | 411.57 | 1353.95 | 480.89 | 0.0540 | 0.577 | −0.2955 | −0.5935 to 0.1570 | 0.2098 | 0.0855 | 0.302 | −0.0855 | 0.1721 | 2.86 | 0.53 to 15.5 | 0.4110 |

[a]Wilcoxon Matched-Pairs test (2-tailed); significant values (p ≤ 0.05) highlighted in yellow
[b]Benjamini-Hochberg multiple testing procedure (False Discovery Rate < 0.05) using R version 2.15.3; significant values (q < 0.05) highlighted in yellow
[c]Spearman Rank Correlation; significant values (p < 0.05) highlighted in blue
[d]Odds Ratio (# of Flare vs. NF SLE patients with positive or negative soluble analyte score component value)
[e]Fisher's Exact test (2-tailed); significant values (p < 0.05) highlighted in green

TABLE 7

Soluble Mediators in Confirmatory Group of Flare v. SNF SLE Samples

| Analyte | Pre-flare Concentration (pg/ml) | | | | | Pre-flare Mediators vs. SELENA-SLEDAI score (at Flare) | | | | Soluble Mediator Score Component | | | | | | |
|---|---|---|---|---|---|---|---|---|---|---|---|---|---|---|---|---|
| | Flare mean | SEM | SNF mean | SEM | p value[a] | q value[b] | Spearman r | 95% CI | P value[c] | Flare mean | SD | SNF mean | SD | OR[d] | 95% CI | P value[e] |
| Fas | 38.04 | 20.02 | 3.53 | 3.53 | 0.1250 | 0.0389 | −0.0232 | −0.3579 to 0.3168 | 0.8930 | −0.0057 | 0.029 | 0.0057 | 0.015 | 0.21 | 0.21 to 2.06 | 0.3377 |
| IL-1β | 0.53 | 0.38 | 0.33 | 0.15 | 0.5405 | 0.3585 | −0.2204 | −0.5193 to 0.1263 | 0.1954 | 0.0292 | 0.223 | −0.0292 | 0.223 | 1.65 | 0.41 to 6.72 | 0.7247 |
| IL-2 | 95.00 | 32.97 | 31.81 | 17.93 | <0.0001 | <0.0001 | 0.2513 | −0.0942 to 0.5428 | 0.1393 | 0.1007 | 0.200 | −0.1007 | 0.262 | 8.00 | 1.41 to 45.4 | 0.0275 |
| IL-4 | 0.39 | 0.21 | 0.33 | 0.23 | 1.0000 | 0.5102 | 0.0592 | −0.2747 to 0.3974 | 0.5885 | 0.0051 | 0.073 | −0.0051 | 0.065 | 1.60 | 0.23 to 11.0 | 1.0000 |
| IL-5 | 101.60 | 25.94 | 29.51 | 11.95 | <0.0001 | <0.0001 | 0.3553 | 0.0657 to 0.6466 | 0.0170 | 0.1965 | 0.134 | −0.1965 | 0.471 | 16.70 | 2.88 to 2.48 | 0.0005 |
| IL-6 | 12.71 | 4.97 | 3.74 | 3.26 | 0.0038 | 0.0038 | 0.2123 | −0.1343 to 0.5131 | 0.2138 | 0.0639 | 0.193 | −0.0639 | 0.209 | 4.38 | 1.03 to 18.5 | 0.0858 |
| IL-7 | 924.10 | 163.00 | 380.20 | 103.20 | <0.0001 | <0.0001 | 0.2019 | −0.1455 to 0.5050 | 0.2378 | 0.0896 | 0.036 | −0.0896 | 0.256 | 24.20 | 1.25 to 4.64 | 0.0075 |
| IL-8 | 2.05 | 0.93 | 0.53 | 0.24 | 0.0151 | 0.0145 | 0.0357 | −0.2593 to 0.4113 | 0.6194 | 0.0317 | 0.078 | −0.0317 | 0.083 | 3.50 | 1.28 to 23.7 | 0.0005 |
| IL-10 | 2.63 | 0.73 | 11.28 | 2.45 | <0.0001 | <0.0001 | −0.2720 | −0.5582 to 0.0721 | 0.1085 | 0.1348 | 0.321 | −0.1348 | 0.103 | 17.00 | 1.85 to 13.5 | 0.0072 |
| TGF-β | 7.78 | 3.48 | 35.70 | 9.75 | <0.0001 | <0.0001 | −0.4154 | −0.6503 to 0.0905 | 0.0118 | 0.2638 | 0.438 | −0.2638 | 0.126 | 26.70 | 2.88 to 24.8 | 0.0005 |
| IFN-β | 140.10 | 49.50 | 14.04 | 5.90 | <0.0001 | <0.0001 | 0.4711 | 0.1589 to 0.6977 | 0.0037 | 0.2622 | 0.334 | −0.2622 | 0.447 | 12.60 | 2.19 to 72.3 | 0.0005 |
| IL-12(p70) | 56.43 | 24.13 | 11.26 | 10.22 | <0.0001 | <0.0001 | 0.1813 | −0.1974 to 0.4881 | 0.2927 | 0.0716 | 0.138 | −0.0716 | 0.193 | 8.00 | 1.41 to 43.4 | 0.0275 |
| IL-13 | 44.25 | 15.53 | 9.64 | 4.55 | 0.0017 | 0.0012 | 0.2271 | −0.1351 to 0.5129 | 0.2143 | 0.0543 | 0.218 | −0.0543 | 0.191 | 3.14 | 0.80 to 12.3 | 0.1811 |
| IL-23(p19) | 95.03 | 45.60 | 27.78 | 11.63 | 0.0230 | 0.0183 | 0.1450 | −0.2014 to 0.4603 | 0.3955 | 0.0404 | 0.142 | −0.0404 | 0.142 | 3.14 | 0.80 to 12.3 | 0.1811 |
| INF-γ | 28.84 | 18.38 | 8.42 | 7.35 | 0.0525 | 0.0432 | 0.0058 | −0.3323 to 0.3426 | 0.9732 | 0.0009 | 0.006 | −0.0009 | 0.005 | 1.52 | 0.38 to 9.63 | 0.6905 |
| TNF-α | 1.57 | 0.87 | 0.55 | 0.28 | 0.2387 | 0.1783 | −0.1305 | −0.4433 to 0.2165 | 0.4479 | −0.0035 | 0.138 | 0.0035 | 0.127 | 1.00 | 0.26 to 3.82 | 1.0000 |
| G-CSF | 8.77 | 6.00 | 0.74 | 0.43 | 0.3125 | 0.2059 | 0.3111 | −0.0295 to 0.5870 | 0.0548 | 0.0195 | 0.351 | −0.0195 | 0.274 | 1.00 | 0.17 to 5.77 | 1.0000 |
| INF-α | 110.30 | 22.60 | 30.50 | 12.41 | <0.0001 | <0.0001 | 0.4415 | 0.1272 to 0.6780 | 0.0070 | 0.2194 | 0.147 | −0.2194 | 0.330 | 10.80 | 0.16 to 10.0 | 0.0408 |
| IL-1α | 49.03 | 11.83 | 16.24 | 6.72 | 0.0002 | 0.0002 | 0.3898 | 0.0602 to 0.6427 | 0.0188 | 0.1452 | 0.345 | −0.1452 | 0.384 | 4.33 | 1.03 to 18.5 | 0.0858 |
| IL-1RA | 342.70 | 130.80 | 359.10 | 95.94 | 0.0385 | 0.0315 | −0.1931 | −0.4982 to 0.1544 | 0.2591 | 0.0700 | 0.254 | −0.0700 | 0.044 | 10.80 | 1.16 to 10.0 | 0.408 |
| IL-15 | 11.06 | 5.45 | 21.02 | 10.67 | 0.5875 | 0.3873 | 0.0154 | −0.3238 to 0.3510 | 0.9291 | −0.0005 | 0.015 | 0.0005 | 0.016 | 1.30 | .31 to 5.39 | 1.0000 |
| IL-21 | 51.52 | 24.93 | 4.55 | 3.89 | 0.0159 | 0.0145 | 0.1397 | −0.2076 to 0.4337 | 0.4155 | 0.0465 | 0.154 | −0.0465 | 0.094 | 5.09 | 0.89 to 29.3 | 0.1212 |
| ICAM-1 | 480.53 | 47.70 | 261.74 | 32.88 | <0.0001 | <0.0001 | 0.3312 | −0.0071 to 0.6015 | 0.0485 | 0.1712 | 0.193 | −0.1712 | 0.356 | 34.00 | 3.61 to 32.0 | 0.0005 |
| IL-17A | 7.88 | 2.02 | 2.09 | 0.93 | 0.0013 | 0.0015 | 0.2899 | −0.0528 to 0.5715 | 0.0853 | 0.1524 | 0.171 | −0.1524 | 0.308 | 17.00 | 1.85 to 1.56 | 0.0072 |
| NGF-β | 33.30 | 12.64 | 17.65 | 10.15 | 0.0009 | 0.0012 | 0.2203 | −0.1267 to 0.5192 | 0.1957 | 0.0735 | 0.188 | −0.0735 | 0.230 | 4.00 | .85 to 18.8 | 0.1054 |
| Leptin | 12265.5 | 200.12 | 783.93 | 114.04 | 0.0013 | 0.0020 | 0.2752 | −0.0537 to 0.3505 | 0.1043 | 0.0801 | 0.243 | −0.0801 | 0.285 | 2.00 | .52 to 7.69 | 0.4938 |
| SCF | 385.80 | 121.60 | 144.00 | 13.89 | <0.0001 | <0.0001 | 0.2851 | −0.0580 to 0.5879 | 0.0919 | 0.1449 | 0.318 | −0.1449 | 0.148 | 13.00 | 2.59 to 65.2 | 0.0020 |
| IL-2Rα | 327.30 | 38.04 | 155.20 | 24.72 | <0.0001 | <0.0001 | 0.2112 | −0.1360 to 0.5122 | 0.2152 | 0.1088 | 0.180 | −0.1088 | 0.186 | 12.30 | 2.54 to .59 | 0.0072 |
| SDF-1 | 2956.00 | 853.30 | 2577.00 | 337.40 | 0.1084 | 0.0732 | −0.0304 | −0.3642 to 0.3103 | 0.8502 | 0.0004 | 0.035 | −0.0004 | 0.026 | 1.00 | 0.21 to 4.82 | 1.0000 |
| MIG | 1285.00 | 450.90 | 503.00 | 152.50 | 0.0033 | 0.0012 | 0.2341 | −0.0913 to 0.5448 | 0.1349 | 0.0859 | 0.252 | −0.0859 | 0.221 | 4.03 | 1.01 to 16.6 | 0.0372 |

TABLE 7-continued

Soluble Mediators in Confirmatory Group of Flare v. SNF SLE Samples

| | Pre-flare Concentration (pg/ml) | | | | | | Pre-flare Mediators vs. SELENA-SLEDAI score (at Flare) | | | Soluble Mediator Score Component | | | | | |
|---|---|---|---|---|---|---|---|---|---|---|---|---|---|---|---|
| Analyte | Flare mean | SEM | SNF mean | SEM | p value[a] | q value[b] | Spearman r | 95% CI | P value[c] | Flare mean | SD | SNF mean | SD | OR[d] | 95% CI | P value[e] |
| MIP-1α | 335.30 | 131.90 | 82.32 | 15.39 | 0.0013 | 0.0020 | 0.1583 | −0.1492 to 0.5022 | 0.2483 | 0.0789 | 0.190 | −0.0789 | 0.178 | 3.14 | 0.80 to 12.3 | 0.1811 |
| MCP-3 | 1765.00 | 170.10 | 1029.00 | 83.16 | <0.0001 | <0.0001 | 0.3424 | 0.0055 to 0.6095 | 0.0409 | 0.2029 | 0.255 | −0.2029 | 0.289 | 5.20 | 1.25 to 21.6 | 0.0437 |
| PAI-1 | 3214.00 | 491.20 | 3015.00 | 340.50 | 1.0000 | 0.5102 | 0.2450 | −0.2015 to 0.4803 | 0.3957 | 0.0145 | 0.113 | −0.0145 | 0.175 | 0.64 | 0.17 to 2.39 | 0.7380 |
| FasL | 77.44 | 5.80 | 33.95 | 4.51 | <0.0001 | <0.0001 | 0.3584 | 0.0544 to 0.6432 | 0.0176 | 0.2828 | 0.229 | −0.2828 | 0.311 | 28.00 | 4.43 to 1.77 | 0.0001 |
| IP-10 | 4051.00 | 1514.00 | 1671.00 | 755.30 | <0.0001 | <0.0001 | 0.3004 | −0.0413 to 0.5792 | 0.0750 | 0.1426 | 0.250 | −0.1426 | 0.274 | 5.20 | 1.25 to 21.6 | 0.0437 |
| PDGF-88 | 5979.00 | 1132.00 | 5319.00 | 869.50 | 0.9551 | 0.5102 | 0.0299 | −0.3107 to 0.3637 | 0.8526 | 0.0027 | 0.030 | −0.0027 | 0.031 | 1.00 | 0.27 to 3.73 | 1.0000 |
| RANTES | 2625.00 | 394.20 | 1873.00 | 103.70 | 0.0237 | 0.0200 | 0.1097 | −0.2365 to 0.4312 | 0.5243 | 0.0369 | 0.131 | −0.0369 | 0.068 | 4.00 | 1.00 to 1.6 | 0.0943 |
| MIP1-β | 715.80 | 85.01 | 459.00 | 65.19 | <0.0001 | <0.0001 | 0.2287 | −0.1179 to 0.5237 | 0.1735 | 0.0913 | 0.190 | −0.0913 | 0.232 | 4.00 | 1.00 to 1.6 | 0.0943 |
| LIF | 4.79 | 0.83 | 4.27 | 0.60 | 0.7650 | 0.4227 | −0.1107 | −0.4321 to 0.2355 | 0.5203 | −0.0042 | 0.114 | 0.0042 | 0.110 | 0.80 | 0.22 to 2.97 | 13.000 |
| MCP-1 | 340.30 | 125.20 | 157.40 | 44.53 | 0.0004 | 0.0005 | 0.3024 | −0.0391 to 0.5805 | 0.0731 | 0.1010 | 0.326 | −0.1010 | 0.245 | 2.60 | 0.65 to 10.4 | 0.3053 |
| Eotaxin | 335.80 | 70.36 | 334.10 | 65.55 | 0.5055 | 0.3983 | 0.0751 | −0.2632 to 0.4034 | 0.6585 | 0.0050 | 0.053 | −0.0050 | 0.089 | 1.25 | 0.34 to 4.64 | 1.0000 |
| VEGF | 184.90 | 27.12 | 178.10 | 18.67 | 0.9537 | 0.5102 | −0.1453 | −0.4604 to 0.2020 | 0.3973 | −0.0023 | 0.141 | 0.0023 | 0.134 | 1.95 | .52 to 7.41 | 0.5051 |
| TNFRI | 3877.00 | 659.70 | 2439.00 | 405.60 | 0.0001 | 0.0002 | 0.1045 | −0.2415 to 0.4270 | 0.5439 | 0.0354 | 0.102 | −0.0354 | 0.093 | 3.14 | 0.80 to 12.3 | 0.1811 |
| TRAIL | 2351.00 | 1107.00 | 414.40 | 149.30 | <0.0001 | <0.0001 | 0.1047 | −0.2418 to 0.4267 | 0.5454 | 0.0345 | 0.123 | −0.0345 | 0.068 | 3.18 | 0.67 to 15.2 | 0.2842 |
| TNFRII | 1307.000 | 133.00 | 1242.00 | 93.92 | 0.0182 | 0.0154 | 0.0409 | −0.3003 to 0.3732 | 0.8129 | 0.0099 | 0.041 | −0.0099 | 0.041 | 1.25 | 0.34 to 4.64 | 1.0000 |
| GRD-α | 52.65 | 9.29 | 57.04 | 8.70 | 0.5225 | 0.3211 | −0.1459 | −0.4615 to 0.2005 | 0.3927 | 0.0155 | 0.150 | −0.0155 | 0.135 | 1.25 | 0.34 to 4.64 | 1.0000 |
| E-selectin | 4417.00 | 330.80 | 4111.00 | 424.30 | 0.5738 | 0.3484 | −0.0558 | −0.3945 to 0.2779 | 0.7030 | −0.0035 | 0.057 | 0.0035 | 0.066 | 1.25 | 0.34 to 4.64 | 1.0000 |
| CD40L | 1445.00 | 194.40 | 655.80 | 95.15 | 0.0003 | 0.0004 | 0.3287 | −0.0099 to 0.5997 | 0.0503 | 0.2036 | 0.239 | −0.2036 | 0.279 | 9.10 | 2.00 to 41.5 | 0.0057 |
| Resistin | 1830.00 | 323.00 | 2036.00 | 388.00 | 0.3158 | 0.2053 | 0.0210 | −0.3187 to 0.3560 | 0.9032 | −0.0002 | 0.020 | 0.0002 | 0.023 | 0.64 | 0.17 to 2.38 | 0.7395 |
| VCAM | 14842.00 | 2219.00 | 13839.00 | 407.50 | 0.0649 | 0.0432 | −0.1007 | −0.4238 to 0.2432 | 0.3591 | 0.0041 | 0.139 | −0.0041 | 0.040 | 1.57 | 0.42 to 5.91 | 0.7383 |
| BLyS | 1023.00 | 226.40 | 1142.00 | 209.70 | 0.1674 | 0.1151 | −0.3001 | −0.5790 to 0.0416 | 0.0753 | 0.0403 | 0.322 | −0.0403 | 0.280 | 0.80 | 0.22 to 2.97 | 1.0000 |
| APRIL | 6595.00 | 3612.00 | 3986.00 | 1652.00 | 0.4887 | 0.3073 | −0.3020 | −0.3803 to 0.0395 | 0.0735 | 0.0189 | 0.307 | −0.0189 | 0.303 | 1.25 | 0.33 to 4.74 | 1.0000 |
| IL-1RA/IL-1β | 907.00 | 322.29 | 1476.59 | 438.25 | 0.0655 | 0.0432 | −0.1414 | −0.4571 to 0.2059 | 0.4107 | 0.0411 | 0.155 | −0.0411 | 0.100 | 1.25 | 0.33 to 4.74 | 1.0000 |

[a]Wilcoxon Matched-Pairs test (2-tailed); significant values (p < 0.05) highlighted in yellow
[b]Benjamini-Hochberg multiple testing procedure (False Discovery Rate ≤ 0.05) using R version 2.15.3; significant values (q ≤ 0.05) highlighted in yellow
[c]Spearman Rank Correlation; significant values (p < 0.05) highlighted in blue
[d]Odds Ratio (# of Flare vs. NF SLE patients with positive or negative soluble analyte score component value)
[e]Fisher's Exact test (2-tailed); significant values (p < 0.05) highlighted in green

Example 3—Discussion

Figure 5:
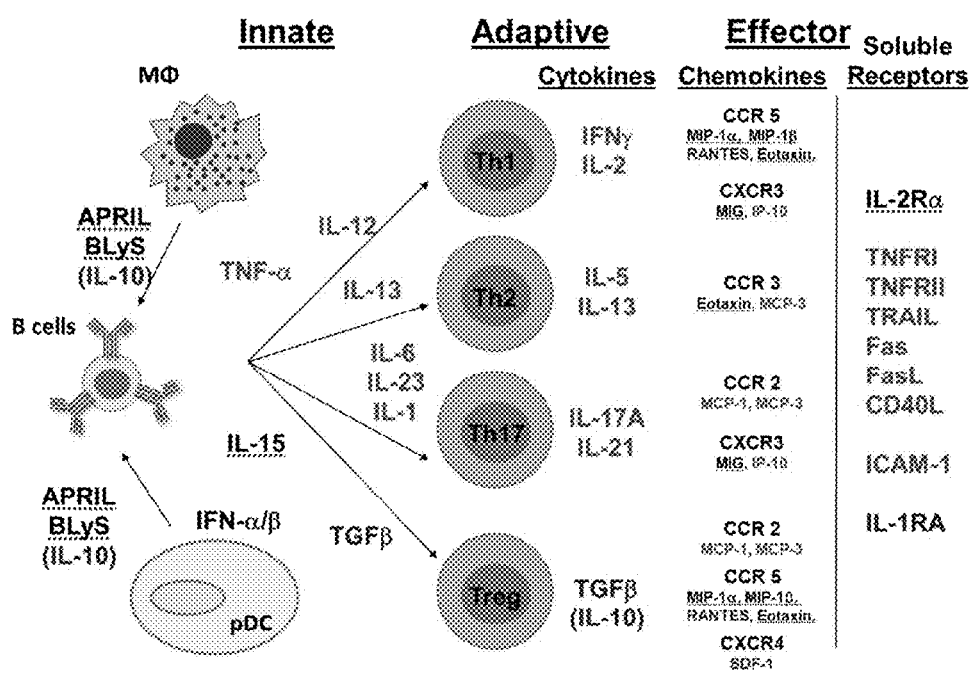
FIG. 5. Summary of altered soluble mediators in SLE patients prior to disease flare. Inflammatory mediators which were significantly higher in SLE patients with impending disease flare (compared to NF/SNF and HC) are listed in red, while those significantly higher in the NF/SNF groups (compared to pre-flare and HC) are listed in blue. Those mediators which were found to be higher in SLE patients compared to HC, but not different between groups of SLE patients, are underlined. SLE patients with impending disease flare have increased innate and adaptive mediators of inflammation, including those from Th1, Th2, and Th17 pathways. In addition inflammatory chemokines and soluble TNFR superfamily members are elevated. SLE patients who are in a period of non-flare (NF/SNF groups) have higher regulatory mediators, including IL-10, TGF-β, and IL-1RA FIGS. 6A-H. Altered adaptive immunity and soluble TNF superfamily members in SLE patients with impending and concurrent disease flare. Plasma Th1—(FIG. 6A, IL-12p70, IFN-γ, and IL-2), Th2—(FIG. 6B, IL-5, IL-13, and IL-6), and Th17—(FIG. 6C, IL-23p19, IL-17A, and IL-21) type cytokines, as well as chemokines (FIG. 6D, IP-10, MCP-1, and MCP-3), soluble TNF superfamily members (FIG. 6E, TNF-α, TNFRI, TNFRII, Fas, FasL, and CD40L), regulatory mediators (FIG. 6F, IL-10, TGF-β, SDF-1), IL-RA/IL-1β balance (FIG. 6G, IL-1β, IL-1RA, and ratio of IL-1RA:IL-13), and other inflammatory mediators (FIG. 6H, IL-1α, IL-8, ICAM-1, SCF, RANTES, and Resistin) (mean±SEM) were measured (mean±SEM) by xMAP® multiplex assay according to manufacturer protocol (Affymetrix, Santa Clara, Calif.) and read on a Bio-plex 200 reader (Bio-Rad, Hercules, Calif.). Samples were procured at baseline (BL)/pre-vaccination (circle) from 28 EA SLE patients who exhibited disease flare (black symbol) 6 to 12 weeks later (follow-up [FU], square) vs. age (±5 years)/race/gender/time of sample procurement matched SLE patients who did not flare (NF, blue symbol) vs. age (±5 years)/race/gender/time of sample procurement matched unrelated/unaffected healthy controls (HC, open symbol). Significance determined by Friedman test with Dunn's multiple comparison (Friedman test significance listed under each title). *p<0.05, p<0.01, *p<0.001, ****p, 0.0001.

Delays in treating SLE flares may potentiate chronic inflammation, leading to recurrent illness and end-organ damage. Immune dysregulation in SLE likely precedes clinical disease, and in some cases, low grade, smoldering inflammation could persist over time, contributing to progressive organ damage in the absence of overt clinical flare. The data point to the "yin-yang" nature of the immune response that either leads to impending disease flare (inflammation) or allows for periods of non-flare (regulation). In this study elevated levels of shed TNF receptors and/or pro-inflammatory Th adaptive pathway cytokines were found in nearly all SLE patients prior to impending flare (FIG. 5). While a predominant inflammatory pathway is evident for a subset of patients, most had elevated inflammatory mediators from multiple pathways, which may help explain variability among previous reports of inflammatory mediators in SLE patients with active disease (Gomez et al., 2004; Tokano et al., 1999; Mok et al., 2010.). In this study, regulatory factors were less likely to be elevated prior to a flare, suggesting an altered balance of inflammatory and regulatory mediators.

Significantly higher levels of IL-1β and IL-1α, as well as lower levels of IL-1RA, preceding a disease flare suggest that diminished downregulation of innate cytokines may contribute to increased disease activity during SLE flares. Additionally, T-regulatory cells require TGF-β and IL-10 for their development and propagation (reviewed in Okamoto et al., 2011). In this study, the lower levels of TGF-β and IL-10, with increased inflammatory cytokines, may reflect a failure of active regulation in the period before disease flare. IL-10 and TGF-β levels are higher in stable SLE patients, suggesting the possibility of context-dependent regulatory roles for these cytokines. Future studies will assess whether SLE patients with impending flare have varied numbers or function of T-regulatory cells (Alvarado-Sanchez et al., 2006; Bonelli et al., 2008), or possibly T-effector cells that are resistant to T-regulatory cell influence (Vargas-Rojas et al., 2008).

TNF-R superfamily members are a context-dependent group of ligand-receptor pairs (Croft et al., 2013) and the inventors detect significantly elevated levels of soluble members, including TNF-α and its receptors TNFRI and TNFRII, Fas and FasL, and CD40L/CD154 in pre-flare SLE patients. Ectodomain shedding of TNF-R family members occurs through the activation of ADAM (a disntegrin and metalloprotease) family members, most notably ADAM-17 (a.k.a. TNF-α converting enzyme (TACE)), which is upregulated in response to cellular activation and inhibited by the regulatory mediator IL-10. That SLE patients without impending disease flare had higher plasma levels of IL-10 may explain their significantly lower levels of soluble TNF-R family members. Further, TNFRI and TNFRII shedding suggest a reactive process to cellular activation in SLE patients with impending flare. Soluble TNF-α interacts primarily with TNFRI on a variety of cell types (Croft et al., 2013). TNFRII, activated optimally by membranous TNF-α (Croft et al., 2013), lowers the threshold of activation on T-effector cells, while contributing to the suppressive function of T-regulatory cells (Chen and Oppenheim 2011), in part from TNFRII shedding (Van Mierlo et al., 2008).

While individual markers may not universally correlate with development of flares, the overall balance between inflammatory and regulatory mediators could be a predictor of impending flares. Although varying pre-flare soluble plasma mediators were significantly altered in SLE patients who flared, correlated with disease activity at time of disease flare, and/or specifically contributed to the increased likelihood of disease flare (Tables 2-3 and Tables 6-7), the normalized, weighted, soluble inflammatory mediator score developed in this study enhanced the ability to discern factors that significantly contributed to downstream clinical sequelae in SLE patients with impending flare (Table 1 and Table 5 and FIGS. 8A-C and FIGS. 12A-C). Normalizing data from a diverse population carries the risk of false positive or negative results when comparing SLE patient populations at risk for disease flare. Therefore, further study of outliers and how to recognize them may be warranted. Future refinement of the combined mediator score utilized in SLE patients longitudinally must also address the effects of real-life parameters that may perturb immune regulation, such as medication regimens, infections, or vaccinations. The inventors previously demonstrated the rate of flare in this vaccination cohort is similar to that of non-vaccination cohort studies (Crowe et al., 2011), and others have demonstrated no increase in flare rate with vaccination (Mok et al., 2013 and Abu-Shakra et al., 2000). Further, the inventors see limited difference in soluble mediators between pre-flare (pre-vaccination) and flare (follow-up) time points in SLE patients who flare at either 6 or 12 weeks post-vaccination.

If larger prospective studies validate this approach, an optimized mediator score could become a valuable prognostic tool in experimental SLE trials and in lupus clinical care. For SLE patients with stable disease and relatively low risk of impending flare, it may be relatively safe to reduce treatments with significant side effects. Depending on the comprehensive clinical picture of an individual patient, early detection of risk for SLE flare could prompt closer monitoring, preventative treatments, or inclusion in clinical trials for targeted biologics relevant to pathways altered within the mediator score. In the future, chronic suppression of critical flare pathways and/or augmentation of regulatory pathways might promote longer periods of remission, decreased accumulation of organ damage over time, and better quality of life for SLE patients.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VII. REFERENCES

The following references, to the extent that they provide exemplary procedural or other details supplementary to those set forth herein, are specifically incorporated herein by reference.

Abu-Shakra et al., *J. Rheumatol.*, 27(7):1681-5, 2000.
Alvarado-Sanchez et al., *J. Autoimmun.*, 27(2):110-8, 2006.
Arend, *Cytokine Growth Factor Rev.*, 13(4-5):323-40, 2002.
Becker-Merok et al., *J. Rheumatol.* 37(10):2039-45, 2010.
Bonelli et al., *Int Immunol.*, 20(7):861-8, 2008.

Bruner et al., *Arthritis Rheum.* 64(11):3677-86, 2012.
Chen and Oppenheim, *Immunology,* 133(4):426-33, 2011.
Chen et al., *Lupus,* 21(13):1385-96, 2012.
Chu et al., *Arthritis Rheum.,* 60(7):2083-93, 2009.
Chun et al., *J. Clin. Immunol.,* 27(5):461-6, 2007.
Croft et al., *Nat Rev Drug Discov.,* 12(2):147-68, 2013.
Crowe et al., *Arthritis Rheum.* 2011.
Davas et al., *Clin Rheumatol.,* 18(1):17-22, 1999.
De Jager et al., *Semin. Nucl. Med.,* 23(2):165-179, 1993.
Desai-Mehta et al., *J. Clin. Invest.,* 97(9):2063-73, 1996.
Dillon et al., *Arthritis Res Ther.,* 12(2):R48, 2010.
Doolittle and Ben-Zeev, *Methods Mol. Biol.,* 109:215-237, 1999.
Dossus et al., *J. Immunol. Methods,* 350(1-2):125-32, 2009.
Dupont et al., *J. Reprod. Immunol.,* 66(2):175-91, 2005.
Espinosa et al., *Drugs of Today,* 46(12):891-9, 2010.
European Appln. EP 329 822
European Appln. EP 364 255
Frohman, In: PCR Protocols: A Guide To Methods And Applications, Academic Press, N.Y., 1990.
GB Application No. 2 202 328
Gomez et al., *Semin. Arthritis Rheum.,* 33(6):404-13, 2004.
Gulbis and Galand, *Hum. Pathol.,* 24(12):1271-1285, 1993.
Hochberg, *Arthritis Rheum.,* 40(9):1725, 1997.
Hughes-Austin et al., *Ann. Rheum. Dis.,* 2012.
Innis et al., *Proc. Natl. Acad. Sci. USA,* 85(24):9436-9440, 1988.
Kwoh et al., *Proc. Natl. Acad. Sci. USA,* 86:1173, 1989.
Lam and Petri, *Clin. Exp. Rheumatol.,* 23(5 Suppl 39):S120-32, 2005.
Lau and Mak, *Nat. Rev. Rheumatol.,* 5(7):400-4, 2009.
Lu et al., *Autoimmune Dis.* Doc Id. 819634, 2012.
Ma et al., *Clin. Rheumatol.,* 29(11):1251-8, 2010.
Miyara et al., *J. Immunol.,* 175(12):8392-400, 2005.
Mok et al., *Ann. Rheum Dis.,* 72(5):659-64, 2013.
Mok et al., *J. Rheumatol.,* 2010.
Mueller and Wold, *Science,* 246(4931):780-6, 1989.
Nakamura et al., In: Handbook of Experimental Immunology (4.sup.th Ed.), Weir et al., (eds). 1:27, Blackwell Scientific Publ., Oxford, 1987.
Ohara et al., *Proc. Natl. Acad. Sci. USA,* 86:5673-5677, 1989.
Okamoto et al., *Biomed Biotechnol.,* 2011:463412, 2011.
PCT Appln. US87/00880
PCT Appln. US89/01025
PCT Appln. WO88/10315
PCT Appln. WO89/06700
PCT Appln. WO90/07641
Petri et al., *Arthritis Rheum.,* 58(8):2453-9, 2008.
Petri et al., *J. Rheumatol.,* 36(11):2476-80, 2009.
Petri et al., *N. Engl. J. Med.,* 353(24):2550-8, 2005.
Qin et al., *Int. Immunopharmacol.,* 11(12):2167-75, 2011.
Ruperto et al., *Lupus* 0:1-10, 2010.
Sambrook et al., In: Molecular cloning, Cold Spring Harbor Laboratory Press, Cold Spring Harbor, N.Y., 2001.
Shah et al., *Arthritis Res Ther.,* 12(2):R53, 2010.
Sokolove et al., *PLoS One,* 7(5):e352962012.
Stringer et al., *J. Transl. Med.* 11(1):93, 2013.
Tinazzi et al., *Int Immunol.,* 21(3):237-43, 2009.
Tokano et al., *Clin Exp Immunol.,* 116(1):169-73, 1999.
U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,683,195
U.S. Pat. No. 4,683,202
U.S. Pat. No. 4,800,159
U.S. Pat. No. 4,883,750
U.S. Pat. No. 5,242,974
U.S. Pat. No. 5,279,721
U.S. Pat. No. 5,384,261
U.S. Pat. No. 5,405,783
U.S. Pat. No. 5,412,087
U.S. Pat. No. 5,424,186
U.S. Pat. No. 5,429,807
U.S. Pat. No. 5,436,327
U.S. Pat. No. 5,445,934
U.S. Pat. No. 5,472,672
U.S. Pat. No. 5,527,681
U.S. Pat. No. 5,529,756
U.S. Pat. No. 5,532,128
U.S. Pat. No. 5,545,531
U.S. Pat. No. 5,554,501
U.S. Pat. No. 5,554,744
U.S. Pat. No. 5,556,752
U.S. Pat. No. 5,561,071
U.S. Pat. No. 5,571,639
U.S. Pat. No. 5,593,839
U.S. Pat. No. 5,599,695
U.S. Pat. No. 5,624,711
U.S. Pat. No. 5,658,734
U.S. Pat. No. 5,700,637
U.S. Pat. No. 5,840,873
U.S. Pat. No. 5,843,640
U.S. Pat. No. 5,843,650
U.S. Pat. No. 5,843,651
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,849,487
U.S. Pat. No. 5,849,497
U.S. Pat. No. 5,849,546
U.S. Pat. No. 5,849,547
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,366
U.S. Pat. No. 5,882,864
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,630
U.S. Pat. No. 5,922,574
U.S. Pat. No. 5,925,517
U.S. Pat. No. 5,928,862
U.S. Pat. No. 5,928,869
U.S. Pat. No. 5,928,905
U.S. Pat. No. 5,928,906

U.S. Pat. No. 5,929,227
U.S. Pat. No. 5,932,413
U.S. Pat. No. 5,932,451
U.S. Pat. No. 5,935,791
U.S. Pat. No. 5,935,825
U.S. Pat. No. 5,939,291
U.S. Pat. No. 5,942,391
U.S. Pat. No. 6,004,755
Van Mierlo et al., *J. Immunol.*, 180(5):2747-51, 2008.
Vargas-Rojas et al., *Lupus*, 17(4):289-94, 2008.
Walker et al., *Nucleic Acids Res.* 20(7):1691-1696, 1992.
Wang et al., *Mol. Cell. Biol.*, 19:284-295, 1999.
Wang et al., *Nature*, 444:364, 2006.

The invention claimed is:

1. A method for assessing protein expression levels in a systemic lupus erythematosus (SLE) patient comprising:
   (a) obtaining a blood, serum or plasma sample from the SLE patient;
   (b) assessing protein expression levels of at least one cytokine from each of (i), (ii), (iii), and (iv), wherein (i) is an innate-type cytokine selected from an interleukin-1 alpha (IL-1α), an interleukin-1 beta (IL-1β), an interferon-alpha (IFN-α), interferon-beta (IFN-β), a granulocyte-colony stimulating factor 3 (G-CSF), interleukin-7 (IL-7), and an interleukin-15 (IL-15), (ii) is a T-helper type-1 (Th1) cytokine selected from an interleukin-2 (IL-2), an interleukin-12 (IL-12), and an interferon-gamma (IFN-γ), (iii) is a T-helper type-2 (Th2) cytokine selected from an interleukin-4 (IL-4), an interleukin-5 (IL-5), and an interleukin-13 (IL-13), and (iv) is a T-helper type-17 (Th17) cytokine selected from an interleukin-6 (IL-6), an interleukin-17A (IL-17A), an interleukin-21 (IL-21), and an interleukin-23 (IL-23); and
   (c) assessing protein expression levels of each molecule from each of (v), (vi), (vii), and (viii), wherein (v) comprises the following chemokine(s) or adhesion molecules: a C—X—C motif chemokine ligand 8 (CXCL8)/interleukin-8 (IL-8), a C—X—C motif chemokine ligand 10 (CXCL10)/IFN-gamma-inducible protein 10 (IP-10), one or both of a C—C motif chemokine ligand 5 (CCL5) and regulated on activation normal T cell expressed and secreted (RANTES), a C—C motif chemokine ligand 2 (CCL2)/monocyte chemoattractant protein-1 (MCP-1), a C—C motif chemokine ligand 7 (CCL7)/monocyte chemoattractant protein-3 (MCP-3), a C—C motif chemokine ligand 3 (CCL3)/macrophage inflammatory protein-1 alpha (MIP-1α), a C—C motif chemokine ligand 4 (CCL4)/macrophage inflammatory protein-1 beta (MIP-1β), a C—X—C motif chemokine ligand 1 (CXCL1)/growth-regulated oncogene-alpha (GRO-α), a C—X—C motif chemokine ligand 9 (CXCL9)/monokine induced by interferon-gamma (MIG), an eotaxin, an Intercellular Adhesion Molecule 1 (ICAM-1), and an E-selectin, (vi) comprises the following tumor necrosis factor receptor (TNFR) superfamily member molecules: a tumor necrosis factor alpha (TNF-α), a tumor necrosis factor receptor I (TNFRI), a tumor necrosis factor receptor II (TNFRII), a tumor necrosis factor-related apoptosis-inducing ligand (TRAIL), a first apoptosis signal (Fas), a first apoptosis signal ligand (FasL), a B-lymphocyte stimulator (BLyS), a proliferation-inducing ligand (APRIL), and a nerve growth factor-beta (NGFβ), (vii) comprises the following regulatory mediator molecules: an interleukin-10 (IL-10), a transforming growth factor beta (TGF-β), a C—X—C motif chemokine ligand 12 (CXCL12)/stromal cell-derived factor 1 (SDF-1), and an interleukin-1 receptor antagonist (IL-1RA), and (viii) comprises the following systemic lupus erythematosus (SLE) mediator molecules: a leukemia inhibitor factor (LIF), a plasminogen activator inhibitor-1 (PAI-1), a platelet-derived growth factor subunit beta homodimer (PDGF-BB), a leptin, a stem cell factor (SCF), and an interleukin-2 receptor alpha chain (IL-2RA).

2. The method of claim 1, wherein each cytokine from each of (i), (ii), (iii), and (iv) is assessed.

3. The method of claim 1, wherein assessing comprises immunologic detection.

4. The method of claim 3, wherein the immunologic detection comprises flow cytometry, enzyme-linked immunosorbent assay (ELISA), radioimmunoassay (RIA), or Western blot.

5. The method of claim 3, wherein the immunologic detection comprises a multiplexed bead-based assay.

6. The method of claim 1, wherein the eotaxin is eotaxin-1.

7. The method of claim 4, wherein the immunologic detection comprises ELISA.

* * * * *